(12) United States Patent
Kshirsagar et al.

(10) Patent No.: US 7,648,997 B2
(45) Date of Patent: Jan. 19, 2010

(54) HYDROXYLAMINE SUBSTITUTED IMIDAZOQUINOLINES

(75) Inventors: Tushar A. Kshirsagar, Woodbury, MN (US); David T. Amos, St. Paul, MN (US); Joseph F. Dellaria, Jr., Woodbury, MN (US); Philip D. Heppner, Forest Lake, MN (US); Scott E. Langer, Woodbury, MN (US); Bernhard M. Zimmermann, Eagan, MN (US)

(73) Assignee: Coley Pharmaceutical Group, Inc., New York, NY (US)

( * ) Notice: Subject to any disclaimer, the term of this patent is extended or adjusted under 35 U.S.C. 154(b) by 270 days.

(21) Appl. No.: 10/595,058

(22) PCT Filed: Aug. 12, 2004

(86) PCT No.: PCT/US2004/026158

§ 371 (c)(1),
(2), (4) Date: Jan. 23, 2006

(87) PCT Pub. No.: WO2005/018556

PCT Pub. Date: Mar. 3, 2005

(65) Prior Publication Data

US 2008/0114019 A1     May 15, 2008

Related U.S. Application Data

(60) Provisional application No. 60/494,608, filed on Aug. 12, 2003, provisional application No. 60/494,605, filed on Aug. 12, 2003.

(51) Int. Cl.
    *A61K 31/437* (2006.01)
(52) U.S. Cl. ......................................... 514/293; 546/82
(58) Field of Classification Search ................. 514/293
    See application file for complete search history.

(56) References Cited

U.S. PATENT DOCUMENTS

| | | | |
|---|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gerster |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Llindstrom et al. |
| 5,482,936 A | 1/1996 | Lindstrom |
| 5,693,811 A | 12/1997 | Lindstrom |
| 5,741,908 A | 4/1998 | Gerster et al. |
| 5,756,747 A | 5/1998 | Gerster et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,451,810 B1 | 9/2002 | Coleman et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,465 B2 | 2/2004 | Dellaria et al. |
| 6,706,728 B2 | 3/2004 | Hedenstrom et al. |
| 6,743,920 B2 | 6/2004 | Lindstrom et al. |
| 6,756,382 B2 | 6/2004 | Coleman et al. |

(Continued)

FOREIGN PATENT DOCUMENTS

EP          0 394 026          10/1990

(Continued)

OTHER PUBLICATIONS

U.S. Appl. No. 10/595,792 (closest art available).*

(Continued)

*Primary Examiner*—Kamal A Saeed
*Assistant Examiner*—Valerie Rodriguez-Garcia
(74) *Attorney, Agent, or Firm*—Wolf, Greenfield & Sacks, P.C.; Gregg C. Benson

(57) ABSTRACT

Imidazo-containing compounds (e.g., imidazoquinolines, imidazonaphthyridines, imidazopyridines) with a hydroxylamine substituent at the 1-position, pharmaceutical compositions containing the compounds, intermediates, and methods of use of these compounds as immunomodulators, for inducing cytokine biosynthesis in animals and in the treatment of diseases including viral and neoplastic diseases are disclosed.

25 Claims, No Drawings

U.S. PATENT DOCUMENTS

| | | | |
|---|---|---|---|
| 6,797,718 B2 | 9/2004 | Dellaria et al. | |
| 6,818,650 B2 | 11/2004 | Griesgraber | |
| 6,841,678 B2 | 1/2005 | Merli et al. | |
| 6,852,861 B2 | 2/2005 | Merli et al. | |
| 7,427,629 B2 * | 9/2008 | Kedl et al. | 514/279 |
| 2002/0016332 A1 | 2/2002 | Slade | |
| 2002/0055517 A1 | 5/2002 | Smith | |
| 2002/0058674 A1 | 5/2002 | Hedenstrom et al. | |
| 2002/0107262 A1 | 8/2002 | Lindstrom | |
| 2002/0110840 A1 | 8/2002 | Tomai et al. | |
| 2003/0096835 A1 | 5/2003 | Crooks et al. | |
| 2003/0130299 A1 | 7/2003 | Crooks et al. | |
| 2003/0133913 A1 | 7/2003 | Tomai et al. | |
| 2003/0139364 A1 | 7/2003 | Krieg et al. | |
| 2003/0144286 A1 | 7/2003 | Frenkel et al. | |
| 2003/0161797 A1 | 8/2003 | Miller et al. | |
| 2003/0199538 A1 * | 10/2003 | Skwierczynski et al. | 514/291 |
| 2004/0014779 A1 | 1/2004 | Gorden et al. | |
| 2004/0091491 A1 | 5/2004 | Kedl et al. | |
| 2004/0132079 A1 | 7/2004 | Gupta et al. | |
| 2004/0141950 A1 | 7/2004 | Noelle et al. | |
| 2004/0147543 A1 | 7/2004 | Hays et al. | |
| 2004/0162309 A1 | 8/2004 | Gorden et al. | |
| 2004/0171086 A1 | 9/2004 | Fink et al. | |
| 2004/0175336 A1 | 9/2004 | Egging et al. | |
| 2004/0176367 A1 | 9/2004 | Griesgraber et al. | |
| 2004/0180919 A1 | 9/2004 | Lee et al. | |
| 2004/0181130 A1 | 9/2004 | Fox et al. | |
| 2004/0181211 A1 | 9/2004 | Elliott et al. | |
| 2004/0191833 A1 | 9/2004 | Fink et al. | |
| 2004/0192585 A1 | 9/2004 | Fox et al. | |
| 2004/0197865 A1 | 10/2004 | Gupta et al. | |
| 2004/0202720 A1 | 10/2004 | Wightman et al. | |
| 2004/0214851 A1 | 10/2004 | Birmachu et al. | |
| 2005/0054590 A1 | 3/2005 | Averett | |
| 2005/0085500 A1 | 4/2005 | Gutman et al. | |
| 2005/0165236 A1 | 7/2005 | Colombo et al. | |
| 2005/0245562 A1 | 11/2005 | Garcia-Echeverria et al. | |
| 2007/0066639 A1 | 3/2007 | Kshirsagar et al. | |

FOREIGN PATENT DOCUMENTS

| | | |
|---|---|---|
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | WO 02/36592 | 5/2002 |
| WO | WO 2005/018551 | 3/2005 |
| WO | WO 2005/018555 | 3/2005 |
| WO | WO 2005/018556 | 3/2005 |
| WO | WO 2005/020999 | 3/2005 |
| WO | WO 2005/032484 | 4/2005 |
| WO | WO 2005/048933 | 6/2005 |
| WO | WO 2005/048945 | 6/2005 |
| WO | WO 2005/051317 | 6/2005 |
| WO | WO 2005/051324 | 6/2005 |
| WO | WO 2005/054237 | 6/2005 |
| WO | WO 2005/054238 | 6/2005 |
| WO | WO 2005/066169 | 7/2005 |
| WO | WO 2005/066170 | 7/2005 |
| WO | WO 2005/066172 | 7/2005 |
| WO | WO 2005/076783 | 8/2005 |
| WO | WO 2005/079195 | 9/2005 |
| WO | WO 2005/094531 | 10/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |

OTHER PUBLICATIONS

Wozniak, et al, "The Amination of 3-nitro-1, 5-naphthyridines by Liquid Ammonia/Postassium Permanganate[1,2]. A New and Convenient Amination Method.", *Journal of the Royal Netherlands Chemical Society*, 102, pp. 511-513, Dec. 12, 1983.

Brennan, et al., "Automated Bioassay of Interferons in Micro-test Plates", *Biotechniques*, Jun./Jul., 78, 1983.

Testerman, et al., "Cytokine Induction by the Immunomodulators Imiquimod and S-27609", *Journal of Leukocyte Biology*, vol. 58, pp. 365-372, Sep. 1995.

Bachman, et al, "Synthesis of Substituted Quinolylamines. Derivatives of 4-Amino-7-Chloroquinoline", *J. Org. Chem*, 15, pp. 1278-1284 (1950).

Jain, et al, "Chemical and Pharmacological Investigations of Some ω-Substituted Alkylamino-3-aminopyridines", *J. Med. Chem.*, 11, pp. 87-92 (1968).

Baranov, et al., *Chem. Abs*. 85, 94362, (1976).

Berényi, et al, "Ring Transformation of Condensed Dihydro-as-triazines", *J. Heterocyclic Chem.*, 18, pp. 1537-1540 (1981).

Chollet, et al, "Development of a Topically Active Imiquimod Formulation", *Pharmaceutical Development and Technology*, 4(1), pp. 35-43 (1999).

Izumi, et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines", *Bioorganic & Medicinal Chemistry*, 11, pp. 2541-2550 (2003).

Supplementary Partial European Search Report (EP 04780922.3), Jun. 25, 2009.

Macchia et al., Synthesis and antiviral properties of 9-[(2-methyleneaminoxyethoxy)methyl]guanine derivatives as novel Acyclovir analogues. Farmaco. Feb. 2000;55(2):104-8.

* cited by examiner

HYDROXYLAMINE SUBSTITUTED IMIDAZOQUINOLINES

RELATED APPLICATIONS

This application is the National Stage of International Application No. PCT/US2004/026158, filed Aug. 12, 2004, which claims priority to U.S. Provisional Application Ser. No. 60/494,605, filed Aug. 12, 2003, and U.S. Provisional Application Ser. No. 60/494,608, filed Aug. 12, 2003, both of which are incorporated herein by reference.

BACKGROUND

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers (IRMs), rendering them useful in the treatment of a variety of disorders.

There continues to be interest in and a need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula I:

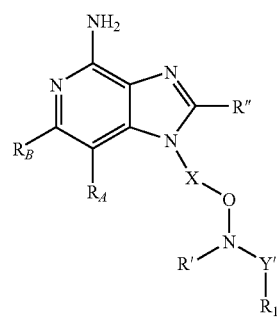

I and, more particularly, compounds of the following Formula II:

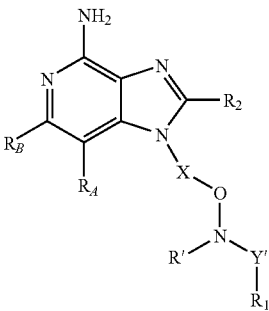

II wherein: X, $R_A$, $R_B$, R', R", Y', $R_1$, and $R_2$ are as defined below.

Examples of such compounds include imidazoquinolines of the following Formulas III, IV, and V, and imidazotetrahydroquinolines of the following Formula VII:

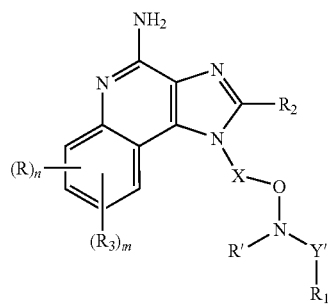

III

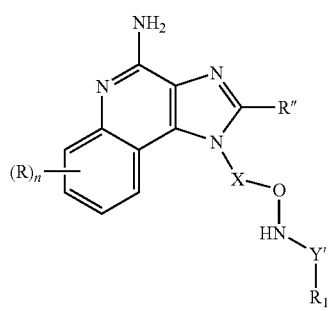

IV

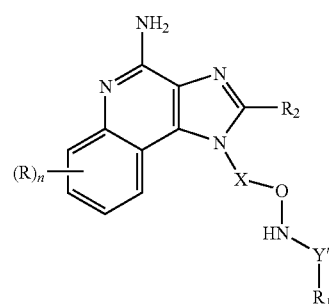

V

-continued

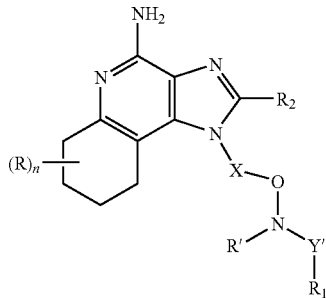

VII wherein: X, R, R', R", Y', $R_1$, $R_2$, $R_3$, m, and n are as defined below.

Examples of such compounds also include imidazopyridines of the following Formula VI:

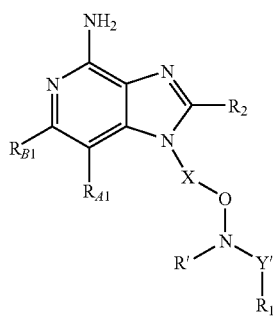

VI wherein: X, $R_{A1}$, $R_{B1}$, R', Y', $R_1$, and $R_2$ are as defined below.

Examples of such compounds also include imidazonaphthyridines of the following Formula VIII and imidazotetrahydronaphthyridines of the following Formula IX:

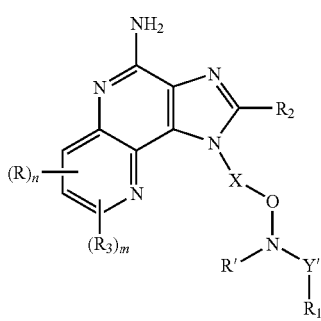

VIII

-continued

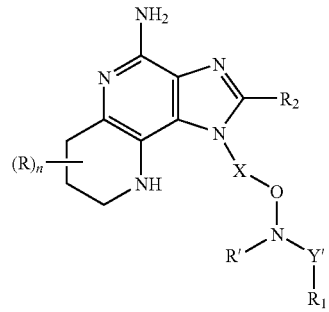

IX wherein: X, R, R', Y', $R_1$, $R_2$, $R_3$, m, and n are as defined below.

The compounds of Formula I are useful as immune response modifiers due to their ability to induce cytokine biosynthesis (e.g., induces the synthesis of at least one cytokine) and otherwise modulate the immune response when administered to animals. This makes the compounds useful in the treatment of a variety of conditions such as viral diseases and tumors that are responsive to such changes in the immune response.

The invention further provides pharmaceutical compositions containing an effective amount of a compound of Formula I and methods of inducing cytokine biosynthesis in an animal, treating a viral infection and/or treating a neoplastic disease in an animal by administering an effective amount of a compound of Formula I to the animal.

In addition, methods of synthesizing compounds of Formula I and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I through IX:

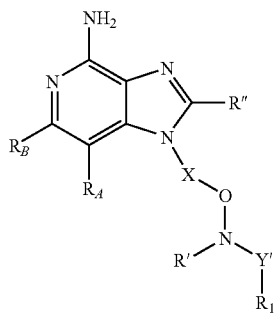

I

II
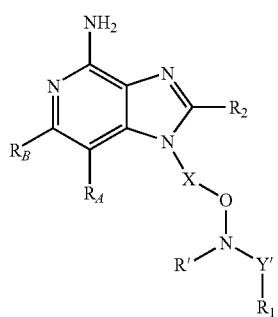
III
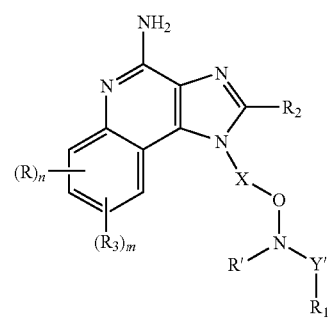
IV
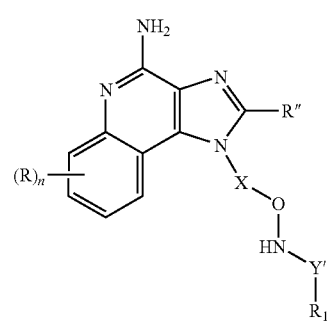
V
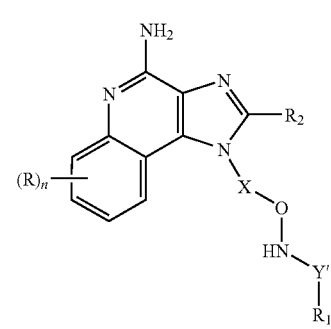
VI
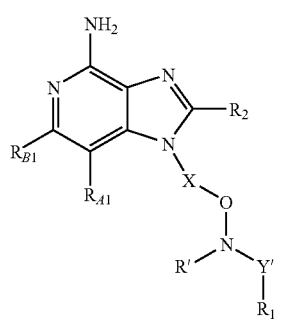
VIII
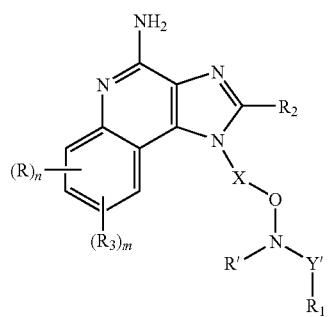
IX
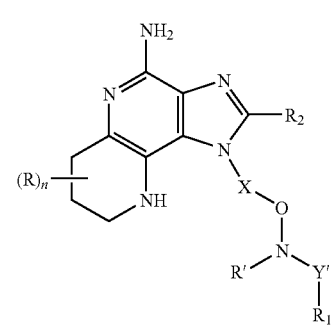
as well as intermediates of the following Formulas X through XIV:
X
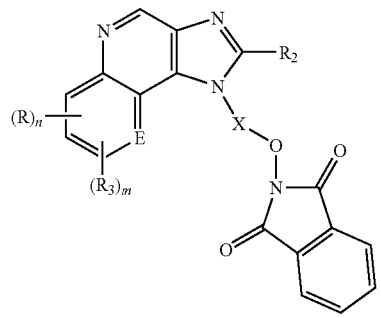
XI
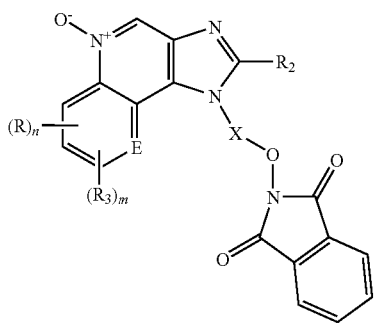

-continued

XII

[Structure: imidazoquinoline with R₂ substituent and X-O-phthalimide group, (R)ₙ on benzene ring]

XIII

[Structure: N-oxide imidazoquinoline with R₂ substituent and X-O-phthalimide group, (R)ₙ on benzene ring]

XIV

[Structure: 4-amino imidazoquinoline with R₂ substituent and X-O-NH₂ group, (R)ₙ on benzene ring]

wherein: E, X, R, R', R'', R₁, R₂, R₃, Y', R_A, R_B, R_{A1}, R_{B1}, m, and n are as defined below.

In one embodiment, the present invention provides a compound of Formula I:

I

[Structure: 4-amino imidazopyridine with R'', R_A, R_B substituents and X-O-N(R')-Y'-R₁ group]

wherein:
X is selected from the group consisting of —CH(R_{9a})-alkylene- and —CH(R_{9a})-alkenylene-, wherein the alkylene and alkenylene are optionally interrupted by one or more —O— groups;

Y' is selected from the group consisting of:
a bond,
—C(O)—,
—C(S)—,
—S(O)₂—,
—S(O)₂—N(R₈)—, —S(O)₂—N⌒R₁₀ (ring), —C(O)—O—,
—C(O)—N(R₈)—,
—C(S)—N(R₈)—,
—C(O)—N(R₈)—S(O)₂—,
—C(O)—N(R₈)—C(O)—,
—C(S)—N(R₈)—C(O)—, —C(O)—N⌒R₁₀ (ring), —C(O)—C(O)—,
—C(O)—C(O)—O—, and
—C(=NH)—N(R₈)—;

R₁ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—S(O)₀₋₂-alkyl,
—S(O)₀₋₂-aryl,
—NH—S(O)₂-alkyl,
—NH—S(O)₂-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R₈)₂,
—N(R₈)—C(O)-alkyl,
—O—C(O)-alkyl, and
—C(O)-alkyl;

or R₁ and R' together with the nitrogen atom and Y' to which they are bonded can join to form a ring selected from the group consisting of:

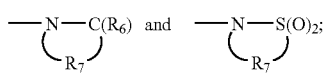

$R_A$ and $R_B$ are each independently selected from the group consisting of:
hydrogen,
halogen,
alkyl,
alkenyl,
alkoxy,
alkylthio, and
—$N(R_9)_2$;
or when taken together, $R_A$ and $R_B$ form a fused aryl ring or heteroaryl ring containing one heteroatom selected from the group consisting of N and S, wherein the aryl or heteroaryl ring is unsubstituted or substituted by one or more R''' groups;
or when taken together, $R_A$ and $R_B$ form a fused 5 to 7 membered saturated ring, optionally containing one heteroatom selected from the group consisting of N and S, and unsubstituted or substituted by one or more R groups;
R is selected from the group consisting of:
halogen,
hydroxyl,
alkyl,
alkenyl,
haloalkyl,
alkoxy,
alkylthio, and
—$N(R_9)_2$;
$R_6$ is selected from the group consisting of =O and =S;
$R_7$ is $C_{2-7}$ alkylene;
each $R_8$ is independently selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;
each $R_9$ is independently selected from the group consisting of hydrogen and alkyl;
$R_{9a}$ is selected from the group consisting of hydrogen and alkyl which is optionally interrupted by one or more —O— groups;
$R_{10}$ is $C_{3-8}$ alkylene;
R'' is hydrogen or a non-interfering substituent; and
each R''' is a non-interfering substituent;

or a pharmaceutically acceptable salt thereof.

In one embodiment, the present invention provides a compound of Formula II:

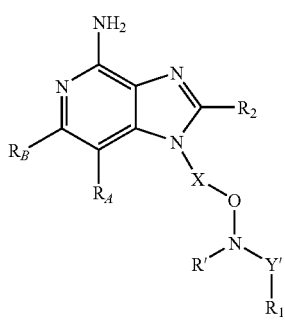

II wherein:
X is selected from the group consisting of —$CH(R_{9a})$-alkylene- and —$CH(R_{9a})$-alkenylene-, wherein the alkylene and alkenylene are optionally interrupted by one or more —O— groups;
Y' is selected from the group consisting of:
a bond,
—C(O)—,
—C(S)—,
—$S(O)_2$—,
—$S(O)_2$—$N(R_8)$—,

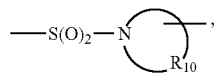

—C(O)—O—,
—C(O)—$N(R_8)$—,
—C(S)—$N(R_8)$—,
—C(O)—$N(R_8)$—$S(O)_2$—,
—C(O)—$N(R_8)$—C(O)—,
—C(S)—$N(R_8)$—C(O)—,

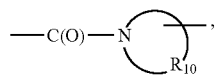

—C(O)—C(O)—,
—C(O)—C(O)—O—, and
—C(=NH)—$N(R_8)$—;
$R_1$ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—$S(O)_{0-2}$-alkyl,
—$S(O)_{0-2}$-aryl,
—NH—$S(O)_2$-alkyl,
—NH—$S(O)_2$-aryl,
haloalkoxy,
halogen,
nitrile,
nitro,
aryl,
heteroaryl,
heterocyclyl,
aryloxy,
arylalkyleneoxy, —C(O)—O-alkyl,
—C(O)—N(R$_8$)$_2$,
—N(R$_8$)—C(O)-alkyl,
—O—C(O)-alkyl, and
—C(O)-alkyl;

or R$_1$ and R' together with the nitrogen atom and Y' to which they are bonded can join to form a ring selected from the group consisting of:

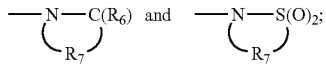

R$_A$ and R$_B$ are each independently selected from the group consisting of:
hydrogen,
halogen,
alkyl,
alkenyl,
alkoxy,
alkylthio, and
—N(R$_9$)$_2$;

or when taken together, R$_A$ and R$_B$ form a fused aryl ring or heteroaryl ring containing one heteroatom selected from the group consisting of N and S, wherein the aryl or heteroaryl ring is unsubstituted or substituted by one or more R groups, or substituted by one R$_3$ group, or substituted by one R$_3$ group and one R group;

or when taken together, R$_A$ and R$_B$ form a fused 5 to 7 membered saturated ring, optionally containing one heteroatom selected from the group consisting of N and S, and unsubstituted or substituted by one or more R groups;

R is selected from the group consisting of:
halogen,
hydroxyl,
alkyl,
alkenyl,
haloalkyl,
alkoxy,
alkylthio, and
—N(R$_9$)$_2$;

R$_2$ is selected from the group consisting of:
—R$_4$,
—X'—R$_4$,
—X'—Y—R$_4$, and
—X'—R$_5$;

R$_3$ is selected from the group consisting of:
—Z—R$_4$,
—Z—X'—R$_4$,
—Z—X'—Y—R$_4$, and
—Z—X'—R$_5$;

each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

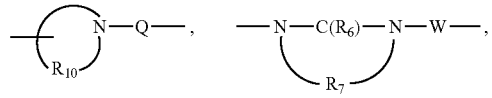

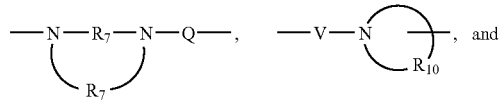

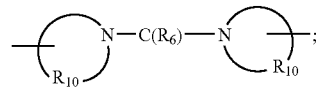

Z is a bond or —O—;
each R$_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each R$_5$ is independently selected from the group consisting of:

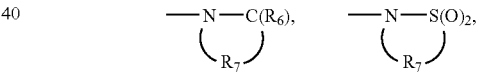

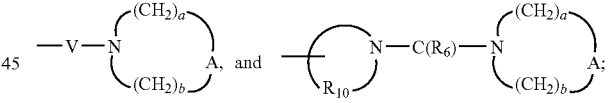

each R$_6$ is independently selected from the group consisting of =O and =S;
each R$_7$ is independently C$_{2-7}$ alkylene;
each R$_8$ is independently selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;
each R$_9$ is independently selected from the group consisting of hydrogen and alkyl;
R$_{9a}$ is selected from the group consisting of hydrogen and alkyl which is optionally interrupted by one or more —O— groups;
each R$_{10}$ is independently C$_{3-8}$ alkylene;
each A is independently selected from the group consisting of —O—, —C(O)—, —CH$_2$—, —S(O)$_{0-2}$—, and —N(R$_4$)—;
each Q is independently selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

each W is independently selected from the group consisting of a bond, —C(O)—, and —S(O)$_2$—;

each V is independently selected from the group consisting of —C(R$_6$)—, —O—C(R$_6$)—, —N(R$_8$)—C(R$_6$)—, and —S(O)$_2$—; and a and b are independently integers from 1 to 6 with the proviso that a+b is ≦7;

or a pharmaceutically acceptable salt thereof.

In one embodiment, the present invention provides a compound of Formula III:

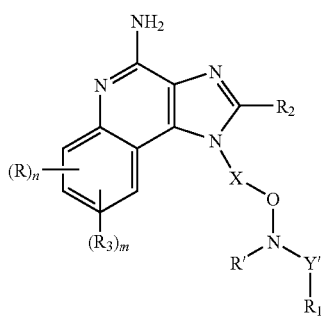

III wherein:

X is selected from the group consisting of —CH(R$_{9a}$)-alkylene- and —CH(R$_{9a}$)-alkenylene-, wherein the alkylene and alkenylene are optionally interrupted by one or more —O— groups;

Y' is selected from the group consisting of:
a bond,
—C(O)—,
—C(S)—,
—S(O)$_2$—,
—S(O)$_2$—N(R$_8$)—,

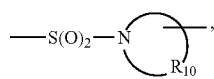

—C(O)—O—,
—C(O)—N(R$_8$)—,
—C(S)—N(R$_8$)—,
—C(O)—N(R$_8$)—S(O)$_2$—,
—C(O)—N(R$_8$)—C(O)—,
—C(S)—N(R$_8$)—C(O)—,

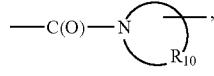

—C(O)—C(O)—,
—C(O)—C(O)—O—, and
—C(=NH)—N(R$_8$)—;

each R is independently selected from the group consisting of:
halogen,
hydroxyl,
alkyl,
alkenyl,
haloalkyl,
alkoxy,
alkylthio, and
—N(R$_9$)$_2$;

R$_1$ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—C(O)-alkyl, and
—C(O)-alkyl;

or R$_1$ and R' together with the nitrogen atom and Y' to which they are bonded can join to form a ring selected from the group consisting of:

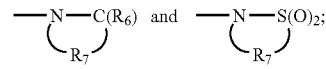

R$_2$ is selected from the group consisting of:
—R$_4$,
—X'—R$_4$,
—X'—Y—R$_4$, and
—X'—R$_5$;

R$_3$ is selected from the group consisting of:
—Z—R$_4$,
—Z—X'—R$_4$,
—Z—X'—Y—R$_4$, and
—Z—X'—R$_5$;

each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

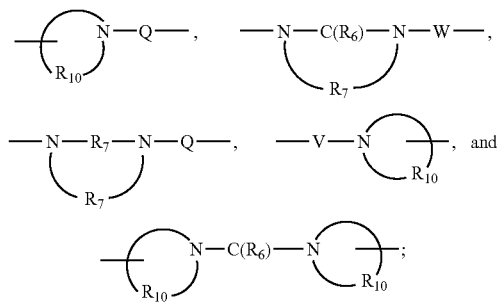

Z is a bond or —O—;

each R$_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each R$_5$ is independently selected from the group consisting of:

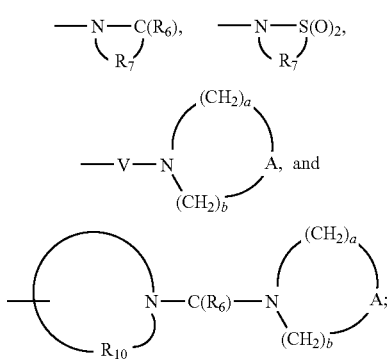

each R$_6$ is independently selected from the group consisting of =O and =S;

each R$_7$ is independently C$_{2-7}$ alkylene;
each R$_8$ is independently selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;
each R$_9$ is independently selected from the group consisting of hydrogen and alkyl;
R$_{9a}$ is selected from the group consisting of hydrogen and alkyl which is optionally interrupted by one or more —O— groups;
each R$_{10}$ is independently C$_{3-8}$ alkylene;
each A is independently selected from the group consisting of —O—, —C(O)—, —CH$_2$—, —S(O)$_{0-2}$—, and —N(R$_4$)—;
each Q is independently selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
each W is independently selected from the group consisting of a bond, —C(O)—, and —S(O)$_2$—;
each V is independently selected from the group consisting of —C(R$_6$)—, —O—C(R$_6$)—, —N(R$_8$)—C(R$_6$)—, and —S(O)$_2$—;
a and b are independently integers from 1 to 6 with the proviso that a+b is ≦7;
n is an integer from 0 to 4; and
m is 0 or 1, with the proviso that when m is 1, n is 0 or 1;

or a pharmaceutically acceptable salt thereof.

In one embodiment, the present invention provides a compound of Formula IV:

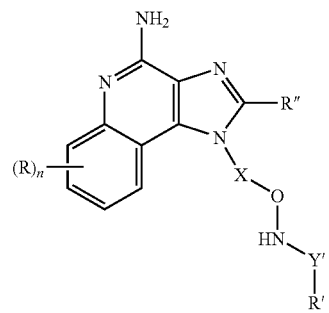

IV wherein:
X is selected from the group consisting of —CH(R$_{9a}$)-alkylene- and —CH(R$_{9a}$)-alkenylene-;
Y' is selected from the group consisting of:
a bond,
—C(O)—,
—C(S)—,
—S(O)$_2$—,
—S(O)$_2$—N(R$_{8a}$)—,
—C(O)—O—,
—C(O)—N(R$_{8a}$)—,
—C(S)—N(R$_{8a}$)—,
—C(O)—N(R$_{8a}$)—S(O)$_2$—,
—C(O)—N(R$_{8a}$)—C(O)—,
—C(S)—N(R$_{8a}$)—C(O)—, and
—C(O)—C(O)—O—;
R$_1$ is selected from the group consisting of:
hydrogen,
alkyl,
alkenyl,
aryl, alkylene-aryl,
alkylene-heteroaryl,
alkylene-heterocyclyl,
heteroaryl,
heterocyclyl, and
alkyl, alkenyl, aryl, arylalkylenyl, heteroarylalkylenyl, heterocyclylalkylenyl, heteroaryl or heterocyclyl, substituted by one or more substituents selected from the group consisting of:
hydroxyl,
alkyl,
haloalkyl,
hydroxyalkyl,
—O-alkyl,
—S(O)$_{0-2}$-alkyl,
—S(O)$_{0-2}$-aryl,
—O-haloalkyl,
halogen,
nitrile,
nitro,
aryl,
heteroaryl,
heterocyclyl,
—O-aryl,
—O-alkylene-aryl,
—C(O)—O-alkyl,
—C(O)—N(R$_{8a}$)$_2$,
—N(R$_{8a}$)—C(O)-alkyl,
—O—C(O)-alkyl, and
—C(O)-alkyl;

each R and R" are independently selected from the group consisting of hydrogen and non-interfering substituents;

R$_{9a}$ is selected from the group consisting of hydrogen and alkyl which may be optionally interrupted by one or more —O— groups;

each R$_{8a}$ is independently selected from the group consisting of hydrogen, C$_{1-10}$ alkyl, and C$_{2-10}$ alkenyl; and n is an integer from 0 to 4;

or a pharmaceutically acceptable salt thereof.

In one embodiment, the present invention provides a compound of Formula V:

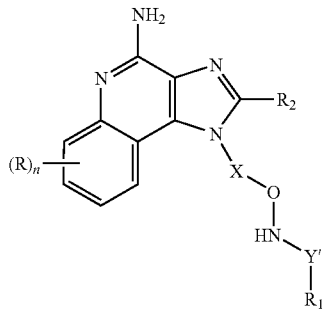

V wherein:
X is selected from the group consisting of —CH(R$_{9a}$)-alkylene- and —CH(R$_{9a}$)-alkenylene-;
Y' is selected from the group consisting of:
a bond,
—C(O)—,
—C(S)—,
—S(O)$_2$—,
—S(O)$_2$—N(R$_{8a}$)—,
—C(O)—O—,
—C(O)—N(R$_{8a}$)—,
—C(S)—N(R$_{8a}$)—,
—C(O)—N(R$_{8a}$)—S(O)$_2$—,
—C(O)—N(R$_{8a}$)—C(O)—,
—C(S)—N(R$_{8a}$)—C(O)—, and
—C(O)—C(O)—O—;
R$_1$ is selected from the group consisting of:
hydrogen,
alkyl,
alkenyl,
aryl,
alkylene-aryl,
alkylene-heteroaryl,
alkylene-heterocyclyl,
heteroaryl,
heterocyclyl, and
alkyl, alkenyl, aryl, arylalkylenyl, heteroarylalkylenyl, heterocyclylalkylenyl, heteroaryl or heterocyclyl, substituted by one or more substituents selected from the group consisting of:
hydroxyl,
alkyl,
haloalkyl,
hydroxyalkyl,
—O-alkyl,
—S(O)$_{0-2}$-alkyl,
—S(O)$_{0-2}$-aryl,
—O-haloalkyl,
halogen,
nitrile,
nitro,
aryl,
heteroaryl,
heterocyclyl,
—O-aryl,
—O-alkylene-aryl,
—C(O)—O-alkyl,
—C(O)—N(R$_{8a}$)$_2$,
—N(R$_{8a}$)—C(O)-alkyl,
—O—C(O)-alkyl, and
—C(O)-alkyl;
each R is independently selected from the group consisting of alkyl, alkoxy, halogen, hydroxyl, and trifluoromethyl;
R$_2$ is selected from the group consisting of:
hydrogen,
alkyl,
alkenyl,
aryl,
heteroaryl,
heterocyclyl,
alkylene-Y"-alkyl,
alkylene-Y"-alkenyl,
alkylene-Y"-aryl, and
alkyl or alkenyl substituted by one or more substituents selected from the group consisting of:
hydroxyl,
halogen,
—N(R$_{8a}$)$_2$,
—C(O)—C$_{1-10}$ alkyl,
—C(O)—O—C$_{1-10}$ alkyl,
—N$_3$,
aryl,
heteroaryl,
heterocyclyl,
—C(O)-aryl, and
—C(O)-heteroaryl;

Y" is —O— or —S(O)$_{0-2}$—;
each R$_{8a}$ is independently selected from the group consisting of hydrogen, C$_{1-10}$ alkyl, and C$_{2-10}$ alkenyl;
R$_{9a}$ is selected from the group consisting of hydrogen and alkyl which may be optionally interrupted by one or more —O— groups; and
n is an integer from 0 to 4;

or a pharmaceutically acceptable salt thereof.

In one embodiment, the present invention provides a compound of Formula VI:

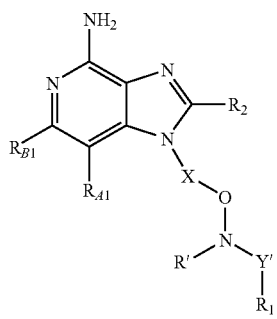

wherein:

X is selected from the group consisting of —CH(R$_{9a}$)-alkylene- and —CH(R$_{9a}$)-alkenylene-, wherein the alkylene and alkenylene are optionally interrupted by one or more —O— groups;

Y' is selected from the group consisting of:
a bond,
—C(O)—,
—C(S)—,
—S(O)$_2$—,
—S(O)$_2$—N(R$_8$)—,

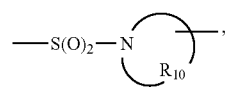

—C(O)—O—,
—C(O)—N(R$_8$)—,
—C(S)—N(R$_8$)—,
—C(O)—N(R$_8$)—S(O)$_2$—,
—C(O)—N(R$_8$)—C(O)—,
—C(S)—N(R$_8$)—C(O)—,

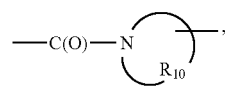

—C(O)—C(O)—,
—C(O)—C(O)—O—, and
—C(=NH)—N(R$_8$)—;

R$_1$ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—C(O)-alkyl, and
—C(O)-alkyl;

or R$_1$ and R' together with the nitrogen atom and Y' to which they are bonded can join to form a ring selected from the group consisting of:

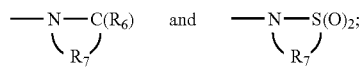

R$_{A1}$ and R$_{B1}$ are each independently selected from the group consisting of:
hydrogen,
halogen,
alkyl,
alkenyl,
alkoxy,
alkylthio, and
—N(R$_9$)$_2$;

R$_2$ is selected from the group consisting of:
—R$_4$,
—X'—R$_4$,
—X'—Y—R$_4$, and
—X'—R$_5$;

X' is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—, —O—C(O)—O—,
—N($R_8$)-Q-,
—C($R_6$)—N($R_8$)—,
—O—C($R_6$)—N($R_8$)—,
—C($R_6$)—N(O$R_9$)—,

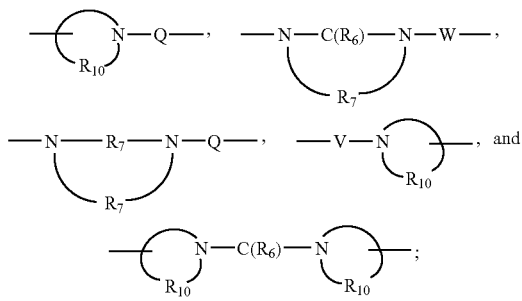

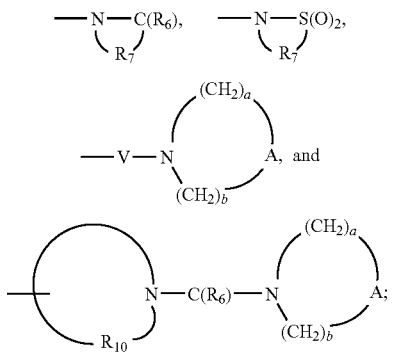

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

each $R_6$ is independently selected from the group consisting of =O and =S;
each $R_7$ is independently $C_{2-7}$ alkylene;
each $R_8$ is independently selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;
each $R_9$ is independently selected from the group consisting of hydrogen and alkyl;
$R_{9a}$ is selected from the group consisting of hydrogen and alkyl which is optionally interrupted by one or more —O— groups;
each $R_{10}$ is independently $C_{3-8}$ alkylene;
A is selected from the group consisting of —O—, —C(O)—, —CH$_2$—, —S(O)$_{0-2}$—, and —N($R_4$)—;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;
W is selected from the group consisting of a bond, —C(O)—, and —S(O)$_2$—;
V is selected from the group consisting of —C($R_6$)—, —O—C($R_6$)—, —N($R_8$)—C($R_6$)—, and —S(O)$_2$—; and
a and b are independently integers from 1 to 6 with the proviso that a+b is ≦7;

or a pharmaceutically acceptable salt thereof.
In one embodiment, the present invention provides a compound of Formula VII:

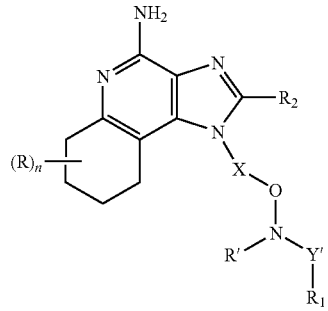

VII wherein:
X is selected from the group consisting of —CH($R_{9a}$)-alkylene- and —CH($R_{9a}$)-alkenylene-, wherein the alkylene and alkenylene are optionally interrupted by one or more —O— groups;
Y' is selected from the group consisting of:
a bond,
—C(O)—,
—C(S)—,
—S(O)$_2$—,
—S(O)$_2$—N($R_8$)—,

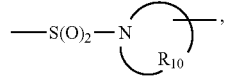

—C(O)—O—,
—C(O)—N($R_8$)—,
—C(S)—N($R_8$)—,
—C(O)—N($R_8$)—S(O)$_2$—,
—C(O)—N($R_8$)—C(O)—,
—C(S)—N($R_8$)—C(O)—,

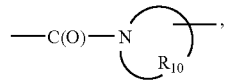

—C(O)—C(O)—,
—C(O)—C(O)—O—, and
—C(=NH)—N($R_8$)—;
each R is independently selected from the group consisting of:
halogen,
hydroxyl, alkyl,
alkenyl,
haloalkyl,
alkoxy,
alkylthio, and
—N(R$_9$)$_2$;
R$_1$ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—C(O)-alkyl, and
—C(O)-alkyl;
or R$_1$ and R' together with the nitrogen atom and Y' to which they are bonded can join to form a ring selected from the group consisting of:

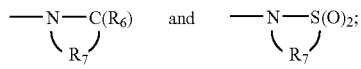

R$_2$ is selected from the group consisting of:
—R$_4$,
—X'—R$_4$,
—X'—Y—R$_4$, and
—X'—R$_5$;
X' is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—C(O)—O—,
—N(R$_8$)-Q-,
—C(R$_8$)—N(R$_8$)—,
—O—C(R$_6$)—N(R$_8$)—,
—C(R$_6$)—N(OR$_9$)—,

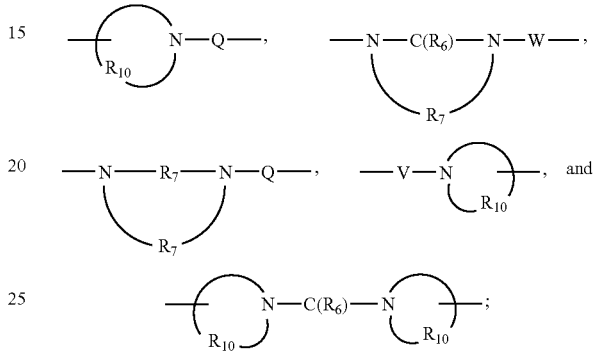

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
R$_5$ is selected from the group consisting of:

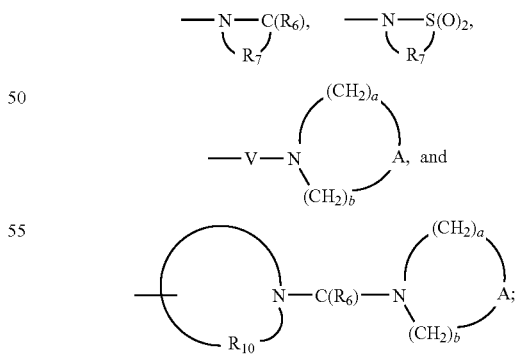

each R$_6$ is independently selected from the group consisting of =O and =S;
each R$_7$ is independently C$_{2-7}$ alkylene;
each R$_8$ is independently selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;

each $R_9$ is independently selected from the group consisting of hydrogen and alkyl;

$R_{9a}$ is selected from the group consisting of hydrogen and alkyl which is optionally interrupted by one or more —O— groups;

each $R_{10}$ is independently $C_{3-8}$ alkylene;

A is selected from the group consisting of —O—, —C(O)—, —CH$_2$—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

W is selected from the group consisting of a bond, —C(O)—, and —S(O)$_2$—;

V is selected from the group consisting of —C(R$_6$)—, —O—C(R$_6$)—, —N(R$_8$)—C(R$_6$)—, and —S(O)$_2$—;

a and b are independently integers from 1 to 6 with the proviso that a+b is ≦7; and n is an integer from 0 to 4;

or a pharmaceutically acceptable salt thereof.

In one embodiment, the present invention provides a compound of Formula VIII:

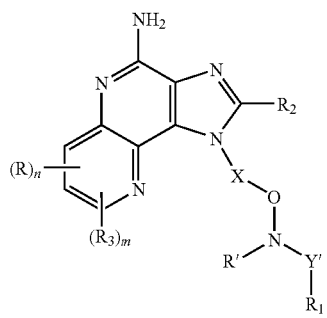

VIII wherein:

X is selected from the group consisting of —CH(R$_{9a}$)-alkylene- and —CH(R$_{9a}$)-alkenylene-, wherein the alkylene and alkenylene are optionally interrupted by one or more —O— groups;

Y' is selected from the group consisting of:

a bond,
—C(O)—,
—C(S)—,
—S(O)$_2$—,
—S(O)$_2$—N(R$_8$)—,

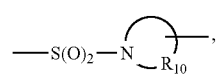

—C(O)—O—,
—C(O)—N(R$_8$)—,
—C(S)—N(R$_8$)—,
—C(O)—N(R$_8$)—S(O)$_2$—,
—C(O)—N(R$_8$)—C(O)—,
—C(S)—N(R$_8$)—C(O)—,

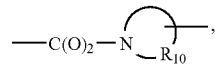

—C(O)—C(O)—,
—C(O)—C(O)—O—, and
—C(=NH)—N(R$_8$)—;

each R is independently selected from the group consisting of:
halogen,
hydroxyl,
alkyl,
alkenyl,
haloalkyl,
alkoxy,
alkylthio, and
—N(R$_9$)$_2$;

$R_1$ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—C(O)-alkyl, and
—C(O)-alkyl;

or $R_1$ and R' together with the nitrogen atom and Y' to which they are bonded can join to form a ring selected from the group consisting of:

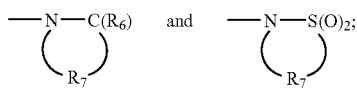

R₂ is selected from the group consisting of:
—R₄,
—X'—R₄,
—X'—Y—R₄, and
—X'—R₅;

R₃ is selected from the group consisting of:
—Z—R₄,
—Z—X'—R₄,
—Z—X'—Y—R₄, and
—Z—X'—R₅;

each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:
—S(O)₀₋₂—,
—S(O)₂—N(R₈)—,
—C(R₆)—,
—C(R₆)—O—,
—O—C(R₆)—,
—O—C(O)—O—,
—N(R₈)-Q-,
—C(R₆)—N(R₈)—,
—O—C(R₆)—N(R₈)—,
—C(R₆)—N(OR₉)—,

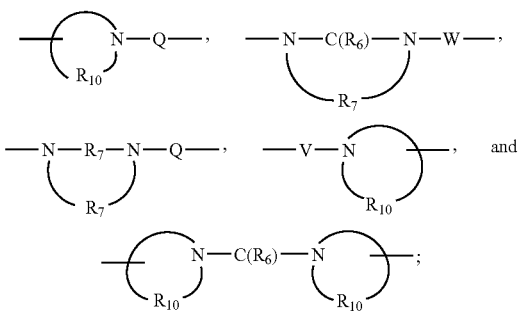

Z is a bond or —O—;

each R₄ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each R₅ is independently selected from the group consisting of:

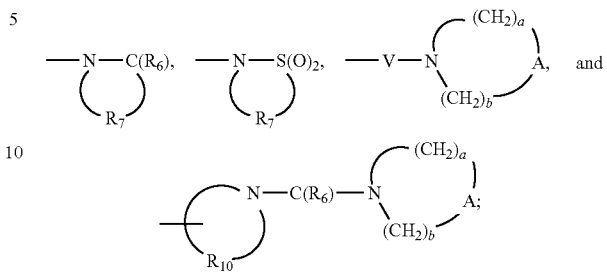

each R₆ is independently selected from the group consisting of =O and =S;

each R₇ is independently C$_{2-7}$ alkylene;

each R₈ is independently selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;

each R₉ is independently selected from the group consisting of hydrogen and alkyl;

R$_{9a}$ is selected from the group consisting of hydrogen and alkyl which is optionally interrupted by one or more —O— groups;

each R₁₀ is independently C$_{3-8}$ alkylene;

each A is independently selected from the group consisting of —O—, —C(O)—, —CH₂—, —S(O)$_{0-2}$—, and —N(R₄)—;

each Q is independently selected from the group consisting of a bond, —C(R₆)—, —C(R₆)—C(R₆)—, —S(O)₂—, —C(R₆)—N(R₈)—W—, —S(O)₂—N(R₈)—, —C(R₆)—O—, and —C(R₆)—N(OR₉)—;

each W is independently selected from the group consisting of a bond, —C(O)—, and —S(O)₂—;

each V is independently selected from the group consisting of —C(R₆)—, —O—C(R₆)—, —N(R₈)—C(R₆)—, and —S(O)₂—;

a and b are independently integers from 1 to 6 with the proviso that a+b is ≦7;

n is an integer from 0 to 3; and m is 0 or 1, with the proviso that when m is 1, n is 0 or 1;

or a pharmaceutically acceptable salt thereof.

In one embodiment, the present invention provides a compound of Formula IX.

IX

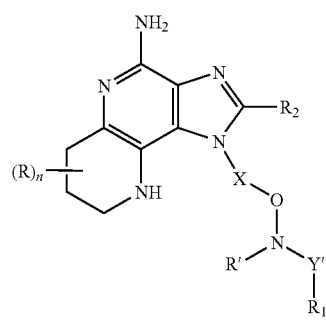

wherein:

X is selected from the group consisting of —CH(R$_{9a}$)-alkylene- and —CH(R$_{9a}$)-alkenylene-, wherein the alkylene and alkenylene are optionally interrupted by one or more —O— groups;

Y' is selected from the group consisting of:
a bond,
—C(O)—,
—C(S)—,
—S(O)$_2$—,
—S(O)$_2$—N(R$_8$)—,

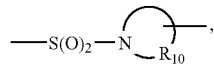

—C(O)—O—,
—C(O)—N(R$_8$)—,
—C(S)—N(R$_8$)—,
—C(O)—N(R$_8$)—S(O)$_2$—,
—C(O)—N(R$_8$)—C(O)—,
—C(S)—N(R$_8$)—C(O)—,

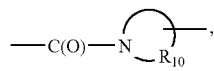

—C(O)—C(O)—,
—C(O)—C(O)—O, and
—C(=NH)—N(R$_8$)—;

each R is independently selected from the group consisting of:
halogen,
hydroxyl,
alkyl,
alkenyl,
haloalkyl,
alkoxy,
alkylthio, and
—N(R$_9$)$_2$;

R$_1$ and R' are independently selected from the group consisting of:
hydrogen,
alkyl,
alkenyl,
aryl,
arylalkylenyl,
heteroaryl,
heteroarylalkylenyl,
heterocyclyl,
heterocyclylalkylenyl, and
alkyl, alkenyl, aryl, arylalkylenyl, heteroaryl, heteroarylalkylenyl, heterocyclyl, or heterocyclylalkylenyl, substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—C(O)-alkyl, and
—C(O)-alkyl;

or R$_1$ and R' together with the nitrogen atom and Y' to which they are bonded can join to form a ring selected from the group consisting of:

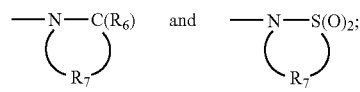

R$_2$ is selected from the group consisting of:
—R$_4$,
—X'—R$_4$,
—X'—Y—R$_4$, and
—X'—R$_5$;

X' is selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

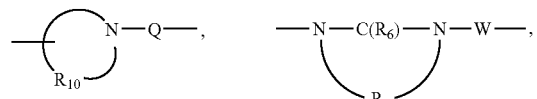

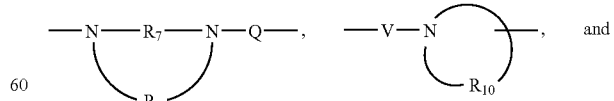

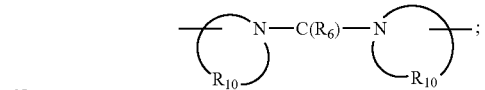

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

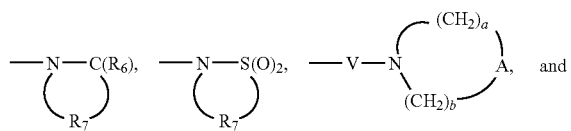

each R$_6$ is independently selected from the group consisting of =O and =S;

each R$_7$ is independently C$_{2-7}$ alkylene;

each R$_8$ is independently selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;

each R$_9$ is independently selected from the group consisting of hydrogen and alkyl;

R$_{9a}$ is selected from the group consisting of hydrogen and alkyl which is optionally interrupted by one or more —O— groups;

each R$_{10}$ is independently C$_{3-8}$ alkylene;

A is selected from the group consisting of —O—, —C(O)—, —CH$_2$—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

W is selected from the group consisting of a bond, —C(O)—, and —S(O)$_2$—;

V is selected from the group consisting of —C(R$_6$)—, —O—C(R$_6$)—, —N(R$_8$)—C(R$_6$)—, and —S(O)$_2$—;

a and b are independently integers from 1 to 6 with the proviso that a+b is ≦7; and n is an integer from 0 to 3;

or a pharmaceutically acceptable salt thereof.

In one embodiment, the present invention provides a compound of Formula X:

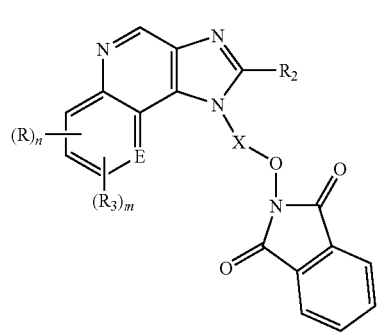

wherein:

E is selected from the group consisting of CH, CR, CR$_3$, and N, with the proviso that when E is CR$_3$, m is 0, and n is 0 or 1, and with the further proviso that when E is CR and m is 1, n is 0;

X is selected from the group consisting of —CH(R$_{9a}$)-alkylene- and —CH(R$_{9a}$)-alkenylene-, wherein the alkylene and alkenylene are optionally interrupted by one or more —O— groups;

each R is independently selected from the group consisting of:
 halogen,
 hydroxyl,
 alkyl,
 alkenyl,
 haloalkyl,
 alkoxy,
 alkylthio, and
 —N(R$_9$)$_2$;

R$_2$ is selected from the group consisting of:
 —R$_4$,
 —X'—R$_4$,
 —X'—Y—R$_4$, and
 —X'—R$_5$;

R$_3$ is selected from the group consisting of:
 —Z—R$_4$,
 —Z—X'—R$_4$,
 —Z—X'—Y—R$_4$, and
 —Z—X'—R$_5$;

each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:
 —S(O)$_{0-2}$—,
 —S(O)$_2$—N(R$_8$)—,
 —C(R$_6$)—,
 —C(R$_6$)—O—,
 —O—C(R$_6$)—,
 —O—C(O)—O—,

—N($R_8$)-Q-,
—C($R_6$)—N($R_8$)—,
—O—C($R_6$)—N($R_8$)—,
—C($R_6$)—N(O$R_9$)—,

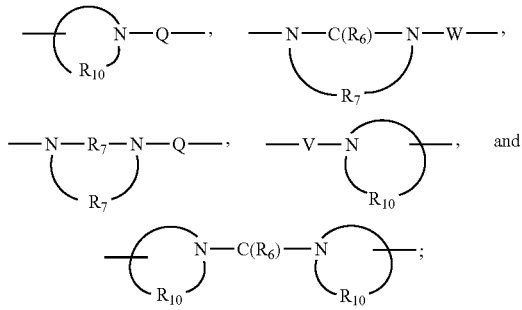

Z is a bond or —O—;

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each $R_5$ is independently selected from the group consisting of:

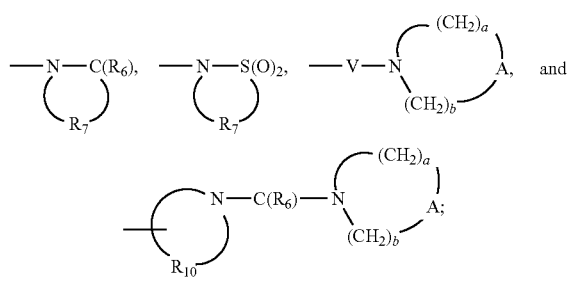

each $R_6$ is independently selected from the group consisting of =O and =S;

each $R_7$ is independently $C_{2-7}$ alkylene;

each $R_8$ is independently selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl;

each $R_9$ is independently selected from the group consisting of hydrogen and alkyl;

$R_{9a}$ is selected from the group consisting of hydrogen and alkyl which is optionally interrupted by one or more —O— groups;

each $R_{10}$ is independently $C_{3-8}$ alkylene;

each A is independently selected from the group consisting of —O—, —C(O)—, —CH$_2$—, —S(O)$_{0-2}$—, and —N($R_4$)—;

each Q is independently selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;

each W is independently selected from the group consisting of a bond, —C(O)—, and —S(O)$_2$—;

each V is independently selected from the group consisting of —C($R_6$)—, —O—C($R_6$)—, —N($R_8$)—C($R_6$)—, and —S(O)$_2$—;

a and b are independently integers from 1 to 6 with the proviso that a+b is ≤7;

n is an integer from 0 to 3; and m is 0 or 1, with the proviso that when m is 1, n is 0 or 1;

or a pharmaceutically acceptable salt thereof.

In one embodiment, the present invention provides a compound of Formula XI:

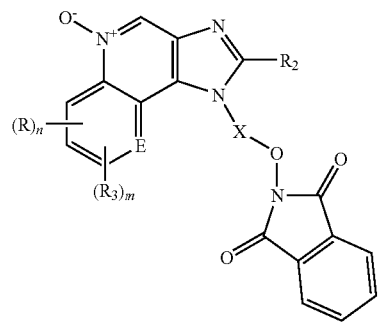

XI wherein:

E is selected from the group consisting of CH, CR, CR$_3$, and N, with the proviso that when E is CR$_3$, m is 0, and n is 0 or 1, and with the further proviso that when E is CR and m is 1, n is 0;

X is selected from the group consisting of —CH(R$_{9a}$)-alkylene- and —CH(R$_{9a}$)-alkenylene-, wherein the alkylene and alkenylene are optionally interrupted by one or more —O— groups;

each R is independently selected from the group consisting of:
halogen,
hydroxyl,
alkyl,
alkenyl,
haloalkyl,
alkoxy,
alkylthio, and
—N(R$_9$)$_2$;

R$_2$ is selected from the group consisting of:
—R$_4$,
—X'—R$_4$,
—X'—Y—R$_4$, and
—X'—R$_5$;

R$_3$ is selected from the group consisting of:
—Z—R$_4$,
—Z—X'—R$_4$,
—Z—X'—Y—R$_4$, and
—Z—X'—R$_5$;

each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

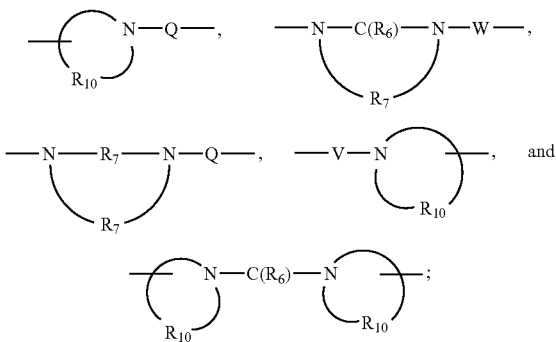

Z is a bond or —O—;

each R$_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each R$_5$ is independently selected from the group consisting of:

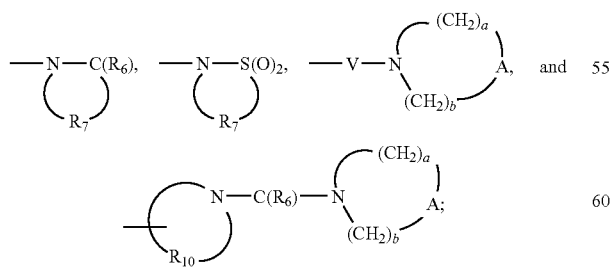

each R$_6$ is independently selected from the group consisting of =O and =S;

each R$_7$ is independently C$_{2-7}$ alkylene;

each R$_8$ is independently selected from the group consisting of hydrogen, C$_{1-10}$ alkyl, C$_{2-10}$ alkenyl, C$_{1-10}$ alkoxy-C$_{1-10}$ alkylenyl, and aryl-C$_{1-10}$ alkylenyl;

each R$_9$ is independently selected from the group consisting of hydrogen and alkyl;

R$_{9a}$ is selected from the group consisting of hydrogen and alkyl which is optionally interrupted by one or more —O— groups;

each R$_{10}$ is independently C$_{3-8}$ alkylene;

each A is independently selected from the group consisting of —O—, —C(O)—, —CH$_2$—, —S(O)$_{0-2}$—, and —N(R$_4$)—;

each Q is independently selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

each W is independently selected from the group consisting of a bond, —C(O)—, and —S(O)$_2$—;

each V is independently selected from the group consisting of —C(R$_6$)—, —O—C(R$_6$)—, —N(R$_8$)—C(R$_6$)—, and —S(O)$_2$—;

a and b are independently integers from 1 to 6 with the proviso that a+b is ≦7;

n is an integer from 0 to 3; and m is 0 or 1, with the proviso that when m is 1, n is 0 or 1;

or a pharmaceutically acceptable salt thereof.

In one embodiment, the present invention provides a compound of Formula XII:

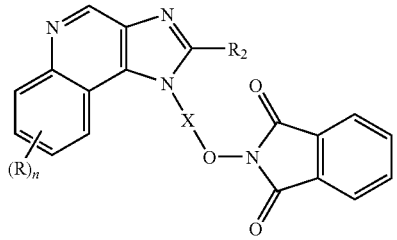

XII wherein:

X is selected from the group consisting of —CH(R$_{9a}$)-alkylene- and —CH(R$_{9a}$)-alkenylene-;

each R is independently selected from the group consisting of alkyl, alkoxy, halogen, hydroxyl, and trifluoromethyl;

R$_2$ is selected from the group consisting of:
hydrogen,
alkyl,
alkenyl,
aryl,
heteroaryl,
heterocyclyl,
alkylene-Y"-alkyl,
alkylene-Y"-alkenyl,
alkylene-Y"-aryl, and
alkyl or alkenyl substituted by one or more substituents selected from the group consisting of:
hydroxyl,
halogen,
—N(R$_{8a}$)$_2$,
—C(O)—C$_{1-10}$ alkyl,
—C(O)—O—C$_{1-10}$ alkyl,
—N$_3$,
aryl, heteroaryl,
heterocyclyl,
—C(O)-aryl, and
—C(O)-heteroaryl;
Y" is —O— or —S(O)$_{0-2}$—;
each R$_{8a}$ is independently selected from the group consisting of hydrogen, C$_{1-10}$ alkyl, and C$_{2-10}$ alkenyl;
R$_{9a}$ is selected from the group consisting of hydrogen and alkyl which may be optionally interrupted by one or more —O— groups; and
n is an integer from 0 to 4;

or a pharmaceutically acceptable salt thereof.

In one embodiment, the present invention provides a compound of Formula XIII:

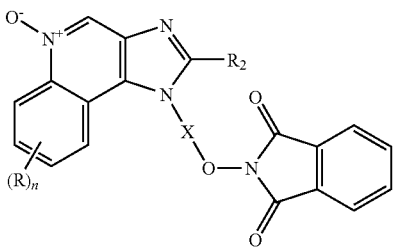

XIII wherein:
X is selected from the group consisting of —CH(R$_{9a}$)-alkylene- and —CH(R$_{9a}$)-alkenylene-;
each R is independently selected from the group consisting of alkyl, alkoxy, halogen, hydroxyl, and trifluoromethyl;
R$_2$ is selected from the group consisting of:
hydrogen,
alkyl,
alkenyl,
aryl,
heteroaryl,
heterocyclyl,
alkylene-Y"-alkyl,
alkylene-Y"-alkenyl,
alkylene-Y"-aryl, and
alkyl or alkenyl substituted by one or more substituents selected from the group consisting of:
hydroxyl,
halogen,
—N(R$_{8a}$)$_2$,
—C(O)—C$_{1-10}$ alkyl,
—C(O)—O—C$_{1-10}$ alkyl,
—N$_3$,
aryl,
heteroaryl,
heterocyclyl,
—C(O)-aryl, and
—C(O)-heteroaryl;
Y" is —O— or —S(O)$_{0-2}$—;
each R$_{8a}$ is independently selected from the group consisting of hydrogen, C$_{1-10}$ alkyl, and C$_{2-10}$ alkenyl;
R$_{9a}$ is selected from the group consisting of hydrogen and alkyl which may be optionally interrupted by one or more —O— groups; and
n is an integer from 0 to 4;

or a pharmaceutically acceptable salt thereof.

In one embodiment, the present invention provides a compound of Formula XIV:

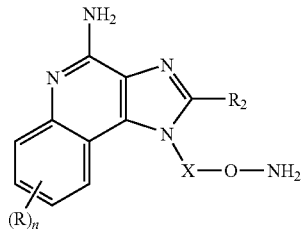

XIV wherein:
X is selected from the group consisting of —CH(R$_{9a}$)-alkylene- and —CH(R$_{9a}$)-alkenylene-;
each R is independently selected from the group consisting of alkyl, alkoxy, halogen, hydroxyl, and trifluoromethyl;
R$_2$ is selected from the group consisting of:
hydrogen,
alkyl,
alkenyl,
aryl,
heteroaryl,
heterocyclyl,
alkylene-Y"-alkyl,
alkylene-Y"-alkenyl,
alkylene-Y"-aryl, and
alkyl or alkenyl substituted by one or more substituents selected from the group consisting of:
hydroxyl,
halogen,
—N(R$_{8a}$)$_2$,
—C(O)—C$_{1-10}$ alkyl,
—C(O)—O—C$_{1-10}$ alkyl,
—N$_3$,
aryl,
heteroaryl,
heterocyclyl,
—C(O)-aryl, and
—C(O)-heteroaryl,
Y" is —O— or —S(O)$_{0-2}$—;
each R$_{8a}$ is independently selected from the group consisting of hydrogen, C$_{1-10}$ alkyl, and C$_{2-10}$ alkenyl;
R$_{9a}$ is selected from the group consisting of hydrogen and alkyl which may be optionally interrupted by one or more —O— groups; and
n is an integer from 0 to 4;

or a pharmaceutically acceptable salt thereof.

For any of the compounds presented herein, each one of the following variables (e.g., R, R', R", R'", R$_1$, R$_2$, R$_3$, m, n, A, and so on) in any of its embodiments can be combined with any one or more of the other variables in any of their embodiments as would be understood by one of skill in the art. Each of the resulting combinations of variables is an embodiment of the present invention.

For certain embodiments, each of R, R", and R'" is independently a non-interfering substituent. For certain embodiments, each R and R" is independently selected from the group consisting of hydrogen and non-interfering substituents. Herein, "non-interfering" means that the immunomodulator activity of the compound is not destroyed.

For certain embodiments, each R is independently selected from the group consisting of: halogen, hydroxyl, alkyl, alkenyl, haloalkyl, alkoxy, alkylthio, and —N($R_9$)$_2$. For certain embodiments, each R is independently selected from the group consisting of alkyl, alkoxy, halogen, hydroxyl, and trifluoromethyl.

For certain embodiments, $R_1$ and R' are independently selected from the group consisting of: hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, or heterocyclylalkylenyl, substituted by one or more substituents selected from the group consisting of: hydroxyl, alkyl, haloalkyl, hydroxyalkyl, alkoxy, dialkylamino, —S(O)$_{0-2}$-alkyl, —S(O)$_{0-2}$-aryl, —NH—S(O)$_2$-alkyl, —NH—S(O)$_2$-aryl, haloalkoxy, halogen, nitrile, nitro, aryl, heteroaryl, heterocyclyl, aryloxy, arylalkyleneoxy, —C(O)—O-alkyl, —C(O)—N($R_8$)$_2$, —N($R_8$)—C(O)-alkyl, —O—C(O)-alkyl, and —C(O)-alkyl.

For certain embodiments, $R_1$ and R' join together to form a ring system. The size and components of the ring system are not limiting as long as they do not destroy the immunomodulator activity of the compound (i.e., they are non-interfering). For certain embodiments, preferably, $R_1$ and R' together with the nitrogen atom and Y' to which they are bonded can join to form a ring selected from the group consisting of:

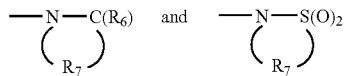

For certain embodiments, R' is selected from the group consisting of hydrogen and $C_{1-4}$ alkyl. For certain embodiments, R' is hydrogen.

For certain embodiments, $R_1$ is selected from the group consisting of: hydrogen, alkyl, alkenyl, aryl, alkylene-aryl, alkylene-heteroaryl, alkylene-heterocyclyl, heteroaryl, heterocyclyl, and alkyl, alkenyl, aryl, arylalkylenyl, heteroarylalkylenyl, heterocyclylalkylenyl, heteroaryl or heterocyclyl, substituted by one or more substituents selected from the group consisting of: hydroxyl, alkyl, haloalkyl, hydroxyalkyl, —O-alkyl, —S(O)$_{0-2}$-alkyl, —S(O)$_{0-2}$-aryl, —O-haloalkyl, halogen, nitrile, nitro, aryl, heteroaryl, heterocyclyl, —O-aryl, —O-alkylene-aryl, —C(O)—O-alkyl, —C(O)—N($R_{8a}$)$_2$, —N($R_{8a}$)—C(O)-alkyl, —O—C(O)-alkyl, and —C(O)-alkyl.

For certain embodiments, $R_1$ is selected from the group consisting of alkyl, alkenyl, aryl, and heteroaryl, each of which is optionally substituted by one or more substituents selected from the group consisting of —O-alkyl, —O-aryl, —S-alkyl, —S-aryl, halogen, —O—C(O)-alkyl, —C(O)—O-alkyl, haloalkoxy, haloalkyl, and aryl. For certain embodiments, $R_1$ is selected from the group consisting of alkyl and aryl, each of which is optionally substituted by one or more substituents selected from the group consisting of —O-alkyl, —O-aryl, —S-alkyl, —S-aryl, halogen, —O—C(O)-alkyl, —C(O)—O-alkyl, haloalkoxy, haloalkyl, and aryl.

For certain embodiments $R_1$ is hydrogen. For certain embodiments, $R_1$ is $C_{1-6}$ alkyl or aryl $C_{1-6}$ alkylenyl. For certain embodiments, $R_1$ is selected from the group consisting of $C_{1-6}$ alkyl and pyridyl.

For certain embodiments R' is selected from the group consisting of hydrogen and $C_{1-4}$ alkyl, and $R_1$ is $C_{1-6}$ alkyl or aryl $C_{1-6}$ alkylenyl. For such embodiments, preferably, Y' is a bond.

For certain embodiments, R' and $R_1$ are each hydrogen. For such embodiments, preferably, Y' is a bond.

For certain embodiments, when Y' is —C(O)—, —S(O)$_2$—, or —C(O)—N($R_8$)—, $R_1$ is selected from the group consisting of alkyl, alkenyl, aryl, and heteroaryl, each of which is optionally substituted by one or more substituents selected from the group consisting of —O-alkyl, —S-alkyl, —S-aryl, halogen, —C(O)-alkyl, —C(O)—O-alkyl, haloalkoxy, haloalkyl, and aryl. For such embodiments, preferably, $R_1$ is selected from the group consisting of $C_{1-6}$ alkyl and pyridyl.

For certain embodiments, R" is hydrogen or a non-interfering substituent. For certain embodiments, R" is selected from the group consisting of: —$R_4$, —X'—$R_4$, —X'—Y—$R_4$, and —X'—$R_5$. For certain embodiments, R" is hydrogen, alkoxyalkylenyl, —$R_4$, —X'—$R_4$, or —X'—Y—$R_4$. For certain of these embodiments, preferably, X' is $C_{1-2}$ alkylene; Y is —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, or —C($R_6$)—N(O$R_9$)—; and $R_4$ is alkyl.

For certain embodiments, R" is selected from the group consisting of: hydrogen, alkyl, alkenyl, aryl, heteroaryl, heterocyclyl, alkylene-Y"-alkyl, alkylene-Y"-alkenyl, alkylene-Y"-aryl, and alkyl or alkenyl substituted by one or more substituents selected from the group consisting of: hydroxyl, halogen, —N($R_{8a}$)$_2$, —C(O)—$C_{1-10}$ alkyl, —C(O)—O—$C_{1-10}$ alkyl, —$N_3$, aryl, heteroaryl, heterocyclyl, —C(O)-aryl, and —C(O)-heteroaryl. For these embodiments, Y" is —O— or —S(O)$_{0-2}$—.

For certain embodiments, R" is selected from the group consisting of hydrogen, alkyl, and alkoxyalkylenyl (i.e., alkylene-O-alkyl). For certain embodiments, R" is selected from the group consisting of hydrogen, methyl, ethyl, propyl, butyl, ethoxymethyl, 2-methoxyethyl, and methoxymethyl.

For certain embodiments, $R_2$ is selected from the group consisting of: —$R_4$, —X'—$R_4$, —X'—Y—$R_4$, and —X'—$R_5$. For certain embodiments, $R_2$ is hydrogen, alkoxyalkylenyl, —$R_4$, —X'—$R_4$, or —X'—Y—$R_4$. For certain of these embodiments, preferably, X' is $C_{1-2}$ alkylene; Y is —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, or —C($R_6$)—N(O$R_9$)—; and $R_4$ is alkyl.

For certain embodiments, $R_2$ is selected from the group consisting of: hydrogen, alkyl, alkenyl, aryl, heteroaryl, heterocyclyl, alkylene-Y"-alkyl, alkylene-Y"-alkenyl, alkylene-Y"-aryl, and alkyl or alkenyl substituted by one or more substituents selected from the group consisting of: hydroxyl, halogen, —N($R_{8a}$)$_2$, —C(O)—$C_{1-10}$ alkyl, —C(O)—O—$C_{1-10}$ alkyl, —$N_3$, aryl, heteroaryl, heterocyclyl, —C(O)-aryl, and —C(O)-heteroaryl. For these embodiments, Y" is —O— or —S(O)$_{0-2}$—.

For certain embodiments, $R_2$ is selected from the group consisting of hydrogen, alkyl, and alkoxyalkylenyl (i.e., alkylene-O-alkyl). For certain embodiments, $R_2$ is selected from the group consisting of hydrogen, methyl, ethyl, propyl, butyl, ethoxymethyl, 2-methoxyethyl, and methoxymethyl.

For certain embodiments, $R_3$ is selected from the group consisting of: —Z—$R_4$, —Z—X'—$R_4$, —Z—X'-Y—$R_4$, and —Z—X'—$R_5$. For certain embodiments, $R_3$ is phenyl, pyridin-3-yl, pyridin-4-yl, 5-(hydroxymethyl)pyridin-3-yl, 2-ethoxyphenyl, 3-(morpholine-4-carbonyl)phenyl, or 3-(N,N-dimethylaminocarbonyl)phenyl. For certain of these embodiments, m is 1.

For certain embodiments, each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo. For certain embodiments, $R_4$ is alkyl.

For certain embodiments, each $R_5$ is independently selected from the group consisting of:

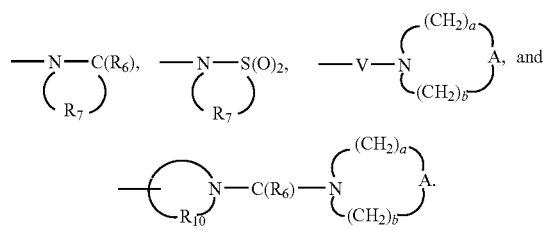

For certain embodiments, each $R_6$ is independently selected from the group consisting of =O and =S.

For certain embodiments, each $R_7$ is independently $C_{2-7}$ alkylene.

For certain embodiments, each $R_8$ is independently selected from the group consisting of hydrogen, $C_{1-10}$ alkyl, $C_{2-10}$ alkenyl, $C_{1-10}$ alkoxy-$C_{1-10}$ alkylenyl, and aryl-$C_{1-10}$ alkylenyl.

For certain embodiments, each $R_{8a}$ is independently selected from the group consisting of hydrogen, $C_{1-10}$ alkyl, and $C_{2-10}$ alkenyl.

For certain embodiments, each $R_9$ is independently selected from the group consisting of hydrogen and alkyl.

For certain embodiments, $R_{9a}$ is selected from the group consisting of hydrogen and alkyl which is optionally interrupted by one or more —O— groups.

For certain embodiments, each $R_{10}$ is independently $C_{3-8}$ alkylene.

For certain embodiments, $R_A$ and $R_B$ are each independently selected from the group consisting of: hydrogen, halogen, alkyl, alkenyl, alkoxy, alkylthio, and —N($R_9$)$_2$; or when taken together, $R_A$ and $R_B$ form a fused aryl ring or heteroaryl ring containing one heteroatom selected from the group consisting of N and S, wherein the aryl or heteroaryl ring is unsubstituted or substituted by one or more R''' groups; or when taken together, $R_A$ and $R_B$ form a fused 5 to 7 membered saturated ring, optionally containing one heteroatom selected from the group consisting of N and S, and unsubstituted or substituted by one or more R groups.

For certain embodiments, $R_A$ and $R_B$ are each independently selected from the group consisting of: hydrogen, halogen, alkyl, alkenyl, alkoxy, alkylthio, and —N($R_9$)$_2$; or when taken together, $R_A$ and $R_B$ form a fused aryl ring or heteroaryl ring containing one heteroatom selected from the group consisting of N and S, wherein the aryl or heteroaryl ring is unsubstituted or substituted by one or more R groups, or substituted by one $R_3$ group, or substituted by one $R_3$ group and one R group; or when taken together, $R_A$ and $R_B$ form a fused 5 to 7 membered saturated ring, optionally containing one heteroatom selected from the group consisting of N and S, and unsubstituted or substituted by one or more R groups.

In certain of these embodiments the fused aryl ring is a benzene ring. In certain of these embodiments the heteroaryl ring is a pyridine ring. In certain of these embodiments the saturated ring is a cyclohexane ring. In certain of these embodiments the saturated ring is a piperidine ring.

For certain embodiments, $R_A$ and $R_B$ form a fused aryl ring or heteroaryl ring containing one N, wherein the aryl ring or heteroaryl ring is unsubstituted. In certain of these embodiments the fused aryl ring is a benzene ring. In certain of these embodiments the heteroaryl ring is a pyridine ring. For certain embodiments, $R_A$ and $R_B$ form a fused 5 to 7 membered saturated ring, optionally containing one N, wherein the saturated ring is unsubstituted. In certain of these embodiments the saturated ring is a cyclohexane ring. In certain of these embodiments the saturated ring is a piperidine ring.

For certain embodiments, $R_{A1}$ and $R_{B1}$ are each independently selected from the group consisting of: hydrogen, halogen, alkyl, alkenyl, alkoxy, alkylthio, and —N($R_9$)$_2$. For certain embodiments, $R_{A1}$ and $R_{B1}$ are each methyl.

For certain embodiments, each A is independently selected from the group consisting of —O—, —C(O)—, —CH$_2$—, —S(O)$_{0-2}$—, and —N($R_4$)—.

For certain embodiments, E is selected from the group consisting of CH, CR, CR$_3$, and N. In certain embodiments, when E is CR$_3$, then m is 0 and n is 0 or 1. In certain embodiments, when E is CR and m is 1, n is 0. Preferably, E is CH or N.

For certain embodiments, each Q is independently selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—. For certain embodiments, Q is a bond or —C(O)—.

For certain embodiments, each V is independently selected from the group consisting of —C($R_6$)—, —O—C($R_6$)—, —N($R_8$)—C($R_6$)—, and —S(O)$_2$—.

For certain embodiments, each W is independently selected from the group consisting of a bond, —C(O)—, and —S(O)$_2$—.

For certain embodiments, X is selected from the group consisting of —CH($R_{9a}$)-alkylene- and —CH($R_{9a}$)-alkenylene-, wherein the alkylene and alkenylene are optionally interrupted by one or more —O— groups. For certain embodiments, X is selected from the group consisting of —CH($R_{9a}$)-alkylene- and —CH($R_{9a}$)-alkenylene-. For certain embodiments, X is —CH($R_{9a}$)-alkylene-, wherein the alkylene is optionally interrupted by one or more —O— groups. For certain embodiments, X is —C$_{3-5}$ alkylene- or —CH$_2$CH$_2$OCH$_2$CH$_2$—. For certain embodiments, X is —CH($R_{9a}$)—C$_{1-10}$ alkylene- and for other embodiments X is propylene or butylene.

For certain embodiments, each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups. For certain embodiments, each X' is independently $C_{1-2}$ alkylene.

For certain embodiments, each Y is independently selected from the group consisting of: —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N(O$R_9$)—,

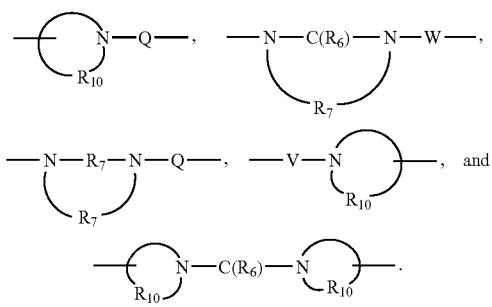

For certain embodiments, each Y is independently —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, or —C(R$_6$)—N(OR$_9$)—.

For certain embodiments, Y' is selected from the group consisting of: a bond, —C(O)—, —C(S)—, —S(O)$_2$—, —S(O)$_2$—N(R$_8$)—,

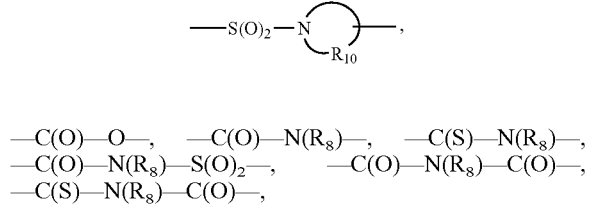

—C(O)—O—, —C(O)—N(R$_8$)—, —C(S)—N(R$_8$)—, —C(O)—N(R$_8$)—S(O)$_2$—, —C(O)—N(R$_8$)—C(O)—, —C(S)—N(R$_8$)—C(O)—,

—C(O)—C(O)—, —C(O)—C(O)—O—, and —C(=NH)—N(R$_8$)—.

For certain embodiments, Y' is selected from the group consisting of: a bond, —C(O)—, —C(S)—, —S(O)$_2$—, —S(O)$_2$—N(R$_{8a}$)—, —C(O)—O—, —C(O)—N(R$_{8a}$)—, —C(S)—N(R$_{8a}$)—, —C(O)—N(R$_{8a}$)—S(O)$_2$—, —C(O)—N(R$_{8a}$)—C(O)—, —C(S)—N(R$_{8a}$)—C(O)—, and —C(O)—C(O)—O—.

For certain embodiments, Y' is —C(O)—, —S(O)$_2$—, or —C(O)—N(R$_{8a}$)—. For certain embodiments, Y' is a bond.

For certain embodiments, Y" is —O— or —S(O)$_{0-2}$—.

For certain embodiments, Z is a bond or —O—. Preferably, Z is a bond.

For certain embodiments, n is an integer from 0 to 4. For certain embodiments, n is an integer from 0 to 3. For certain embodiments, n is 0 or 1. For certain embodiments, n is 0.

For certain embodiments, m is 0 or 1. For certain embodiments, m is 1.

For certain embodiments, when m is 1, n is 0 or 1.

For certain embodiments, when m is 0, n is 0 or 1.

For certain embodiments, m and n are each 0.

For certain embodiments, a and b are independently integers from 1 to 6 with the proviso that a+b is ≦7.

As used herein, the terms "alkyl", "alkenyl", "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "-alkylene-", "alkenylene", "-alkenylene-", "alkynylene", and "-alkynylene-" are the divalent forms of the "alkyl", "alkenyl", and "alkynyl" groups defined above. The terms "alkylenyl", "alkenylenyl", and "alkynylenyl" are used when "alkylene", "alkenylene", and "alkynylene", respectively, are substituted. For example, an arylalkylenyl group comprises an "alkylene" moiety to which an aryl group is attached.

The term "haloalkyl" is inclusive of alkyl groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

The term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl, homopiperazinyl, and the like.

The terms "arylene", "heteroarylene", and "heterocyclylene" are the divalent forms of the "aryl", "heteroaryl", and "heterocyclyl" groups defined above. The terms "arylenyl," "heteroarylenyl," and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N(R$_9$)$_2$ each R$_9$ group is independently selected. In another example, when an R$_2$ and an R$_3$ group both contain an R$_4$ group, each R$_4$ group is independently selected. In a further example, when more than one Y group is present (i.e., R$_2$ and R$_3$ both contain a Y group) and each Y group contains one or more R$_9$ groups, then each Y group is independently selected, and each R$_8$ group is independently selected.

The invention is inclusive of the compounds described herein and salts thereof in any of their pharmaceutically acceptable forms, including isomers such as diastereomers and enantiomers, solvates, polymorphs, and the like. In particular, if a compound is optically active, the invention specifically includes each of the compound's enantiomers as well as racemic mixtures of the enantiomers.

Preparation of the Compounds

Compounds of the invention can be prepared according to Reaction Scheme I where R, $R_1$, $R_2$, m, Y' and X are as defined above; $R'_a$ is a subset of R' that does not include substituted or unsubstituted aryl or heteroaryl groups; E' is carbon (imidazoquinoline ring) or nitrogen (imidazonaphthyridine ring); n is an integer from 0 to 4 (imidazoquinoline ring) or 0 to 3 (imidazonaphthyridine ring) with the proviso that when m is 1, n is 0 or 1; and D is —Br, —I, or —OCH$_2$Ph; wherein Ph is phenyl. In step (1) of Reaction Scheme I, an aniline or aminopyridine of Formula XV is treated with the condensation product generated from 2,2-dimethyl-1,3-dioxane-4,6-dione (Meldrum's acid) and triethyl orthoformate to provide an imine of Formula XVI. The reaction is conveniently carried out by adding a solution of an aniline or aminopyridine of Formula XV to a heated mixture of Meldrum's acid and triethyl orthoformate and heating the reaction at an elevated temperature. The product can be isolated using conventional methods. Many anilines and aminopyridines of Formula XV are commercially available; others can be prepared by known synthetic methods. For example, benzyloxypyridines of Formula XV can be prepared using the method of Holladay et al., *Biorg. Med. Chem. Lett.*, 8, pp. 2797-2802, (1998).

In step (2) of Reaction Scheme I, an imine of Formula XVI undergoes thermolysis and cyclization to provide a compound of Formula XVII. The reaction is conveniently carried out in a medium such as DOWTHERM A heat transfer fluid at a temperature between 200 and 250° C. The product can be isolated using conventional methods.

In step (3) of Reaction Scheme I, a compound of Formula XVII is nitrated under conventional nitration conditions to provide a compound of Formula XVIII. The reaction is conveniently carried out by adding nitric acid to the compound of Formula XVII in a suitable solvent such as propionic acid and heating the mixture at an elevated temperature. The product can be isolated using conventional methods.

In step (4) of Reaction Scheme I, a 3-nitro[1,5]naphthyridin-4-ol or 3-nitroquinolin-4-ol of Formula XVIII is chlorinated using conventional chlorination chemistry to provide a 4-chloro-3-nitro[1,5]naphthyridine or 4-chloro-3-nitroquinoline of Formula XIX. The reaction is conveniently carried out by treating the compound of Formula XVIII with phosphorous oxychloride in a suitable solvent such as N,N-dimethylformamide (DMF). The reaction can be carried out at ambient temperature or at an elevated temperature such as 100° C., and the product can be isolated using conventional methods.

In step (5) of Reaction Scheme I, a 4-chloro-3-nitro[1,5]naphthyridine or 4-chloro-3-nitroquinoline of Formula XIX is treated with an amine of Formula HO—X—NH$_2$ to provide a compound of Formula XX. Several amines of Formula HO—X—NH$_2$ are commercially available; others can be prepared by known synthetic methods. The reaction is conveniently carried out by adding the amine of Formula HO—X—NH$_2$ to a solution of the 4-chloro-3-nitro[1,5]naphthyridine or 4-chloro-3-nitroquinoline of Formula XIX in a suitable solvent such as dichloromethane in the presence of a tertiary amine such as triethylamine. The reaction can be carried out at ambient temperature or at a sub-ambient temperature such as, for example, 0° C. The reaction product can be isolated using conventional methods.

In step (6) of Reaction Scheme I, a compound of Formula XX is reduced to provide a diamine of Formula XXI. The reaction can be carried out by hydrogenation using a heterogeneous hydrogenation catalyst such as palladium on carbon or platinum on carbon. The hydrogenation is conveniently carried out in a Parr apparatus in a suitable solvent such as toluene, methanol, acetonitrile, or ethyl acetate. The reaction can be carried out at ambient temperature, and the product can be isolated using conventional methods.

Alternatively, the reduction in step (6) can be carried out using a one- or two-phase sodium dithionite reduction. The reaction is conveniently carried out using the conditions described by Park, K. K.; Oh, C. H.; and Joung, W. K.; *Tetrahedron Lett.*, 34, pp. 7445-7446 (1993) by adding sodium dithionite to a compound of Formula XX in a mixture of dichloromethane and water at ambient temperature in the presence of potassium carbonate and ethyl viologen dibromide, ethyl viologen diiodide, or 1,1'-di-n-octyl-4,4'-bipyridinium dibromide. The product can be isolated using conventional methods.

In step (7) of Reaction Scheme I, a diamine of Formula XXI, is reacted with a carboxylic acid equivalent to provide a 1H-imidazo[4,5-c][1,5]naphthyridine or 1H-imidazo[4,5-c]quinoline of Formula XXII. Suitable carboxylic acid equivalents include orthoesters of Formula $R_2$C(O-alkyl)$_3$,1,1-dialkoxyalkyl alkanoates of Formula $R_2$C(O-alkyl)$_2$(O—C(O)-alkyl), and acid chlorides of Formula $R_2$C(O)Cl. The selection of the carboxylic acid equivalent is determined by the desired substituent at $R_2$. For example, triethyl orthoformate will provide a compound where $R_2$ is hydrogen, and trimethyl orthobutyrate will provide a compound where $R_2$ is a propyl group. Step (7) is conveniently carried out by adding the carboxylic acid equivalent to a diamine of Formula XXI in a suitable solvent such as toluene or xylenes. Optionally, catalytic pyridine hydrochloride can be added. The reaction is carried out at a temperature high enough to drive off alcohol or water formed during the reaction. Conveniently, a Dean-Stark trap can be used to collect the volatiles. The 1H-imidazo[4,5-c][1,5]naphthyridine or 1H-imidazo[4,5-c]quinoline product of Formula XXII can be isolated and optionally purified using conventional techniques.

Alternatively, step (7) of Reaction Scheme I can be carried out in two steps when an acid chloride of Formula $R_2$C(O)Cl is used as the carboxylic acid equivalent. Part (i) of step (7) is conveniently carried out by adding the acid chloride to a solution of a diamine of Formula XXI in a suitable solvent such as dichloromethane or acetonitrile. Optionally, a tertiary amine such as triethylamine, pyridine, or 4-dimethylaminopyridine can be added. The reaction can be carried out at ambient temperature. The amide product can be isolated and optionally purified using conventional techniques. Part (ii) of step (7) involves heating the amide prepared in part (i) in the presence of base to provide a 1H-imidazo[4,5-c][1,5]naphthyridine or 1H-imidazo[4,5-c]quinoline of Formula XXII. The reaction is conveniently carried out in a suitable solvent such as ethanol in the presence of a base such aqueous sodium hydroxide or aqueous potassium carbonate at elevated temperature. The product of Formula XXII can be isolated using conventional methods.

In an alternative route to a compound of Formula XXII, the alcohol group in a compound of Formula XX is first protected with an appropriate protecting group such as an acetyl group. The protection reaction is conveniently carried out by adding acetic anhydride to a solution of a compound of Formula XX in a suitable solvent such as dichloromethane in the presence of a tertiary amine such as triethylamine optionally with 4-dimethylaminopyridine as a catalyst. The reaction is carried out at sub-ambient temperature such as, for example, 0° C. The reaction product can be isolated using conventional methods and is then subjected to the conditions described in steps (6) and (7) of Reaction Scheme I. If the two-step procedure employing an acid chloride as the carboxylic acid equivalent is used in step (7), the acetyl protecting group is cleaved under the conditions described in part (ii) of step (7) to afford a compound of the Formula XXII. If the carboxylic acid equivalent is introduced using the one-step procedure described in step (7), the acetyl protecting group can be cleaved in a subsequent reaction to afford a compound of the Formula XXII. Cleavage of the acetyl group is conveniently carried out using a base such as potassium carbonate in a suitable solvent such as methanol. The reaction is carried out at ambient temperature and the product of Formula XXII can be isolated using conventional methods.

Several compounds of Formula XXII, wherein m and n are both 0, are known and have been prepared by other related routes; see for example, U.S. Pat. No. 4,689,338 (Gerster), U.S. Pat. No. 6,194,425 (Gerster et al.), U.S. Pat. No. 5,605,899 (Gerster et al.), and U.S. Pat. No. 5,175,296 (Gerster).

In step (8) of Reaction Scheme I, a hydroxy-substituted compound of Formula XXII is treated with N-hydroxyphthalimide under Mitsunobu reaction conditions to provide an N-phthalimide-protected hydroxylamine of Formula XXIII. The reaction is conveniently carried out by adding triphenylphosphine and N-hydroxyphthalimide to a solution of the alcohol of Formula XXII in a suitable solvent such as tetrahydrofuran or DMF and then slowly adding diisopropyl azodicarboxylate. The reaction can be carried out at ambient temperature or at an elevated temperature, such as 60° C. The product can be isolated using conventional methods.

In step (9) of Reaction Scheme I, an N-phthalimide-protected hydroxylamine of Formula XXIII is oxidized to provide a 1H-imidazo[4,5-c][1,5]naphthyridine-5N-oxide or 1H-imidazo[4,5-c]quinoline-5N-oxide of Formula XXIV using a conventional oxidizing agent capable of forming N-oxides. The reaction is conveniently carried out by adding 3-chloroperoxybenzoic acid to a solution of a compound of Formula XXIII in a solvent such as chloroform or dichloromethane. The reaction can be carried out at ambient temperature. The product can be isolated using conventional methods.

In step (10) of Reaction Scheme I, a 1H-imidazo[4,5-c][1,5]naphthyridine-5N-oxide or 1H-imidazo[4,5-c]quinoline-5N-oxide of Formula XXIV is aminated to provide a 1H-imidazo[4,5-c][1,5]naphthyridin-4-amine or 1H-imidazo[4,5-c]quinolin-4-amine of Formula XXV. Step (10) involves the activation of an N-oxide of Formula XXIV by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XXIV in a suitable solvent such as dichloromethane or chloroform and then adding p-toluenesulfonyl chloride. The reaction can be carried out at ambient temperature. Under these reaction conditions, the N-phthalimide protecting group is removed to provide the 1H-imidazo[4,5-c][1,5]naphthyridin-4-amine or 1H-imidazo[4,5-c]quinolin-4-amine of Formula XXV or a pharmaceutically acceptable salt thereof, which can be isolated from the reaction mixture using conventional methods.

Steps (9) and (10) can alternatively be combined and carried out as a one-pot procedure by adding 3-chloroperoxybenzoic acid to a solution of a compound of Formula XXIII in a solvent such as dichloromethane or chloroform and then adding ammonium hydroxide and p-toluenesulfonyl chloride without isolating the N-oxide of Formula XXIV. The product of Formula XXV or pharmaceutically acceptable salt thereof can be isolated using conventional methods.

In step (11) of Reaction Scheme I, an hydroxylamine-substituted 1H-imiazo[4,5-c][1,5]naphthyridin-4-amine or 1H-imidazo[4,5-c]quinolin-4-amine of Formula XXV is converted to a compound of Formula XXVI, a subgenus of Formulas I and II, using conventional methods. For example, a compound of Formula XXV can react with an acid chloride of Formula $R_1C(O)Cl$ to provide a compound of Formula XXVI in which Y' is —C(O)— and $R_1$ is as defined above. In addition, a compound of Formula XXV can react with a sulfonyl chloride of Formula $R_1S(O)_2Cl$ or a sulfonic anhydride of Formula $(R_1S(O)_2)_2O$ to provide a compound of Formula XXVI in which Y' is —S(O)$_2$— and $R_1$ is as defined above. Numerous acid chlorides of Formula $R_1C(O)Cl$, sulfonyl chlorides of Formula $R_1S(O)_2Cl$, and sulfonic anhydrides of Formula $(R_1S(O)_2)_2O$ are commercially available; others can be readily prepared using known synthetic methods. The reaction is conveniently carried out by adding the acid chloride of Formula $R_1C(O)Cl$, sulfonyl chloride of Formula $R_1S(O)_2Cl$, or sulfonic anhydride of Formula $(R_1S(O)_2)_2O$ to a solution of compound of Formula XXV in a suitable solvent such as chloroform, dichloromethane, or DMF. Optionally a base such as triethylamine or N,N-diisopropylethylamine can be added. The reaction can be carried out at ambient temperature or at an elevated temperature such as 50° C. The product or pharmaceutically acceptable salt thereof can be isolated using conventional methods.

Ureas of Formula XXVI, where Y' is —C(O)—N($R_8$)—, —C(S)—N($R_8$)—, —C(O)—N($R_8$)—S(O)$_2$—, —C(O)—N($R_8$)—C(O)—, or

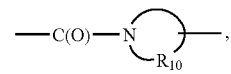

and $R_1$, $R_8$, and $R_{10}$ are defined as above, or Y' is —C(O)— and $R_1$ is heterocyclyl, wherein the heterocyclyl group is attached at a nitrogen atom, can be prepared by reacting an hydroxylamine-substituted compound of Formula XXV with isocyanates of Formula $R_1N=C=O$ or Formula $R_1(CO)N=C=O$, isothiocyanates of Formula $R_1N=C=S$, sulfonyl isocyanates of Formula $R_1S(O)_2N=C=O$, or carbamoyl chlorides of Formula Cl—C(O)—N—($R_8$)—$R_1$, Formula Cl—C(O)-heterocyclyl, or Formula

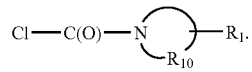

Numerous compounds of these types are commercially available; others can be readily prepared using known synthetic methods. The reaction can be carried out as described above for the reaction of a compound of Formula XXV with acid chlorides or sulfonyl chlorides.

Sulfamides of Formula XXVI, where Y' is —S(O)$_2$—N(R$_8$)— or

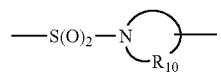

and R$_1$, R$_8$, and R$_{10}$ are as defined above, can be prepared by reacting a compound or salt of Formula XXV with sulfuryl chloride to generate a sulfamoyl chloride in situ, and then reacting the sulfamoyl chloride with an amine of Formula HN(R$_8$)R$_1$ or Formula

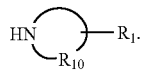

Alternatively, sulfamides of XXVI can be prepared by reacting a compound of Formula XXV with a sulfamoyl chloride of Formula R$_1$(R$_8$)N—S(O)$_2$Cl or

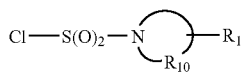

under the reaction conditions described above for reaction of compounds of Formula XXV with sulfonyl chlorides. The product or a pharmaceutically acceptable salt thereof can be isolated using conventional methods. Many amines of Formula HN(R$_8$)R$_1$ and Formula

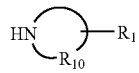

and some sulfamoyl chlorides of Formula R$_1$(R$_8$)N—S(O)$_2$Cl are commercially available; others can be prepared using known synthetic methods.

In step (12) of Reaction Scheme I, a compound of Formula XXVII, a subgenus of Formulas I and II wherein Y' is a bond —C(O)—, —C(S)—, —S(O)$_2$—, or —C(O)—C(O)—, and R'$_a$ and R$_1$ are as defined above, is prepared from a compound of Formula XXVI. Treatment of a compound of Formula XXVI with an alcohol of Formula R'$_a$—OH under Mitsunobu reaction conditions produces a compound of Formula XXVII. The reaction is carried out using the method described in step (8) of Reaction Scheme I. The product or pharmaceutically acceptable salt thereof can be isolated using conventional methods.

Alternatively, step (12) can be carried out by treating a compound of Formula XXVI, wherein Y' is a bond, —C(O)—, —C(S)—, —S(O)$_2$—, or —C(O)—C(O)—, with an alkylating agent of Formula R'$_a$—Br or R'$_a$—I in the presence of a base such as cesium carbonate in a suitable solvent such as DMF. The reaction may be carried out at ambient temperature for reactive alkylating agents such as, for example, methyl iodide, benzyl bromide, and substituted benzyl bromides, or at an elevated temperature. Optionally, catalytic tetrabutylammonium hydrogensulfate can be added. The product or pharmaceutically acceptable salt thereof can be isolated by conventional methods.

One skilled in the art would recognize that the reactions described for step (12) would probably not be successful for R'$_a$ groups that are difficult to introduce via bimolecular nucleophilic substitution reactions. These groups include, for example, sterically hindered alkyl groups.

Compounds of Formula XXVII, where R$_1$ and R' together with the nitrogen atom and Y' group to which they are bonded join together to form a ring of Formula

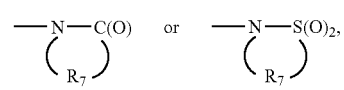

can be prepared in a two-step procedure, described by steps (11) and (12) of Reaction Scheme I. In step (11) of Reaction Scheme I, a hydroxylamine-substituted compound of Formula XXV reacts with a chloroalkanesulfonyl chloride of Formula Cl—R$_7$S(O)$_2$Cl or a chloroalkanoyl chloride of Formula Cl—R$_7$C(O)Cl, where R$_7$ is as defined above. The reaction is conveniently carried out by adding the chloroalkanesulfonyl chloride or chloroalkanoyl chloride to a solution of the compound of Formula XXV in a suitable solvent such as chloroform at ambient temperature, optionally in the presence of a base such as triethylamine. The isolable intermediate chloroalkanesulfonamide or chloroalkanamide can then be treated with a base such as 1,8-diazabicyclo[5.4.0]undec-7-ene at ambient temperature in a suitable solvent such as DMF to effect the cyclization in step (12) of Reaction Scheme I.

Alternatively, a compound of Formula XXVII, where R$_1$ and R' together with the nitrogen atom and Y' group to which they are bonded join together to form a ring, can be prepared in three steps using an appropriately protected hydroxyalkanoyl chloride of Formula P—O—R$_7$C(O)Cl, wherein P is a protecting group. A compound of Formula P—O—R$_7$C(O)Cl reacts with a compound of Formula XXV to generate an isolable intermediate that can then be deprotected to yield a hydroxyalkanamide. The isolable hydroxyalkanamide is cyclized to a compound of Formula XXVII under Mitsunobu conditions with diethyl azodicarboxylate and triphenylphosphine in a suitable solvent such as tetahydrofuran at ambient temperature. The product of Formula XXVII or pharmaceutically acceptable salt thereof can be isolated using conventional methods.

For some embodiments, compounds in Reaction Scheme I can be further elaborated using known synthetic methods. For example, the acid chloride used in step (7) of Reaction Scheme I may contain a protected hydroxy or amino group. Some acid chlorides of this type, for example acetoxyacetyl chloride, are commercially available. Others can be prepared by known synthetic methods. The protected hydroxy or amino group may be deprotected and further functionalized before step (9) of Reaction Scheme I. For examples of this type of functionalization of an R$_2$ group, see U.S. Pat. No. 5,389,640 (Gerster et al.).

Reaction Scheme I

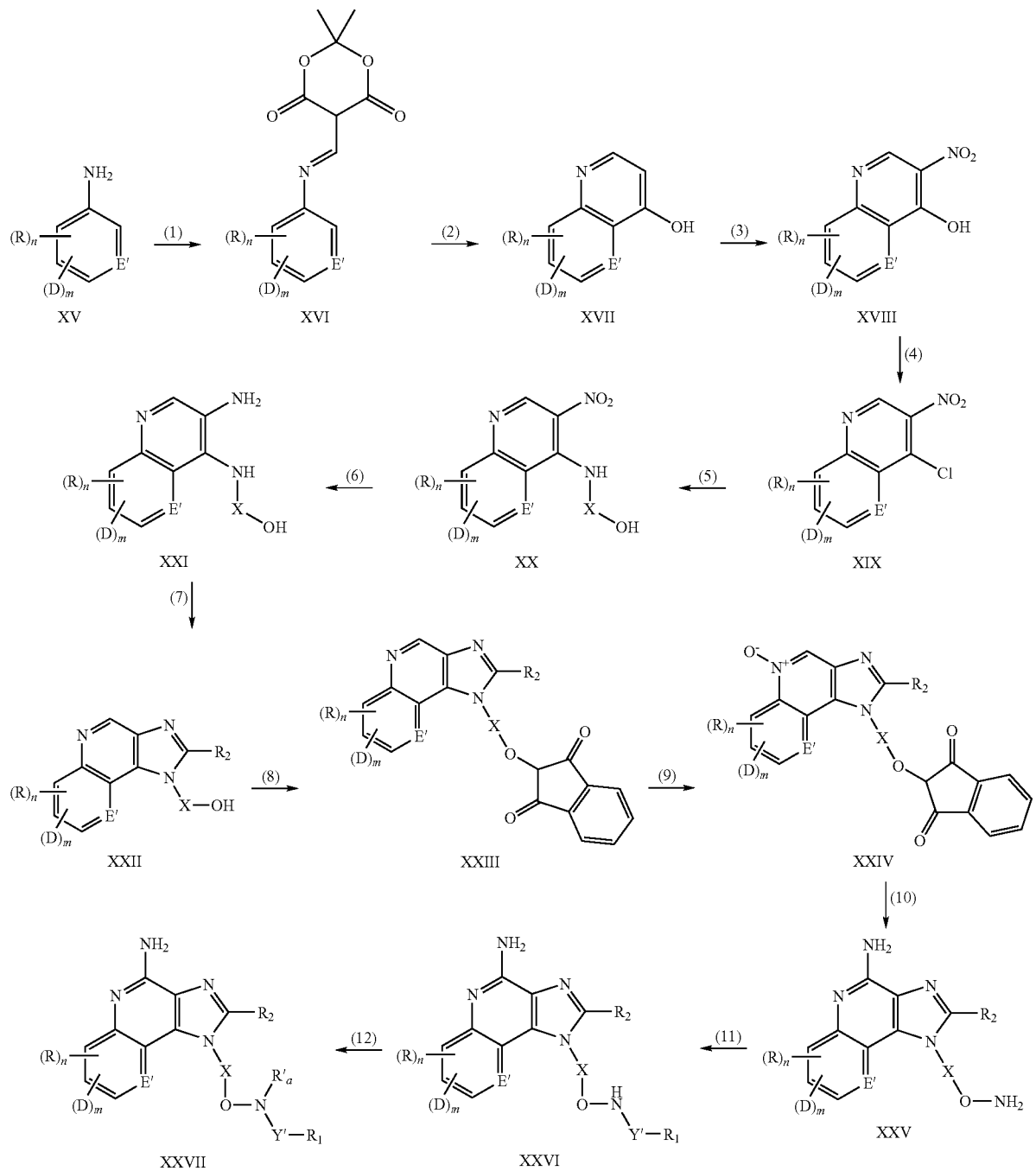

Compounds of the invention can be prepared according to Reaction Scheme II where R, $R_1$, $R_2$, X, D, E', m, n, and Y' are as defined above; $R'_b$ and $R'_c$ are independently selected from the group consisting of hydrogen, alkyl, alkenyl, aryl, arylalkylenyl, heteroaryl, heteroarylalkylenyl, heterocyclyl, heterocyclylalkylenyl, and alkyl, alkenyl, aryl, arylalkylenyl, heteroaryl, heteroarylalkylenyl, heterocyclyl, and heterocyclylalkylenyl substituted by one or more substituents selected from the group given above in the definition of R'; or $R'_b$ and $R'_c$ can join together to form a ring system containing one or two saturated or unsaturated rings optionally including one or more heteroatoms. In step (1) of Reaction Scheme II, a hydroxylamine-substituted 1H-imidazo[4,5-c][1,5]naphmyridin-4-amine or 1H-imidazo[4,5-c]quinolin-4-amine of Formula XXV reacts with an aldehyde or ketone of Formula $R'_bC(O)R'_c$ to provide an oxime of Formula XXVIII. Numerous aldehydes and ketones of Formula $R'_bC(O)R'_c$ are commercially available; others can be readily prepared using known synthetic methods. The reaction can be conveniently carried out by adding the aldehyde or ketone of Formula R'$_b$C(O)R'$_c$ to a solution of a compound of Formula XXV in a suitable solvent such as methanol. The reaction can be carried out at ambient temperature, or at elevated temperature. Optionally, an acid such as pyridine hydrochloride can be added. The product or pharmaceutically acceptable salt thereof can be isolated using conventional methods.

In step (2) of Reaction Scheme II, an oxime of Formula XXVIII is reduced to provide a hydroxylamine of Formula XXIX. The reduction is conveniently carried out by treating the oxime of Formula XXVIII with excess sodium cyanoborohydride in a suitable solvent or solvent mixture such as methanol/acetic acid. Optionally, hydrochloric acid may be added. The reaction can be carried out at ambient temperature or at elevated temperature. The product or pharmaceutically acceptable salt thereof can be isolated using conventional methods.

In step (3) of Reaction Scheme II, a compound of Formula XXIX converted into a compound of Formula XXVIIa using the reagents and methods described in step (11) or step (12) of Reaction Scheme I. The product or pharmaceutically acceptable salt thereof can be isolated by conventional methods.

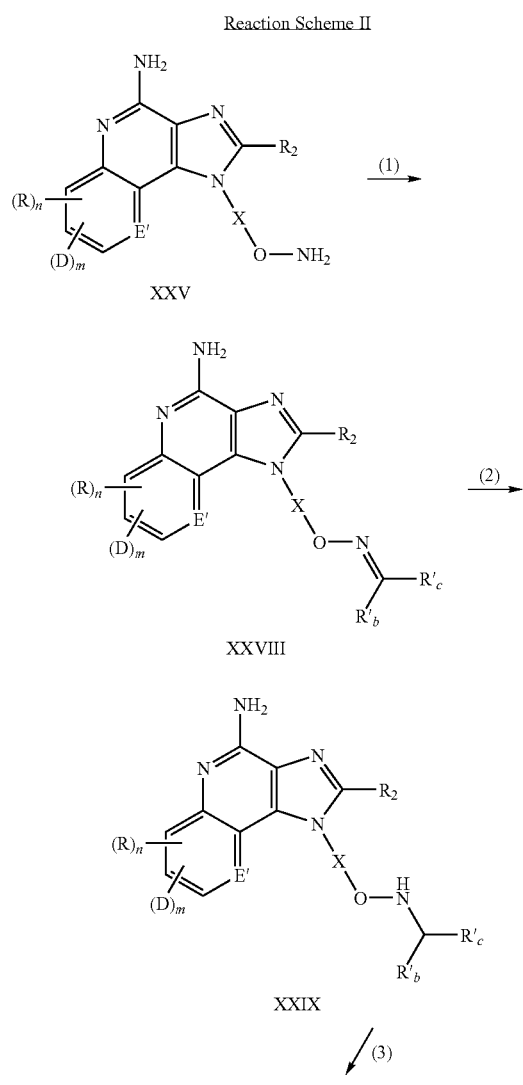

Reaction Scheme II

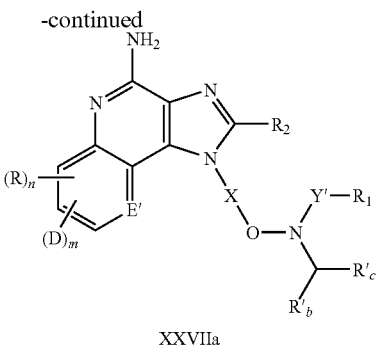

XXVIIa

Compounds of the invention can also be prepared according to Reaction Scheme III, wherein R, R', R$_1$, R$_2$, E', Y', and X are as defined above; n is 0 or 1; and R$_{3a}$ is —O—R$_{4a}$, —O—X'—R$_4$, —O—X'—Y—R$_4$, or —O—X'—R$_5$; where R$_4$, R$_5$, X' and Y are as defined above, and R$_{4a}$ is aryl or heteroaryl where the aryl or heteroaryl groups can be unsubstituted or substituted as defined in R$_4$ above. Formula XXVIIb is a subset of Formula XXVII, defined in Reaction Scheme I, wherein D is —OCH$_2$Ph; compounds of Formula XXVIIb can be prepared according to the methods described in Reaction Schemes I and II. In step (1) of Reaction Scheme III, the benzyl group in a benzyloxy-substituted 1H-imidazo [4,5-c][1,5]naphthyridin-4-amine or 1H-imidazo[4,5-c] quinolin-4-amine of Formula XXVIIb is cleaved to provide a compound of Formula XXVIIc. The cleavage is conveniently carried out on a Parr apparatus under hydrogenolysis conditions using a suitable heterogeneous catalyst such as palladium or platinum on carbon in a solvent such as ethanol. Alternatively, the reaction can be carried out by transfer hydrogenation in the presence of a suitable hydrogenation catalyst. The transfer hydrogenation is conveniently carried out by adding ammonium formate to a solution of a compound of Formula XXVIIb in a suitable solvent such as ethanol in the presence of a catalyst such as palladium on carbon. The reaction is carried out at an elevated temperature, for example, the refluxing temperature of the solvent. The product or pharmaceutically acceptable salt thereof can be isolated using conventional methods.

In step (2) of Reaction Scheme III, a hydroxy-substituted compound of Formula XXVIIc is converted to an ether-substituted compound of Formula XXVIId using a Williamson-type ether synthesis. The reaction is effected by treating a compound of Formula XXVIIc with an aryl or alkyl halide of Formula Halide-R$_{4a}$, Halide-alkylene-R$_4$, Halide-alkylene-Y—R$_4$ or Halide-alkylene-R$_5$ in the presence of a base. Numerous reagents of Formulas Halide-R$_{4a}$, Halide-alkylene-R$_4$, Halide-alkylene-Y—R$_4$ or Halide-alkylene-R$_5$ are commercially available, including substituted benzyl bromides and chlorides, substituted or unsubstituted alkyl or arylalkylenyl bromides and chlorides, and substituted fluorobenzenes. Other reagents of these Formulas can be prepared using conventional synthetic methods. The reaction is conveniently carried out by combining a reagent of Formula Halide-R$_{4a}$, Halide-alkylene-R$_4$, Halide-alkylene-Y—R$_4$ or Halide-alkylene-R$_5$ with a hydroxy-substituted compound of Formula XXVIIc in a solvent such as DMF in the presence of a suitable base such as cesium carbonate. Optionally, catalytic tetrabutylammonium bromide can be added. The reaction can be carried out at ambient temperature or at an elevated temperature, for example 65° C. or 85° C., depending on the reactivity of the aryl or alkyl halide. The product or pharmaceutically acceptable salt thereof can be isolated using conventional methods.

Alternatively, step (2) may be carried out using the Ullmann ether synthesis, in which an alkali metal aryloxide of a compound of Formula XXVIIc reacts with an aryl halide in the presence of copper salts, to provide a compound of Formula XXVIId, where $R_{3a}$ is —O—$R_{4a}$, —O—X'—$R_4$, or —O—X'—Y—$R_4$, wherein X' is an arylene or heteroarylene. Numerous substituted and unsubstituted aryl halides are commercially available; others can be prepared using conventional methods.

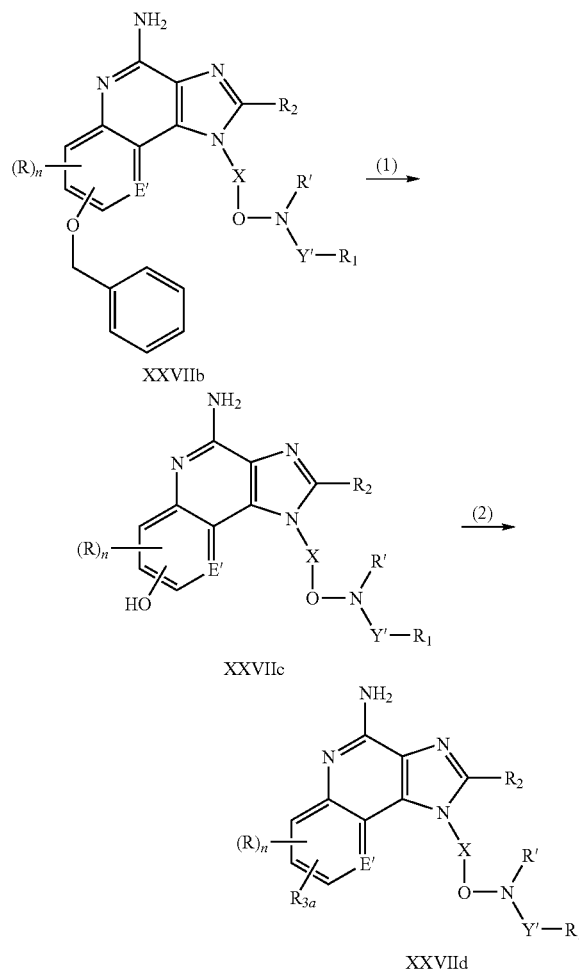

Reaction Scheme III

Compounds of the invention can also be prepared according to Reaction Scheme IV, wherein R, R', $R_1$, $R_2$, E', X, Y', and n are as defined in Reaction Scheme III; Hal is —Br or —I; and $R_{3b}$ and $R_{3c}$ are as defined below. Formula XXVIIe is a subset of Formula XXVII, defined in Reaction Scheme I, wherein D is —Br or —I; compounds of Formula XXVIIe can be made according to the methods described in Reaction Schemes I and II. Step (1) of Reaction Scheme IV can be carried out using known palladium-catalyzed coupling reactions such as the Suzuki coupling and the Heck reaction. For example, a halogen substituted 1H-imidazo[4,5-c][1,5]naphthyridin-4-amine or 1H-imidazo[4,5-c]quinolin-4-amine of Formula XXVIIe undergoes Suzuki coupling with a boronic acid of Formula $R_{3b}$—B(OH)$_2$, an anhydride thereof, or a boronic acid ester of Formula $R_{3b}$—B(O-alkyl)$_2$ to provide a compound of Formula XXVIIf, wherein $R_{3b}$ is —$R_{4a}$, —X'$_a$—$R_4$, —X'$_b$—Y—$R_4$, or —X'$_b$—$R_5$, where $R_{4a}$ is as defined above; X'$_a$ is alkenylene; X'$_b$ is arylene, heteroarylene, or alkenylene interrupted or terminated by arylene or heteroarylene; and $R_4$, $R_5$, and Y are as defined above. The coupling is carried out by combining a compound of Formula XXVIIe with a boronic acid or an ester or anhydride thereof in the presence of palladium (II) acetate, triphenylphosphine, and a base such as sodium carbonate in a suitable solvent such as n-propanol. The reaction can be carried out at an elevated temperature, for example, at the reflux temperature. Numerous boronic acids of Formula $R_{3b}$—B(OH)$_2$, anhydrides thereof, and boronic acid esters of Formula $R_{3b}$—B(O-alkyl)$_2$ are commercially available; others can be readily prepared using known synthetic methods. See, for example, Li, W. et al, *J. Org. Chem.*, 67, 5394-5397 (2002). The product of Formula XXVIIf or a pharmaceutically acceptable salt thereof can be isolated by conventional methods.

The Heck reaction can also be used in step (1) of Reaction Scheme IV to provide compounds of Formula XXVIIf, wherein $R_{3b}$ is —X'$_a$—$R_{4a}$ and X'$_a$—Y—$R_4$. The Heck reaction is carried out by coupling a compound of Formula XXVIIe with a compound of the Formula H$_2$C=C(H)—$R_{4a}$ or H$_2$C=C(H)—Y—$R_4$. Several of these vinyl-substituted compounds are commercially available; others can be prepared by known methods. The reaction is conveniently carried out by combining the compound of Formula XXVIIe and the vinyl-substituted compound in the presence of palladium (II) acetate, triphenylphosphine or tri-ortho-tolylphosphine, and a base such as triethylamine in a suitable solvent such as acetonitrile or toluene. The reaction can be carried out at an elevated temperature such as 100-120° C. under an inert atmosphere. The product of Formula XXVIIf or pharmaceutically acceptable salt thereof can be isolated using conventional methods.

Compounds of Formula XXVIIf, wherein $R_{3b}$ is —X'$_c$—$R_4$, X'$_c$ is alkynylene, and $R_4$ is as defined above, can also be prepared by palladium catalyzed coupling reactions such as the Stille coupling or Sonogashira coupling. These reactions are carried out by coupling a compound of Formula XXVIIe with a compound of the Formula (alkyl)$_3$Sn—C≡C—$R_4$, (alkyl)$_3$Si—C≡C—$R_4$, or H—C≡C—$R_4$.

Compounds of the invention, wherein $R_{3c}$ is —X'$_d$—$R_4$, —X'$_d$—Y—$R_4$, —X'$_e$—Y—$R_4$, or —X'$_e$—$R_5$, where X'$_d$ is alkylene; X'$_e$ is alkylene interrupted or terminated by arylene or heteroarylene; and $R_4$, $R_5$, and Y are as defined above, can be prepared as shown in step (2) of Reaction Scheme IV. In step (2) of Reaction Scheme IV, a compound of Formula XXVIIf, wherein $R_{3b}$ is —X'$_a$—$R_4$, —X'$_a$—Y—$R_4$, —X'$_b$—Y—$R_4$, —X'$_b$—$R_5$, or —X'$_c$—$R_4$, where X'$_b$ is alkenylene interrupted or terminated by arylene or heteroarylene, and X'$_a$, X'$_c$, Y, $R_4$, and $R_5$ are as defined above, is reduced to provide a compound of Formula XXVIIg. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof. The product or pharmaceutically acceptable salt thereof can be isolated using conventional methods.

Reaction Scheme IV

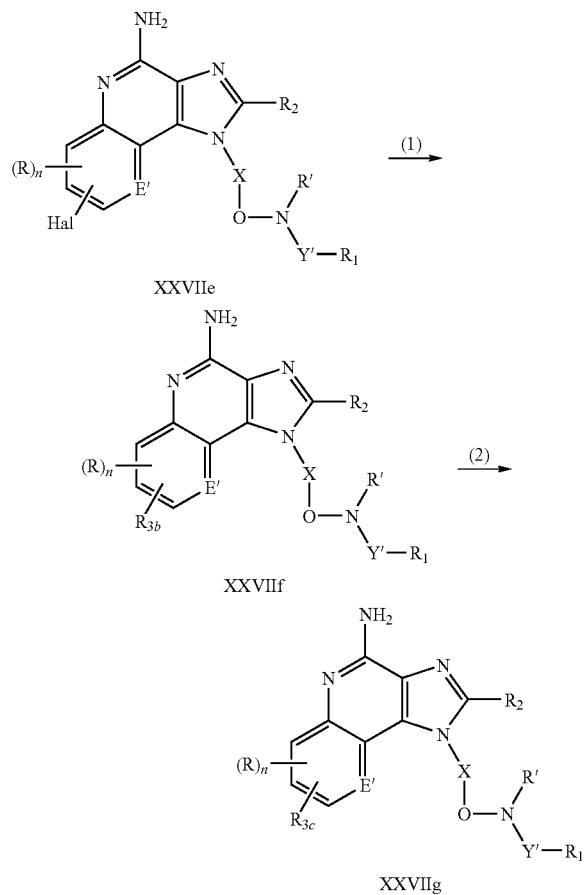

Tetrahydroquinolines and tetrahydronaphthyridines of the invention can be prepared according to Reaction Scheme V, wherein E', X, Y', $R'_a$, $R'_b$, $R_c$, and $R_1$ are as defined above; n is an integer from 0 to 4 (imidazoquinoline ring system) or 0 to 3 (imidazonaphthyridine ring system); $R_b$ is alkyl, alkoxy, or $-N(R_9)_2$; and $R_{2b}$ is a subset of $R_2$ as defined above that does not include those substituents that one skilled in the art would recognize as being susceptible to reduction under the acidic hydrogenation conditions of step (2). These susceptible groups include, for example, alkenyl, alkynyl, and aryl groups and groups bearing nitro substituents. Compounds of Formula XXIIa can be prepared as shown in Reaction Scheme I.

In step (1) of Reaction Scheme V, a hydroxy-substituted compound of Formula XXIIa is oxidized and aminated to provide a 1H-imidazo[4,5-c][1,5]naphthyridin-4-amine or 1H-imidazo[4,5-c]quinolin-4-amine of Formula XXX. The oxidation and amination can be carried out as described in steps (9) and (10) of Reaction Scheme I.

In step (2) of Reaction Scheme V, a compound of Formula XXX is reduced to a 6,7,8,9-tetrahydro compound of Formula XXXI. The reaction is conveniently carried out under hetereogeneous hydrogenation conditions by adding platinum (IV) oxide to a solution of the compound of Formula XXX in trifluoroacetic acid and placing the reaction under hydrogen pressure. The reaction can be carried out on a Parr apparatus at ambient temperature. The product or pharmaceutically acceptable salt thereof can be isolated by conventional methods.

In step (3) of Reaction Scheme V, a hydroxy-substituted compound of Formula XXXI is converted to a hydroxylamine of Formula XXXII. The reaction is carried out under the Mitsunobu reaction conditions as described for step (8) of Reaction Scheme I, and during the isolation of the reaction product, the N-phthalimide protecting group is removed by treatment with a strong base. Conveniently, an acidic aqueous solution of a N-phthalimide-protected hydroxylamine prepared from a compound of Formula XXXI is treated with sodium hydroxide until the pH of the solution is basic. The hydroxylamine of Formula XXXII can then be isolated using conventional methods. Alternatively, the Mitsunobu reaction can be carried out as described in step (8) of Reaction Scheme I to provide a N-phthalimide-protected hydroxylamine, which can be treated with hydrazine in a suitable solvent such as ethanol at ambient temperature to provide a hydroxylamine of Formula XXXII. The product can be isolated by conventional methods.

In step (4) of Reaction Scheme V, the hydroxylamine group in a compound of Formula XXXII reacts with an aldehyde or ketone of Formula $R'_bC(O)R'_c$ to provide an oxime of Formula XXXIII. The reaction can be carried out as described above in step (1) of Reaction Scheme II. The product or pharmaceutically acceptable salt thereof can be isolated by conventional methods.

In step (5) of Reaction Scheme V, the oxime of Formula XXXIII is reduced using the conditions described in step (2) of Reaction Scheme II to afford a compound of Formula XXXIV, a subgenus of Formulas I and II. The product or pharmaceutically acceptable salt thereof can be isolated by conventional methods.

In step (6) of Reaction Scheme V, a hydroxylamine of Formula XXXIV is converted into a compound of Formula XXXV, a subgenus of Formulas I and II, using the reagents and conditions described in step (11) or step (12) of Reaction Scheme I. The product or pharmaceutically acceptable salt thereof can be isolated by conventional methods.

Reaction Scheme V

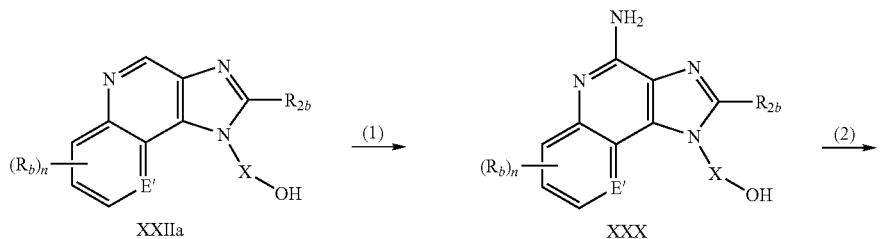

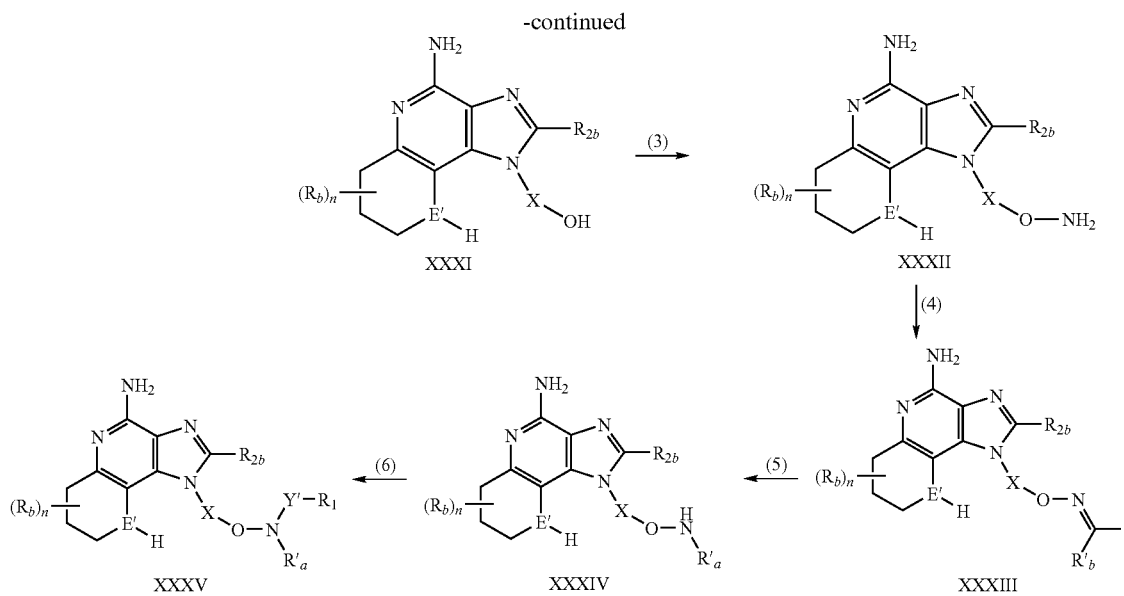

For some embodiments, compounds of the invention are prepared according to Reaction Scheme VI, where $R'_a$, $R'_b$, $R'_c$, $R_1$, $R_2$, $R_{A1}$, $R_{B1}$, $Y'$, $X$, and $Ph$ are as defined above. In step (1) of Reaction Scheme VI, a 2,4-dichloro-3-nitropyridine of Formula XXXVI is reacted with an amino alcohol of the Formula H$_2$N—X—OH to form a 2-chloro-3-nitropyridine of Formula XXXVII. The reaction is conveniently carried out by combining an amino alcohol of Formula H$_2$N—X—OH and a 2,4-dichloro-3-nitropyridine of Formula XXXVI in the presence of a base such as triethylamine in an inert solvent such as DMF. The reaction can be carried out at ambient temperature, and the product can be isolated from the reaction mixture using conventional methods. Several amines of Formula HO—X—NH$_2$ are commercially available; others can be prepared by known synthetic methods. Many 2,4-dichloro-3-nitropyridines of the Formula XXXVI are known and can be readily prepared using known synthetic methods. (See, for example, Dellaria et al, U.S. Pat. No. 6,525,064 and the references cited therein.)

In step (2) of Reaction Scheme VI, a 2-chloro-3-nitropyridine of Formula XXXVII is reacted with an alkali metal azide to provide an 8-nitrotetrazolo[1,5-α]pyridin-7-amine of Formula XXXVIII. The reaction can be carried out by combining the compound of Formula XXXVII with an alkali metal azide, for example, sodium azide, in a suitable solvent such as acetonitrile/water, preferably 90/10 acetonitrile/water, in the presence of cerium(III) chloride, preferably cerium(III) chloride heptahydrate. Optionally, the reaction can be carried out with heating, for example, at the reflux temperature. Alternatively, the reaction can be carried out by combining the compound of Formula XXXVII with an alkali metal azide, for example, sodium azide, in a suitable solvent such as DMF and heating, for example, to about 50-60° C., optionally in the presence of ammonium chloride. The product can be isolated from the reaction mixture using conventional methods.

In step (3) of Reaction Scheme VI, an 8-nitrotetrazolo[1,5-α]pyridin-7-amine of Formula XXXVIII is reduced to provide a compound of Formula XXXIX. The reduction can be carried out as described in step (6) of Reaction Scheme I.

In step (4) of Reaction Scheme VI, a tetrazolo[1,5-α]pyridine-7,8-diamine of Formula XXXIX is reacted with a carboxylic acid equivalent to provide a 7H-imidazo[4,5-c]tetrazolo[1,5-α]pyridine of Formula XL. The reaction can be carried out as described in step (7) of Reaction Scheme I.

A compound of Formula XL can also be prepared from a compound of Formula XXXVIII, wherein the alcohol group in a compound of Formula XXXVIII is first protected with an appropriate protecting group such as an acetyl group. The incorporation of the acetyl group, subsequent reduction and cyclization, and removal of the acetyl group is described in Reaction Scheme I.

In step (5) of Reaction Scheme VI, a hydroxy-substituted compound of Formula XL is treated with N-hydroxyphthalimide under Mitsunobu reaction conditions to provide an N-phthalimide-protected hydroxylamine of Formula XLI. The reaction is carried out under Mitsunobu reaction conditions as described for step (8) of Reaction Scheme I.

In step (6) of Reaction Scheme VI, the N-phthalimide-protected hydroxylamine of Formula XLI is treated with hydrazine in a suitable solvent such as ethanol to provide a hydroxylamine of Formula XLII. The reaction can be carried out at ambient temperature and the product can be isolated from the reaction mixture using conventional methods.

In step (7) Reaction Scheme VI, the hydroxylamine group in a 7H-imidazo[4,5-c]tetrazolo[1,5-α]pyridine of Formula XLII reacts with an aldehyde or ketone of Formula $R'_bC(O)R'_c$ to provide an oxime of Formula XLIII. The reaction can be carried out using the conditions described above in step (1) of Reaction Scheme II.

In step (8) of Reaction Scheme VI, the tetrazolo ring can be removed from a 7H-imidazo[4,5-c]tetrazolo[1,5-α]pyridine of Formula XLIII by reaction with triphenylphosphine to form an N-triphenylphosphinyl intermediate of Formula XLIV. The reaction with triphenylphosphine can be run in a suitable solvent such as toluene or 1,2-dichlorobenzene under an atmosphere of nitrogen with heating, for example at the reflux temperature.

In step (9) of Reaction Scheme VI, an N-triphenylphosphinyl intermediate of Formula XLIV is hydrolyzed to provide an oxime-substituted 1H-imidazo[4,5-c]pyridin-4-amine of Formula XLV. The hydrolysis can be carried out by general methods well known to those skilled in the art, for example, by heating in a lower alkanol in the presence of an acid such as trifluoroacetic acid or hydrochloric acid. The product can be isolated from the reaction mixture using conventional methods as the compound of Formula XLV or as a pharmaceutically acceptable salt thereof.

A compound of the Formula XLV may also be obtained through an alternative route from a compound of Formula XLI. In step (6a) of Reaction Scheme VI, a compound of Formula XLI is treated sequentially according to the reaction conditions described in steps (8) and (9) of Reaction Scheme VI using hydrochloric acid as the acid in step (9). Under these reaction conditions, the N-phthalimide is removed to provide the hydroxylamine-substituted 1H-imidazo[4,5-c]pyridin-4-amine of Formula XLVII. The product can be isolated and purified using conventional methods.

In step (7a) of Reaction Scheme VI, a hydroxylamine-substituted 1H-imidazo[4,5-c]pyridin-4-amine of Formula XLVII reacts with an aldehyde or ketone of Formula R'$_b$C(O)R'$_c$ to provide an oxime of Formula XLV. The reaction can be carried out as described above in step (1) of Reaction Scheme II. The product can be isolated from the reaction mixture using conventional methods as the compound of Formula XLV or as a pharmaceutically acceptable salt thereof.

In step (10) of Reaction Scheme VI, the oxime of Formula XLV is reduced using the conditions described in step (2) of Reaction Scheme II to afford a compound of Formula XLVI, a subgenus of Formulas I, II, and VI. The product or pharmaceutically acceptable salt thereof can be isolated by conventional methods.

In step (11) of Reaction Scheme VI, a hydroxylamine of Formula XLVI is converted into a compound of Formula VIa, a subgenus of Formulas I, II, and VI, using the reagents and conditions described in step (11) of Reaction Scheme I. The product or pharmaceutically acceptable salt thereof can be isolated by conventional methods.

Alternatively, in steps (10a) and (11a) of Reaction Scheme VI, a hydroxylamine of Formula XLVII is converted into a compound of Formula VIa using the reagents and methods described in steps (11) and (12), respectively, of Reaction Scheme I. The product or pharmaceutically acceptable salt thereof can be isolated by conventional methods.

Reaction Scheme VI

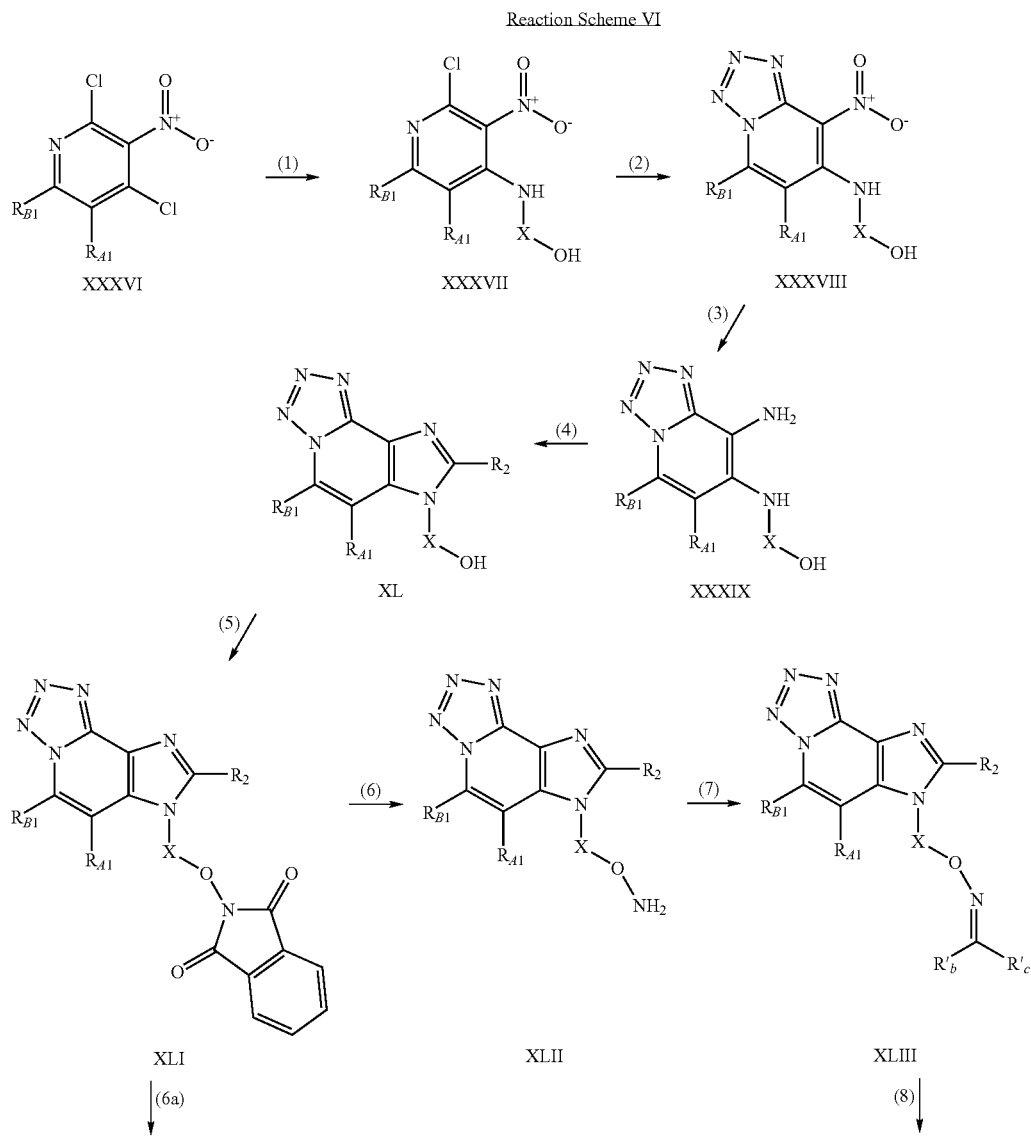

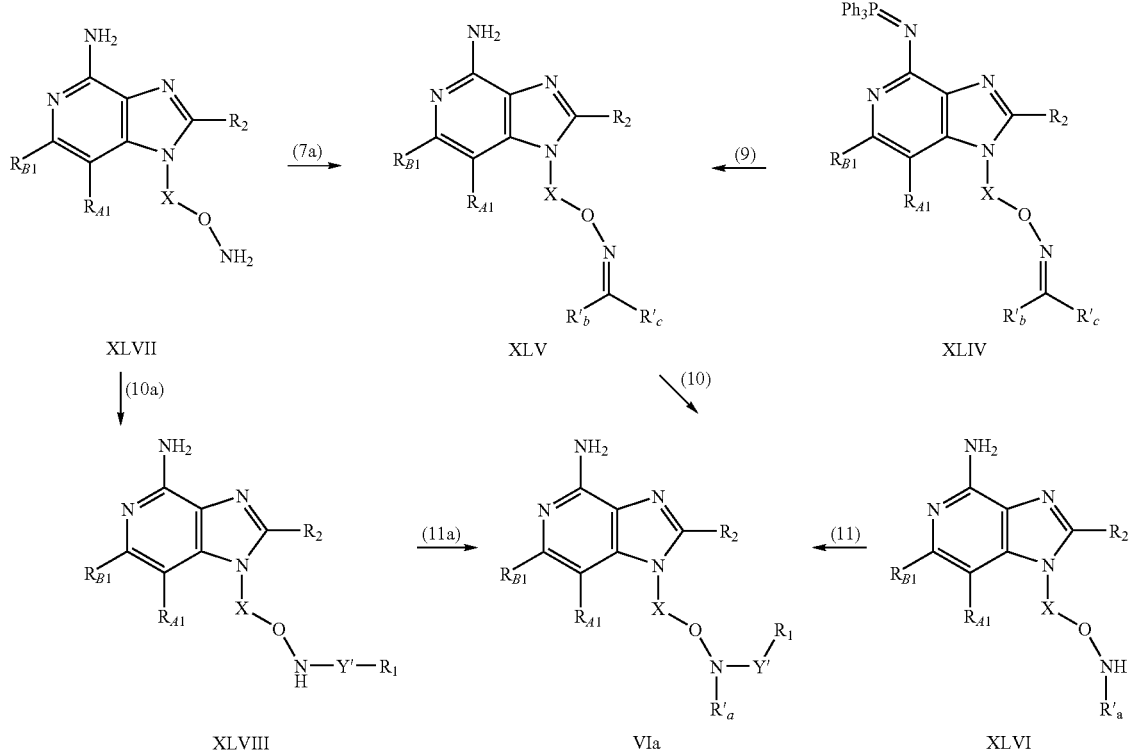

Pharmaceutical Compositions and Biological Activity

Pharmaceutical compositions of the invention contain a therapeutically effective amount of a compound of the invention as described above in combination with a pharmaceutically acceptable carrier.

The terms "a therapeutically effective amount" and "effective amount" mean an amount of the compound sufficient to induce a therapeutic or prophylactic effect, such as cytokine induction, immunomodulation, antitumor activity, and/or antiviral activity. Although the exact amount of active compound used in a pharmaceutical composition of the invention will vary according to factors known to those of skill in the art, such as the physical and chemical nature of the compound, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (μg/kg) to about 5 mg/kg, of the compound to the subject. A variety of dosage forms may be used, such as tablets, lozenges, capsules, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, antibodies, proteins, peptides, oligonucleotides, etc.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, IL-6, IL-10 and IL-12, and a variety of other cytokines. Among other effects, these and other cytokines can inhibit virus production and tumor cell growth, making the compounds useful in the treatment of viral diseases and neoplastic diseases. Accordingly, the invention provides a method of inducing cytokine biosynthesis in an animal comprising administering an effective amount of a compound or composition of the invention to the animal. The animal to which the compound or composition is administered for induction of cytokine biosynthesis may have a disease as described infra, for example a viral disease or a neoplastic disease, and administration of the compound may provide therapeutic treatment. Alternatively, the compound may be administered to the animal prior to the animal acquiring the disease so that administration of the compound may provide a prophylactic treatment.

In addition to the ability to induce the production of cytokines, compounds of the invention can affect other aspects of the innate immune response. For example, natural killer cell activity may be stimulated, an effect that may be due to cytokine induction. The compounds may also activate macrophages, which in turn stimulate secretion of nitric oxide and the production of additional cytokines. Further, the compounds may cause proliferation and differentiation of B-lymphocytes.

Compounds of the invention can also have an effect on the acquired immune response. For example, the production of the T helper type 1 ($T_H1$) cytokine IFN-γ can be induced indirectly and the production of the T helper type 2 ($T_H2$) cytokines IL-4, IL-5 and IL-13 can be inhibited upon administration of the compounds.

Whether for prophylaxis or therapeutic treatment of a disease, and whether for effecting innate or acquired immunity, the compound or composition may be administered alone or in combination with one or more active components as in, for example, a vaccine adjuvant. When administered with other components, the compound and other component or components may be administered separately; together but independently such as in a solution; or together and associated with one another such as (a) covalently linked or (b) non-covalently associated, e.g., in a colloidal suspension.

Conditions for which IRMs identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella;*

(c) other infectious diseases, such chlamydia, fungal diseases including but not limited to candidiasis, aspergillosis, histoplasmosis, cryptococcal meningitis, or parasitic diseases including but not limited to malaria, *Pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, renal cell carcinoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers; and (e) $T_H2$-mediated, atopic, and autoimmune diseases, such as atopic dermatitis or eczema, eosinophilia, asthma, allergy, allergic rhinitis, systemic lupus erythematosus, essential thrombocythaemia, multiple sclerosis, Ommen's syndrome, discoid lupus, alopecia areata, inhibition of keloid formation and other types of scarring, and enhancing would healing, including chronic wounds.

IRMs identified herein also may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; glycoproteins; peptides; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

IRMs may also be particularly helpful in individuals having compromised immune function. For example, IRM compounds may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased over the background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal and a method of treating a neoplastic disease in an animal comprising administering an effective amount of a compound or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

Objects and advantages of this invention are further illustrated by the following examples, but the particular materials and amounts thereof recited in these examples, as well as other conditions and details, should not be construed to unduly limit this invention.

EXAMPLES

Example 1

1-[3-(Aminooxy)propyl]-2-propyl-1H-imidazo[4,5-c]quinolin-4-amine

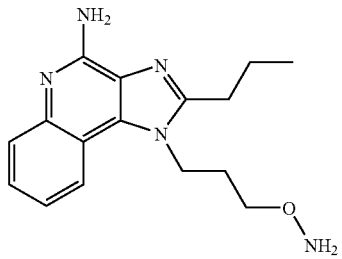

Part A

A solution of 3-(2-propyl-1H-imidazo[4,5-c]quinolin-1-yl)propan-1-ol (20.0 grams (g), 74.3 millimoles (mmol)) in tetrahydrofuran (300 milliliters (mL)) was cooled to approximately 0° C.; triphenylphosphine (23.4 g, 89.1 mmol) and N-hydroxyphthalimide (14.5 g, 89.1 mmol) were then added. After five minutes of stirring, diisopropyl azodicarboxylate (17.5 mL, 89.1 mmol) was added dropwise over a period of 15 minutes. The reaction was allowed to warm to room temperature and stirred overnight. The solvent was removed under reduced pressure, and the residue was dissolved in chloroform (300 mL). A solution of hydrochloric acid (150 mL of 6 molar (M)) was then added, and approximately 50 mL of the solvent was removed under reduced pressure to provide a white precipitate, which was stirred for ten minutes and isolated by filtration. Additional salt eventually precipitated from the filtrate and was isolated by filtration. Chloroform (300 mL) and water (300 mL) were added to the salt, and solid sodium bicarbonate was added to the mixture to adjust to pH 8. The organic solution was then dried over magnesium sulfate, filtered, and concentrated under reduced pressure to provide 28.4 g of 2-[3-(2-propyl-1H-imidazo[4,5-c]quinolin-1-yl)propoxy]-1H-isoindole-1,3(2H)-dione as a white solid.

$^1$H NMR (300 MHz, CDCl$_3$) δ 9.3 (s, 1H), 8.3 (m, 2H), 7.9 (m, 2H), 7.8 (m, 2H), 7.6 (m, 2H), 5.0 (t, J=7.3 Hz, 2H), 4.4 (t, 7=5.3 Hz, 2H), 3.1 (t, J=7.5 Hz, 2H), 2.4 (m, 2H), 2.1 (br s, m, 4H), 1.2 (t, J=7.3 Hz, 3H);

MS (APCI) m/z 415 (M+H)$^+$.

Part B

3-Chloroperoxybenzoic acid (14.9 g, 66.4 mmol) (mCPBA, available as an approximately 77% pure mixture) was added to a solution of 2-[3-(2-propyl-1H-imidazo[4,5-c]quinolin-1-yl)propoxy]-1H-isoindole-1,3(2H)-dione (25.0 g, 60.3 mmol) in chloroform (200 mL), and the reaction was stirred for seven hours at room temperature. An analysis by liquid chromatography/mass spectrometry (LC/MS) indicated that the reaction was incomplete, and additional mCPBA (4.96 g, 22.1 mmol) was added. The reaction was allowed to stir at room temperature overnight. The solution was then washed with brine (2×100 mL) and saturated aqueous sodium bicarbonate (2×100 mL), dried over magnesium sulfate, filtered, and concentrated under reduced pressure to provide a fluffy, light-brown solid. The solid was dried under high vacuum for one hour to provide 25.7 g of 2-[3-(5-oxido-2-propyl-1H-imidazo[4,5-c]quinolin-1-yl)propoxy]-1H-isoindole-1,3(2H)-dione as a white solid.

$^1$H NMR (300 MHz, CDCl$_3$) δ 9.1 (m, 2H), 8.3 (m, 1H), 7.9-7.7 (m, 6H), 5.0 (t, J=7.4 Hz, 2H), 4.4 (t, J=5.3 Hz, 2H), 3.1 (t, J=7.5 Hz, 2H), 2.4 (m, 2H), 2.1 (br s, m, 4H), 1.2 (t, J=7.3 Hz, 3H);

MS (APCI) m/z 431 (M+H)$^+$.

Part C

Ammonium hydroxide (75 mL) and p-toluenesulfonyl chloride (4.87 g, 25.6 mmol) were added to a solution of 2-[3-(5-oxido-2-propyl-1H-imidazo[4,5-c]quinolin-1-yl)propoxy]-1H-isoindole-1,3(2H)-dione (10.0 g, 23.2 mmol) in chloroform (100 mL), and the resulting mixture was stirred vigorously for one hour.) A white precipitate was removed by filtration, and the filtrate layers were separated. The organic solution was washed with brine (2×150 mL), dried over magnesium sulfate, filtered, and concentrated under reduced pressure to provide a yellow solid. The solid was purified by column chromatography on silica gel (eluting with dichloromethane:methanol:ammonium hydroxide ranging in ratios from 94:5:1 to 91:8:1) to provide 4.31 g of 1-[3-(aminooxy)propyl]-2-propyl-1H-imidazo[4,5-c]quinolin-4-amine as a beige powder, melting point (mp) 145-148° C.

$^1$H NMR (300 MHz, DMSO-d$_6$) δ 8.1 (d, J=7.5 Hz, 1H), 7.6 (d, J=8.3 Hz, 1H), 7.4 (t, J=8.1 Hz, 1H), 7.3 (t, J=8.1 Hz, 1H), 6.5 (br s, 2H), 6.1 (br s, 2H), 4.6 (t, J= 7.2 Hz, 2H), 3.6 (t, J=5.6 Hz, 2H), 2.9 (t, J=7.4 Hz, 2H), 2.1 (m, 2H), 1.9 (m, 2H), 1.1 (t, J=7.3 Hz, 3H); $^{13}$C NMR (75 MHz, DMSO-d$_6$) δ 153.4, 152.0, 145.0, 132.6, 126.8, 126.6, 121.5, 120.4, 115.1, 71.6, 42.5, 29.2, 28.5, 21.3, 14.2;

MS (APCI) m/z 300 (M+H)$^+$;

Anal, calcd for $C_{16}H_{21}N_5O$: C, 64.19; H, 7.07; N, 23.39. Found: C, 63.94; H, 7.20; N, 23.11.

Example 2

N-[3-(4-Amino-2-propyl-1H-imidazo[4,5-c]quinolin-1-yl)propoxy]cyclopropanecarboxamide

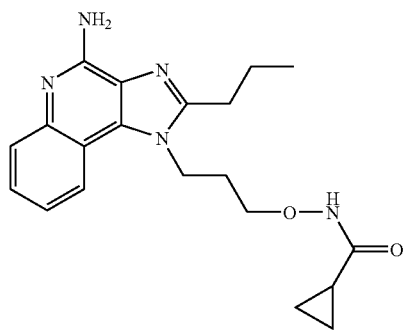

Triethylamine (1.86 mL, 13.4 mmol) was added to a mixture of 1-[3-(aminooxy)propyl]-2-propyl-1H-imidazo[4,5-c]quinolin-4-amine (2.00 g, 6.68 mmol), prepared as described in Example 1, and chloroform (20 mL). Cyclopropanecarbonyl chloride (673 microliters (μL), 7.35 mmol) was then added, and the resulting solution was stirred at room temperature overnight. The reaction was diluted with chloroform (50 mL), washed with brine (2×100 mL) and saturated aqueous sodium bicarbonate (2×100 mL), dried over magnesium sulfate, filtered, and concentrated under reduced pressure. The crude product was purified twice by column chromatography on silica gel (eluting sequentially with 97:2:1-dichloromethane:methanol:ammonium hydroxide and 96:3:1- dichloromethane:methanol:ammonium hydroxide) to provide 532 milligrams (mg) of N-[3-(4-amino-2-propyl-1H-imidazo[4,5-c]quinolin-1-yl)propoxy] cyclopropanecarboxamide as a white powder, mp 103-105° C.

$^1$H NMR (300 MHz, DMSO-d$_6$) δ 8.0 (d, J=7.9 Hz, 1H), 7.8 (d, J=7.8 Hz, 1H), 7.5 (t, J=7.4 Hz, 1H), 7.3 (t, J=8.0 Hz, 1H), 5.4 (br s, 2H), 4.7 (m, 2H), 4.0 (t, J=5.4 Hz, 2H), 2.9 (t, J=7.2 Hz, 2H), 2.2 (m, 2H), 1.9 (m, 2H), 1.3 (m, 1H), 1.1 (m, 5H), 0.9 (m, 2H);

MS (APCI) m/z 368 (M+H)$^+$;

HRMS (ESI) Theoretical mass: 368.2087, measured mass: 368.2073.

Anal, calcd for $C_{20}H_{25}$ $N_5O_2 \cdot 0.3CH_2Cl_2$: C, 62.05; H, 6.57; N, 17.82. Found: C, 61.85; H, 6.68; N, 17.79.

Examples 3-70

An acid chloride from the table below (0.83 equivalents, 0.057 mmol) was added to a test tube containing a solution of 1-[3-(aminooxy)propyl]-2-propyl-1H-imidazo[4,5-c]quinolin-4-amine (21 mg, 0.070 mmol) and N,N-diisopropylethylamine (24 μL), 0.14 mmol) in chloroform (2 mL). In Examples 17 and 69, dichloroethane was used as the solvent instead of chloroform. The test tube was capped and placed on a shaker at ambient temperature overnight (approximately 18 hours). For Example 70, an analysis by LC/MS indicated that the reaction was incomplete; therefore for Examples 69 and 70, the solutions additionally were heated at 50° C. for seven hours. The solvent was removed from the test tubes by vacuum centrifugation. The compounds were purified by preparative high performance liquid chromatography (prep HPLC) using a Waters Fraction Lynx automated purification system. The prep HPLC fractions were analyzed using a Micromass LC-TOFMS, and the appropriate fractions were centrifuge evaporated to provide the trifluoroacetate salt of the desired compound. Column: Phenomenex LUNA C18(2), 21.2×50 millimeters (mm), 10 micron particle size, 100 Angstroms (Å) pore; flow rate: 25 mL/min; non-linear gradient elution from 5-95% B in 9 minutes (min), then hold at 95% B for 2 min, where A is 0.05% trifluoroacetic acid/water and B is 0.05% trifluoroacetic acid/acetonitrile; fraction collection by mass-selective triggering. The table below shows the acid chloride used for each example, the structure of the resulting compound, and the observed accurate mass for the isolated trifluoroacetate salt.

Examples 3-70

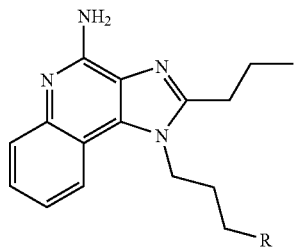

| Example | Acid Chloride | R | Measured Mass (M + H) |
|---|---|---|---|
| 3 | Isobutryl chloride | ![structure] | 370.2252 |
| 4 | Methoxyacetyl chloride | ![structure] | 372.2035 |
| 5 | 3,3-Dimethylacryloyl chloride | ![structure] | 382.2262 |

-continued
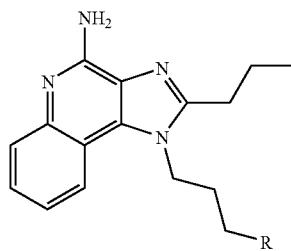
| Example | Acid Chloride | R | Measured Mass (M + H) |
|---|---|---|---|
| 6 | 4-Pentenoyl chloride | | 382.2228 |
| 7 | 2-Methylbutryl chloride | | 384.2391 |
| 8 | Isovaleryl chloride | | 384.2418 |
| 9 | Pentanoyl chloride | | 384.2419 |
| 10 | Methyloxalyl chloride | | 386.1835 |
| 11 | Isoxazole-5-carbonyl chloride | | 395.1826 |

-continued
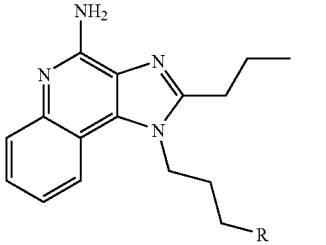
| Example | Acid Chloride | R | Measured Mass (M + H) |
|---|---|---|---|
| 12 | Cyclopentanecarbonyl chloride | 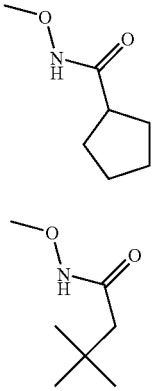 | 396.2420 |
| 13 | tert-Butylacetyl chloride | 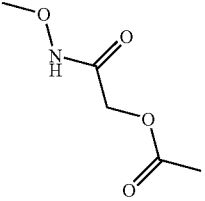 | 398.2581 |
| 14 | Acetoxyacetyl chloride | 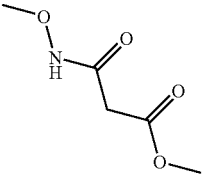 | 400.1979 |
| 15 | Methylmalonyl chloride | 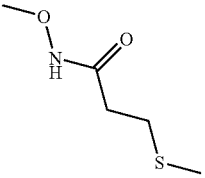 | 400.1965 |
| 16 | 3-Methylthiopropionyl chloride | 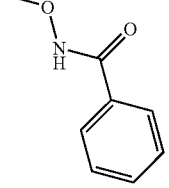 | 402.1950 |
| 17 | Benzoyl chloride | | 404.2097 |

-continued

| Example | Acid Chloride | R | Measured Mass (M + H) |
|---|---|---|---|
| 18 | Thiophene-2-carbonyl chloride | (methoxyamide of thiophene-2-carboxylic acid) | 410.1679 |
| 19 | Cyclohexanecarbonyl chloride | (methoxyamide of cyclohexanecarboxylic acid) | 410.2553 |
| 20 | (S)-(−)-2-Acetoxypropionyl chloride | (methoxyamide of (S)-2-acetoxypropionic acid) | 414.2162 |
| 21 | m-Toluoyl chloride | (methoxyamide of m-toluic acid) | 418.2261 |
| 22 | Phenylacetyl chloride | (methoxyamide of phenylacetic acid) | 418.2253 |
| 23 | 2-Fluorobenzoyl chloride | (methoxyamide of 2-fluorobenzoic acid) | 422.2006 |

-continued
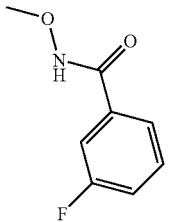
| Example | Acid Chloride | R | Measured Mass (M + H) |
|---|---|---|---|
| 24 | 3-Fluorobenzoyl chloride | 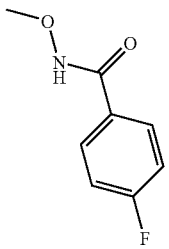 | 422.2020 |
| 25 | 4-Fluorobenzoyl chloride | 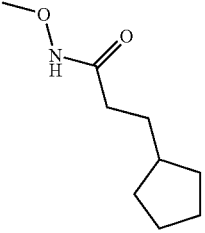 | 422.1982 |
| 26 | 3-Cyclopentylpropionyl chloride | 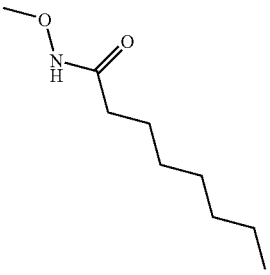 | 424.2731 |
| 27 | Octanoyl chloride | 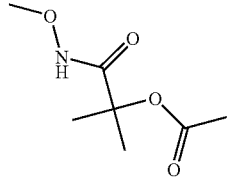 | 426.2857 |
| 28 | 2-Acetoxyisobutyryl chloride | | 428.2306 |

-continued
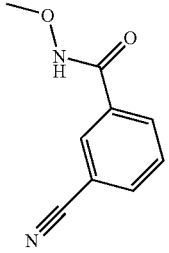
| Example | Acid Chloride | R | Measured Mass (M + H) |
|---|---|---|---|
| 29 | 3-Cyanobenzoyl chloride | 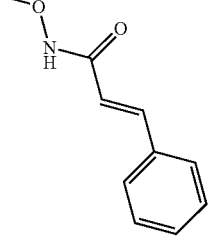 | 429.2063 |
| 30 | Cinnamoyl chloride | 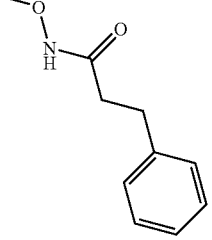 | 430.2243 |
| 31 | Hydrocinnamoyl chloride | 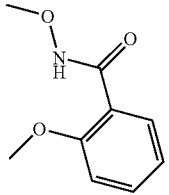 | 432.2374 |
| 32 | 2-Methoxybenzoyl chloride | 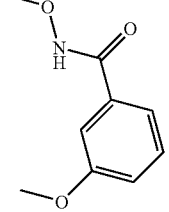 | 434.2227 |
| 33 | m-Anisoyl chloride |  | 434.2213 |

-continued
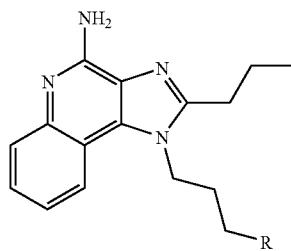
| Example | Acid Chloride | R | Measured Mass (M + H) |
|---|---|---|---|
| 34 | p-Anisoyl chloride | | 434.2217 |
| 35 | Phenoxyacetyl chloride | | 434.2197 |
| 36 | 3-Fluoro-4-methylbenzoyl chloride | | 436.2164 |
| 37 | 2-Chlorobenzoyl chloride | | 438.1688 |
| 38 | 3-Chlorobenzoyl chloride | | 438.1714 |

-continued
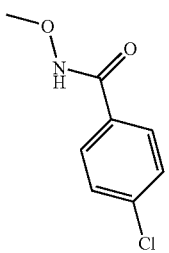
| Example | Acid Chloride | R | Measured Mass (M + H) |
|---|---|---|---|
| 39 | 4-Chlorobenzoyl chloride | 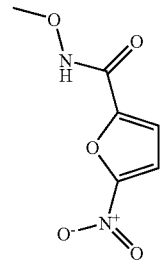 | 438.1705 |
| 40 | 5-Nitro-2-furoyl chloride | 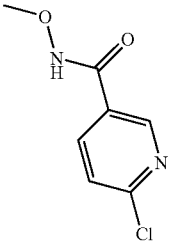 | 439.1762 |
| 41 | 6-Chloronicotinyl chloride | 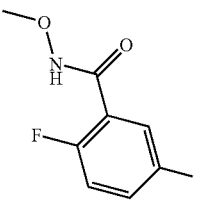 | 439.1685 |
| 42 | 2,5-Difluorobenzoyl chloride | 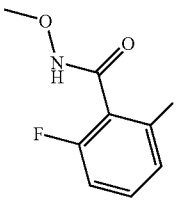 | 440.1900 |
| 43 | 2,6-Difluorobenzoyl chloride | | 440.1910 |

-continued

| Example | Acid Chloride | R | Measured Mass (M + H) |
|---|---|---|---|
| 44 | Methyladipoyl chloride | | 442.2446 |
| 45 | trans-2-Phenyl-1-cyclopropanecarbonyl chloride | | 444.2380 |
| 46 | 2-Phenylbutyryl chloride | | 446.2541 |
| 47 | 2-Phenoxypropionyl chloride | | 448.2361 |
| 48 | Benzyloxyacetyl chloride | | 448.2356 |

-continued
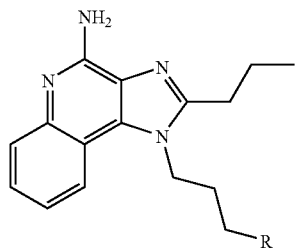
| Example | Acid Chloride | R | Measured Mass (M + H) |
|---|---|---|---|
| 49 | (Phenylthio)acetyl chloride | | 450.1978 |
| 50 | 2-(Methylthio)nicotinyl chloride | | 451.1892 |
| 51 | 1-Naphthoyl chloride | | 454.2273 |
| 52 | 2-Naphthoyl chloride | | 454.2226 |
| 53 | 4-n-Butylbenzoyl chloride | | 460.2684 |

-continued
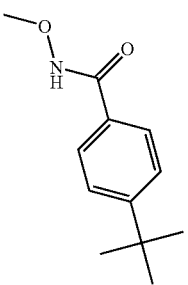
| Example | Acid Chloride | R | Measured Mass (M + H) |
|---|---|---|---|
| 54 | 4-tert-Butylbenzoyl chloride | 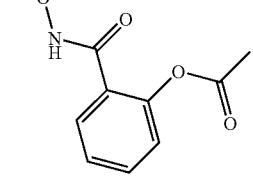 | 460.2740 |
| 55 | O-Acetylsalicyloyl chloride | 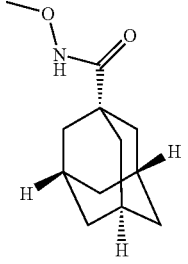 | 462.2137 |
| 56 | 1-Adamantanecarbonyl chloride | 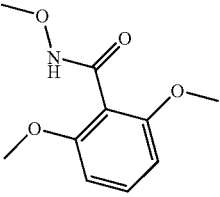 | 462.2875 |
| 57 | 2,6-Dimethoxybenzoyl chloride | | 464.2310 |
| 58 | 3,5-Dimethoxybenzoyl chloride | 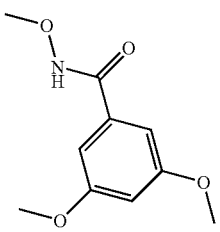 | 464.2317 |

-continued
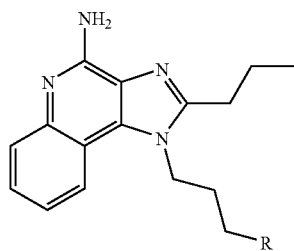
| Example | Acid Chloride | R | Measured Mass (M + H) |
|---|---|---|---|
| 59 | Methyl 8-chloro-8-oxooctanoate | *structure* | 470.2797 |
| 60 | 3-(Trifluoromethyl)-benzoyl chloride | *structure* | 472.1980 |
| 61 | 4-(Trifluoromethyl)-benzoyl chloride | *structure* | 472.1990 |
| 62 | 2,4-Dichlorobenzoyl chloride | *structure* | 472.1285 |

-continued
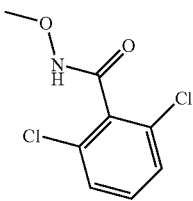
| Example | Acid Chloride | R | Measured Mass (M + H) |
|---------|---------------|---|-----------------------|
| 63 | 2,6-Dichlorobenzoyl chloride | 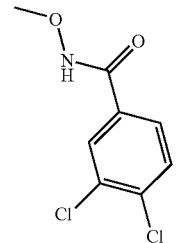 | 472.1296 |
| 64 | 3,4-Dichlorobenzoyl chloride | 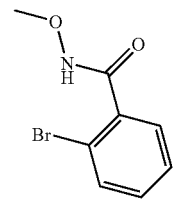 | 472.1337 |
| 65 | 2-Bromobenzoyl chloride | 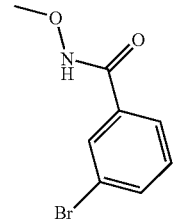 | 482.1191 |
| 66 | 3-Bromobenzoyl chloride | | 482.1184 |
| 67 | 4-(Trifluoromethoxy)-benzoyl chloride | 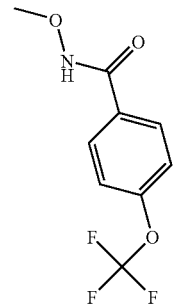 | 488.1936 |

-continued
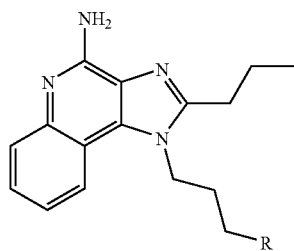
| Example | Acid Chloride | R | Measured Mass (M + H) |
|---|---|---|---|
| 68 | 2,4,6-Trichlorobenzoyl chloride | 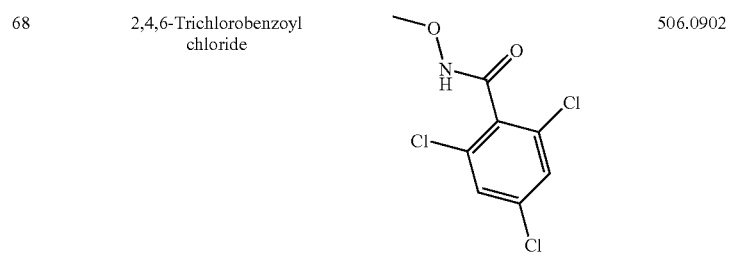 | 506.0902 |
| 69 | Benzenesulfonyl chloride | 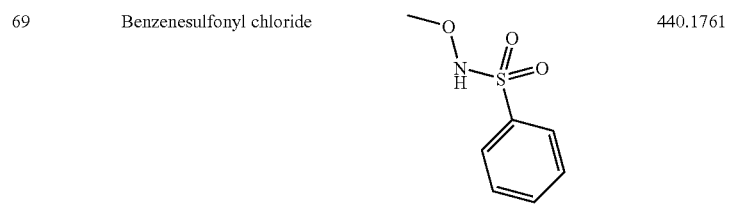 | 440.1761 |
| 70 | Methoxybenzenesulfonyl chloride | 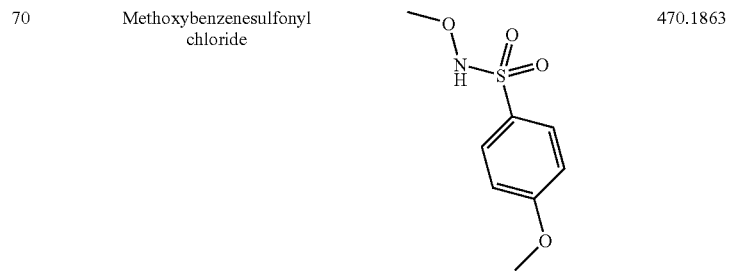 | 470.1863 |

Example 71

N-[4-(4-Amino-2-butyl-1H-imidazo[4,5-c]quinolin-1-yl)butoxy]-N'-phenylurea

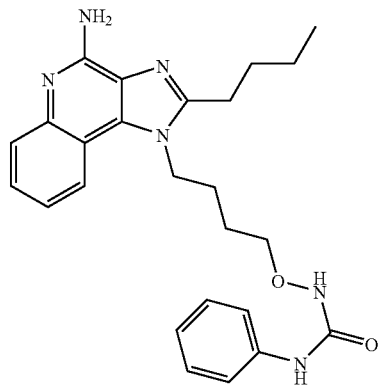

Part A

Triphenylphosphine (21.2 g, 80.7 mmol) and N-hydroxyphthalimide (13.2 g, 80.7 mmol) were added to a solution of 4-(2-butyl-1H-imidazo[4,5-c]quinolin-1-yl)butan-1-ol (16.0 g, 53.8 mmol) in tetrahydrofuran (200 mL). The mixture was stirred for five minutes and then was cooled to approximately 0° C. Diisopropyl azodicarboxylate (19.6 g, 96.8 mmol) was added dropwise, and the reaction was allowed to warm to room temperature and stirred for three hours. An analysis by LC/MS indicated the presence of starting material, and the reaction was stirred at 60° C. overnight. An analysis by LC/MS indicated the presence of starting material, and additional triphenylphosphine, N-hydroxyphthalimide, and diisopropyl azodicarboxylate (26.9 mmol of each) were added to the reaction mixture. The reaction was stirred at room temperature for two hours and heated at reflux for three hours. The reaction was concentrated under reduced pressure, and the residue was dissolved in chloroform (200 mL). The resulting solution was washed with brine (3×150 mL), dried over magnesium sulfate, filtered through a layer of CELITE filter aid, and concentrated under reduced pressure. An analysis of the crude product mixture by LC/MS indicated that starting material was still present. The mixture was dissolved in tetrahydrofuran (200 mL) and treated with triphenylphosphine (21.2 g, 80.7 mmol), N-hydroxyphthalimide (13.2 g, 80.7 mmol), and diisopropyl azodicarboxylate (19.6 g, 96.8 mmol) as described above. The reaction was stirred overnight at room temperature. The product was present as a white precipitate, which was isolated by filtration and washed with tetrahydrofuran to provide 8.68 g of 2-[4-(2-butyl-1H-imidazo[4,5-c]quinolin-1-yl)butoxy]-1H-isoindole-1,3(2H)-dione as a white solid.

$^1$H NMR (300 MHz, CDCl$_3$) δ 9.3 (s, 1H), 8.3 (m, 2H), 7.9 (m, 2H), 7.8 (m, 2H), 7.7 (m, 2H), 4.7 (t, J=7.9 Hz, 2H), 4.3 (t, J=5.8 Hz, 2H), 3.1 (t, J=7.6 Hz, 2H), 2.3 (m, 2H), 2.0 (m, 4H), 1.6 (m, 2H), 1.1 (t, J=7.3 Hz, 3H);

MS (APCI) m/z 443 (M+H)$^+$.

Part B

A solution of 2-[4-(2-butyl-1H-imidazo[4,5-c]quinolin-1-yl)butoxy]-1H-isoindole-1,3(2H)-dione (7.65 g, 17.3 mmol) in dichloromethane (100 mL) was treated with mCPBA (4.65 g, 20.7 mmol), and the resulting orange solution was stirred for four hours at room temperature. The solution was then diluted with dichloromethane (100 mL), washed with brine (3×100 mL), dried over magnesium sulfate, filtered through a layer of CELITE filter aid, and concentrated under reduced pressure to provide 9.92 g of 2-[4-(2-butyl-5-oxido-1H-imidazo[4,5-c]quinolin-1-yl)butoxy]-1H-isoindole-1,3(2H)-dione as a red semi-solid.

Part C

A mixture of 2-[4-(2-butyl-5-oxido-1H-imidazo[4,5-c]quinolin-1-yl)butoxy]-1H-isoindole-1,3(2H)-dione (8.92 g, 19.5 mmol) in dichloroethane (100 mL) was shaken vigorously until it became homogeneous. With vigorous stirring, ammonium hydroxide (100 mL) and 7-toluenesulfonyl chloride (4.45 g, 23.4 mmol) were added sequentially. The reaction was stirred overnight at room temperature. The product was present as a white precipitate, which was isolated by filtration to provide 1.97 g of 1-[4-(aminooxy)butyl]-butyl-1H-imidazo[4,5-c]quinolin-4-amine as a white solid.

$^1$H NMR (300 MHz, CDCl$_3$) δ 8.0 (d, J=8.2 Hz, 1H), 7.8 (d, J=8.3 Hz, 1H), 7.5 (t, J=7.1 Hz, 1H), 7.3 (t, J=7.1 Hz, 1H), 5.6 (br s, 2H), 5.2 (br s, 2H), 4.5 (t, J=7.8 Hz, 2H), 3.8 (t, J=6.2 Hz, 2H), 2.9 (t, J=7.6 Hz, 2H), 1.7-2.0 (m, 6H), 1.6 (m, 2H), 1.0 (t, 0.7=7.3 Hz, 3H);

MS (APCI) m/z 328 (M+H)$^+$.

The filtrate with diluted with chloroform, washed with brine (3×100 mL), dried over magnesium sulfate, filtered through a layer of CELITE filter aid, and concentrated under reduced pressure to provide 5.72 g additional product as a red semi-solid.

Part D

Triethylamine (495 μL, 3.55 mmol) and phenyl isocyanate (316 mg, 1.65 mmol) were added to a mixture of 1-[4-(aminooxy)butyl]-2-butyl-1H-imidazo[4,5-c]quinolin-4-amine (580 mg, 1.77 mmol) in chloroform (10 mL). The reaction was heated at 50° C. overnight and became homogeneous. The solution was diluted with 1 chloroform, washed with brine (2×), dried over magnesium sulfate, filtered through a layer of CELITE filter aid, and concentrated under reduced pressure to provide the crude product as an orange solid (700 mg). The crude product was purified by column chromatography on silica gel (eluting with dichloromethane:methanol in ratios ranging from 100:0 to 95:5) to provide 90 mg of N-[4-(4-amino-2-butyl-1H-imidazo[4,5-c]quinolin-1-yl)butoxy]-N'-phenylurea as a white solid.

HRMS (ESI) Theoretical mass: 447.2508, measured mass: 447.2497.

Example 72

2-Butyl-1-{4-[(isopropylamino)oxy]butyl}-1H-imidazo[4,5-c]quinolin-4-amine

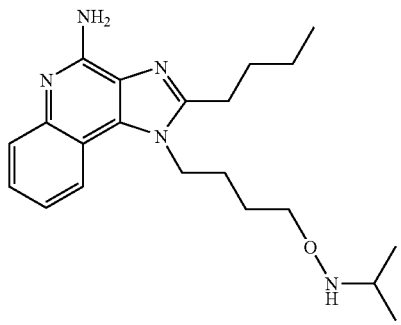

Part A

Acetone (444 mg, 7.65 mmol) was added to a solution of 1-[4-(aminooxy)butyl]-2-butyl-1H-imidazo[4,5-c]quinolin-4-amine (0.500 g, 1.53 mmol), prepared as described in Parts A-C of Example 71, in methanol (7 mL), and the reaction was stirred overnight at room temperature. The solvent was removed under reduced pressure and then further dried under high vacuum to provide 358 mg of acetone O-[4-(4-amino-2-butyl-1H-imidazo[4,5-c]quinolin-1-yl)butyl]oxime as a white solid, mp 115-117° C.

$^1$H NMR (300 MHz, DMSO-$d_6$) δ 8.0 (d, J=7.8 Hz, 1H), 7.7 (d, J=8.3 Hz, 1H), 7.5 (t, J=8.0 Hz, 1H), 7.3 (t, J=8.1 Hz, 1H), 6.5 (br s, 2H), 4.5 (t, J=7.2 Hz, 2H), 4.0 (t, J=6.0 Hz, 2H), 2.9 (t, J=7.5 Hz, 2H), 1.9-1.6 (m, 2H), 1.5 (m, 2H), 1.1 (t, J=7.3 Hz, 3H);

$^{13}$C NMR (75 MHz, DMSO-$d_6$) δ 154.2, 153.4, 152.0, 144.8, 132.6, 128.4, 126.6, 126.4, 121.5, 120.3, 115.1, 71.9, 44.9, 30.0, 26.8, 26.5, 25.9, 22.3, 21.6, 15.4, 14.1;

MS (APCI) m/z 368 (M+H)$^+$;

HRMS (ESI) Theoretical mass: 368.2469, measured mass: 368.2450.

Part B

Sodium cyanoborohydride (2 mL of a 1M solution in tetrahydrofuran) was added to a mixture of acetone O-[4-(4-(4-amino-2-butyl-1H-imidazo[4,5-c]quinolin-1-yl)butyl]oxime (358 mg, 0.974 mmol), methanol (5 mL), and acetic acid (2 mL). The reaction was stirred overnight at ambient temperature. A precipitate was present and was removed by filtration. The filtrate was diluted with chloroform, and the resulting solution was washed twice with brine, dried over magnesium sulfate, filtered through a layer of CELITE filter aid, and concentrated under reduced pressure. The crude product was purified by column chromatography on silica gel to provide 100 mg of 2-butyl-1-{4-[(isopropylamino)oxy]butyl}-1H-imidazo[4,5-c]quinolin-4-amine as an off-white solid.

HRMS (ESI) Theoretical mass: 370.2607, measured mass: 370.2600.

Examples 73-94

Part A

A solution of 2-(2-aminoethoxy)ethanol (30.3 g, 288 mmol) in a minimal amount of dichloromethane was added dropwise to a stirred mixture of 4-chloro-3-nitroquinoline (50.0 g, 240 mmol), potassium carbonate (33.1 g, 240 mmol), and triethylamine (36.4 g mL, 360 mmol) in DMF (200 mL) at 0° C. A yellow precipitate formed and more dichloromethane (several mL) was added. The mixture was allowed to warm to room temperature and stir overnight. A yellow solid was isolated by filtration, washed with water and dichloromethane, and dried. The filtrate was washed twice with brine, dried over magnesium sulfate, and filtered. Additional orange solid was isolated from the filtrate after concentration under reduced pressure. The solids were dried in a vacuum oven to afford 2-{2-[(3-nitroquinolin-4-yl)amino]ethoxy}ethanol.

Part B

A mixture of 2-{2-[(3-nitroquinolin-4-yl)amino]ethoxy}ethanol (66.2 g, 239 mmol) and 5% platinum on carbon (7.5 g) in ethanol (250 mL) was hydrogenated at approximately 30 psi (2.1×10$^5$ Pa) on a Parr apparatus overnight. Magnesium sulfate was added to the mixture, which was then filtered through CELITE filter agent. The filtrate was concentrated under reduced pressure to provide 43.0 g of crude 2-{2-[(3-aminoquinolin-4-yl)amino]ethoxy}ethanol as a yellow solid.

Part C

A mixture of 2-{2-[(3-aminoquinolin-4-yl)amino]ethoxy}ethanol (43.0 g, 155 mmol) and pyridine hydrochloride (1.79 g, 15.5 mmol) in toluene (200 mL) and dichloroethane (100 mL) was heated at reflux until a solution formed. The solution was allowed to cool to room temperature, then was cooled to 0° C. Triethyl orthopropionate (30.1 g, 171 mmol) was added and the mixture was heated at reflux for 3 hours. The solution was allowed to cool to room temperature and was concentrated under reduced pressure. The residue was diluted with chloroform, and 4 M NaOH was added to adjust the pH to 9. A solid formed. The mixture was filtered, and the isolated solid dissolved when it was washed with water and chloroform. The filtrate was transferred to a separatory funnel and washed twice with brine. The combined aqueous layers were back-extracted with dichloromethane. The combined organic layers were dried over magnesium sulfate, filtered, and concentrated to provide 40.0 g of 2-[2-(2-ethyl-1H-imidazo[4,5-c]quinolin-1-yl)ethoxy]ethanol as a tan solid.

Part D

The general procedure described in Part A of Example 1 was used to convert 2-[2-(2-ethyl-1H-imidazo[4,5-c]quinolin-1-yl)ethoxy]ethanol (35.6 g, 125 mmol) into 2-{2-[2-(2-ethyl-1H-imidazo[4,5-c]quinolin-1-yl)ethoxy]ethoxy}-1H-isoindole-1,3(2H)-dione. For the work-up, the solvent was removed and the residue was dissolved in chloroform (300 mL). To the solution was added 6 M HCl. Some of the solvent was removed from the mixture under reduced pressure, but the product did not precipitate so the mixture was transferred to a separatory funnel. The organic layer was removed. To the aqueous layer was added 6 M NaOH (240 mL), causing a precipitate to form. The mixture was extracted with chloroform three times. The later organic layers were combined, dried over magnesium sulfate, filtered, and concentrated under reduced pressure. The crude product was purified by flash chromatography (silica gel, gradient elution with 0-5% methanol in dichloromethane) to provide 11.0 g of 2-{2-[2-(2-ethyl-1H-imidazo[4,5-c]quinolin-1-yl)ethoxy]ethoxy}-1H-isoindole-1,3(2H)-dione.

Part E

To a solution of 2-{2-[2-(2-ethyl-1H-imidazo[4,5-c]quinolin-1-yl)ethoxy]ethoxy}-1H-isoindole-1,3(2H)-dione (11.0 g, 25.5 mmol) in chloroform (150 mL) was added mCPBA (11.4 g, 51.1 mmol). The solution was stirred at room temperature for 2 hours. Concentrated ammonium hydroxide (100 mL) was added, followed by p-toluenesulfonyl chloride (5.40 g, 28.1 mmol). The mixture was stirred overnight at room temperature. The mixture was transferred to a separatory funnel and was washed twice with 5% aqueous ammonium chloride and once with aqueous sodium carbonate solution, dried over magnesium sulfate, filtered, and concentrated under reduced pressure. The crude product was purified by flash chromatography (silica gel, gradient elution with 0-5% methanol in dichloromethane) to provide 6 g of 1-{2-[2-(aminooxy)ethoxy]ethyl}-2-ethyl-1H-imidazo[4,5-c]quinolin-4-amine.

Part F

A reagent from the table below (1.1 equivalents, 0.11 mmol) was added to a test tube containing a solution of 1-{2-[2-(aminooxy)ethoxy]ethyl}-2-ethyl-1H-imidazo[4,5-c]quinolin-4-amine (31 mg, 0.10 mmol) and triethylamine (28 μL, 0.20 mmol) in chloroform (1 mL). The test tubes were capped and placed on a shaker at ambient temperature overnight (approximately 18 hours). Two drops of water were added to each test tube, and the mixtures were vortexed. The solvent was removed from the test tubes by vacuum centrifugation.

The compounds were purified by prep HPLC using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the reagent used for each example, the structure of the resulting compound, and the observed accurate mass for the isolated trifluoroacetate salt.

Examples 73-94

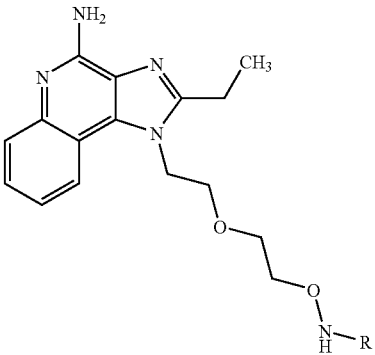

| Example | Reagent | R | Measured Mass (M + H) |
|---|---|---|---|
| 73 | Cyclopropanecarbonyl chloride | | 384.2067 |
| 74 | Benzoyl chloride | | 420.2043 |
| 75 | o-Toluoyl chloride | | 434.2214 |
| 76 | p-Toluoyl chloride | | 434.2198 |
| 77 | 2-Methoxybenzoyl chloride | | 450.2151 |
| 78 | 3-Methoxybenzoyl chloride | | 450.2173 |

-continued

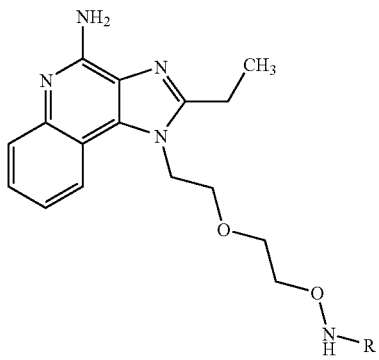

| Example | Reagent | R | Measured Mass (M + H) |
|---|---|---|---|
| 79 | 2-Chlorobenzoyl chloride | 2-chlorobenzoyl group | 454.1650 |
| 80 | Nicotinoyl chloride hydrochloride | nicotinoyl group | 421.2003 |
| 81 | Methanesulfonyl chloride | methanesulfonyl group | 394.1568 |
| 82 | Benzenesulfonyl chloride | benzenesulfonyl group | 456.1701 |
| 83 | 3-Methylbenzenesulfonyl chloride | 3-methylbenzenesulfonyl group | 470.1855 |
| 84 | o-Toluenesulfonyl chloride | o-toluenesulfonyl group | 470.1853 |
| 85 | p-Toluenesulfonyl chloride | p-toluenesulfonyl group | 470.1873 |

-continued

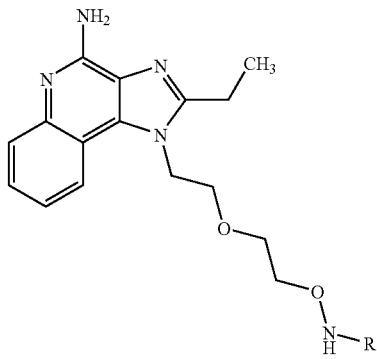

| Example | Reagent | R | Measured Mass (M + H) |
|---|---|---|---|
| 86 | 2-Fluorobenzenesulfonyl chloride | 2-fluorobenzenesulfonyl group | 474.1583 |
| 87 | 3-Fluorobenzenesulfonyl chloride | 3-fluorobenzenesulfonyl group | 474.1632 |
| 88 | 4-Fluorobenzenesulfonyl chloride | 4-fluorobenzenesulfonyl group | 474.1605 |
| 89 | 8-Quinolinesulfonyl chloride | 8-quinolinesulfonyl group | 507.1804 |
| 90 | Ethyl isocyanate | ethylcarbamoyl group | 387.2171 |
| 91 | N,N-Dimethylcarbamoyl chloride | N,N-dimethylcarbamoyl group | 387.2167 |
| 92 | Phenyl isocyanate | phenylcarbamoyl group | 435.2157 |

-continued

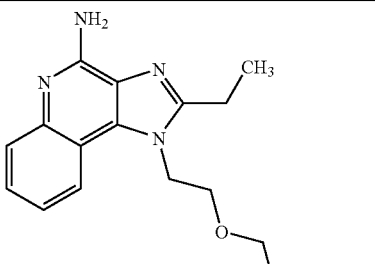

| Example | Reagent | R | Measured Mass (M + H) |
|---|---|---|---|
| 93 | o-Tolyl isocyanate | (structure: C(=O)NH-2-methylphenyl) | 449.2290 |
| 94 | N-Methyl-N-phenylcarbamoyl chloride | (structure: C(=O)N(CH3)phenyl) | 449.2339 |

Examples 95-104

Part A

The general procedure described in Part A of Example 1 was used to convert 3-[2-(methoxymethyl)-1H-imidazo[4,5-c]quinolin-1-yl]propan-1-ol (8.00 g, 29.5 mmol) into 2-{3-[2-(methoxymethyl)-1H-imidazo[4,5-c]quinolin-1-yl]propoxy}-1H-isoindole-1,3(2H)-dione. The work-up was similar to that described in Part A of Example 1, except that the precipitate obtained from the chloroform/6 M HQ mixture was purified by flash chromatography (silica gel, gradient elution with 0-7.5% methanol in dichloromethane) to provide 6.1 g of 2-{3-[2-(methoxymethyl)-1H-imidazo[4,5-c]quino-lin-1-yl]propoxy}-1H-isoindole-1,3(2H)-dione.

Part B

The general procedure described in Part E of Examples 73-94 was used to convert 2-{3-[2-(methoxymethyl)-1H-imidazo[4,5-c]quinolin-1-yl]propoxy}-1H-isoindole-1,3(2H)-dione (6.08 g, 14.6 mmol) into 712 mg of 1-[3-(aminooxy)propyl]-2-(methoxymethyl)-1H-imidazo[4,5-c]quinolin-4-amine. The product was purified by flash chromatography (silica gel, gradient elution with 0-10% methanol in dichloromethane).

Part C

A reagent from the table below (1.1 equivalents, 0.10 mmol) was added to a test tube containing a solution of 1-[3-(aminooxy)propyl]-2-(methoxymethyl)-1H-imidazo[4,5-c]quinolin-4-amine (27 mg, 0.9 mmol) and triethylamine (27 μL, 0.19 mmol) in DMF (1 mL). The test tubes were capped and placed on a shaker at ambient temperature overnight (approximately 18 hours). Two drops of water were added to each test tube, and the mixtures were vortexed. The solvent was removed from the test tubes by vacuum centrifugation. The compounds were purified as described for examples 73-94. The table below shows the reagent used for each example, the structure of the resulting compound, and the observed accurate mass for the isolated trifluoroacetate salt.

Examples 95-104

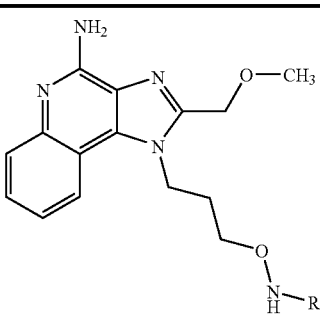

| Example | Reagent | R | Measured Mass (M + H) |
|---|---|---|---|
| 95 | Starting Material - No Reagent Added | H | 302.1640 |
| 96 | Acetyl chloride | C(=O)CH3 | 344.1734 |
| 97 | Cyclopropanecarbonyl chloride | C(=O)-cyclopropyl | 370.1913 |
| 98 | Nicotinoyl chloride hydrochloride | C(=O)-3-pyridyl | 407.1832 |
| 99 | Methanesulfonyl chloride | S(=O)2CH3 | 380.1407 |
| 100 | Dimethylsulfamoyl chloride | S(=O)2N(CH3)2 | 409.1692 |
| 101 | 1-Methylimidazole-4-sulphonyl chloride | S(=O)2-(1-methylimidazol-4-yl) | 446.1621 |

-continued

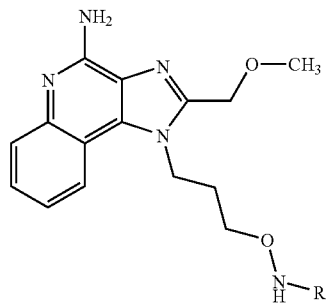

| Example | Reagent | R | Measured Mass (M + H) |
|---|---|---|---|
| 102 | Methyl isocyanate | —C(=O)—NH—CH₃ | 359.1844 |
| 103 | Phenyl isocyanate | —C(=O)—NH—C₆H₅ | 421.2004 |
| 104 | N,N-Dimethylcarbamoyl chloride | —C(=O)—N(CH₃)₂ | 373.1995 |

Examples 105-128

Part A

To a solution of 4-chloro-3-nitro[1,5]naphthyridine (18.0 g, 85.9 mmol) in dichloromethane (220 mL) at room temperature was added triethylamine (15.6 mL, 112 mmol) and 3-amino-1-butanol (7.20 mL, 94.5 mmol). The solution was stirred for 4 hours and then was concentrated under reduced pressure to yield an orange solid. The solid was slurried in water (250 mL) for 30 minutes, isolated by filtration, washed with water (3×30 mL), and dried at 70° C. in a vacuum oven to afford 20.9 g of 3-[(3-nitro[1,5]naphthyridin-4-yl)amino] propan-1-ol as a yellow solid.

Part B

Acetic anhydride (7.30 mL, 77.3 mmol) was added slowly to a 0° C. solution of 3-[(3-nitro[1,5]naphmyridin-4-yl) amino]propan-1-ol (16.0 g, 64.5 mmol), 4-dimethylaminopyridine (0.39 g, 3.2 mmol), and triethylamine (12.6 mL, 90.2 mmol) in dichloromethane (250 mL). The solution was stirred at 0° C. for 45 minutes, then was diluted with dichloromethane (50 mL) and washed with saturated aqueous sodium bicarbonate (150 mL). The aqueous layer was extracted with dichloromethane (2×40 mL). The organic layers were combined, dried over magnesium sulfate, filtered, and concentrated to afford 19.74 g of 3-[(3-nitro[1,5]naphthyridin-4-yl)amino]propyl acetate as a yellow solid, which contained a trace amount of triethylamine and acetic acid but was used without purification.

Part C

A mixture of 3-[(3-nitro[1,5]naphthyridin-4-yl)amino] propyl acetate (12.00 g, 41.3 mmol) and 5% platinum on carbon (1.2 g) in ethyl acetate (125 mL) was hydrogenated at 30 psi (2.1×10⁵ Pa) on a Parr apparatus for 3 hours. The mixture was filtered through CELITE filter agent, which was rinsed with ethyl acetate (100 mL). The filtrate was concentrated to 12.7 g of 3-[(3-amino[1,5]naphthyridin-4-yl)amino] propyl acetate as a golden oil.

Part D

Butyryl chloride (4.7 mL, 45.4 mmol) was added dropwise to a solution of 3-[(3-amino[1,5]naphthyridin-4-yl)amino] propyl acetate prepared in Part C in dichloromethane (160 mL) at 0° C. The solution was allowed to warm to room temperature and stir for 1 hour, then was concentrated under reduced pressure to provide 3-{[3-(butyrylamino)[1,5]naphthyridin-4-yl]amino}propyl acetate hydrochloride as a dark orange foam that was used directly in the next step.

Part E

To the 3-{[3-(butyrylamino)[1,5]naphthyridin-4-yl] amino}propyl acetate hydrochloride prepared in Part D was added ethanol (165 mL) and 2 M sodium hydroxide (62.0 mL, 124 mmol). The resulting solution was heated at 60° C. for 7 hours, and then was stirred at room temperature overnight. The solution was concentrated, and the resulting residue was dissolved in dichloromethane (250 mL) and washed with water (125 mL). The aqueous layer was extracted with dichloromethane (75 mL). The combined organic layers were washed with brine (100 mL), dried over magnesium sulfate, filtered, and concentrated to provide 9.24 g of 3-(2-propyl-1H-imidazo[4,5-c][1,5]naphthyridin-1-yl)propan-1-ol as a brown oil.

Part F

Diisopropyl azodicarboxylate (8.10 mL, 48.4 mmol) was added dropwise over ten minutes to a stirred solution of 3-(2-propyl-1H-imidazo[4,5-c][1,5]naphthyridin-1-yl)propan-1-ol (10.9 g, 40.3 mmol), triphenylphosphine (12.7 g, 48.4 mmol), and N-hydroxyphthalimide (7.89 g, 48.4 mmol) in tetrahydrofuran (160 mL) at 0° C. The reaction was allowed to warm to room temperature and was stirred overnight. The solvent was removed under reduced pressure to afford an oil that was dissolved in ethyl acetate (200 mL) and extracted with 2 M HCl (3×100 mL). The aqueous layers were combined, and solid sodium bicarbonate was added to adjust the pH to 7. A precipitate formed that was isolated by filtration and dissolved in dichloromethane (300 mL). The solution was dried over magnesium sulfate, filtered, and concentrated to afford 17.38 g of 2-[3-(2-propyl-1H-imidazo[4,5-c][1,5] naphthyridin-1-yl)propoxy]-1H-isoindole-1,3(2H)-dione as a tan solid.

Part G

To a solution of 2-[3-(2-propyl-1H-imidazo[4,5-c][1,5] naphthyridin-1-yl)propoxy]-1H-isoindole-1,3(2H)-dione (6.00 g, 14.4 mmol) in chloroform (70 mL) at room temperature was added 3-chloroperbenzoic acid (mCPBA, 3.37 g, 19.5 mmol). The reaction was stirred for 5 hours, and then concentrated ammonium hydroxide (40 mL) was added followed by portionwise addition of p-toluenesulfonyl chloride (3.03 g, 15.9 mmol). The mixture was stirred overnight and then was filtered to afford 3.99 g of crude product. The filtrate was diluted with brine (50 mL) and extracted with dichloromethane (2×20 mL). The organic layers were combined, dried over magnesium sulfate, filtered, and concentrated under reduced pressure to afford an orange solid, which was triturated with methanol and isolated by filtration to provide 0.450 g of product. The product was combined and purified by chromatography on a HORIZON HPFC system (an automated, modular high-performance flash purification product available from Biotage, Inc, Charlottesville, Va., USA)(silica gel, gradient elution with 0-35% CMA in chloroform where CMA is a solution of 80:18:2 chloroform:methanol:concentrated ammonium hydroxide) to afford 2.23 g of 1-[3-(aminooxy)propyl]-2-propyl-1H-imidazo[4,5-c][1,5]naphthyridin-4-amine as a pale yellow solid.

Part H

An reagent from the table below (1.1 equivalents, 0.11 mmol) was added to a test tube containing a solution of 1-[3-(aminooxy)propyl]-2-propyl-1H-imidazo[4,5-c][1,5]naphthyridin-4-amine (30 mg, 0.10 mmol) and triethylamine (29 μL, 0.20 mmol) in chloroform (1 mL). The test tubes were capped and placed on a shaker at ambient temperature overnight (approximately 18 hours). Two drops of water were added to each test tube, and the mixtures were vortexed. The solvent was removed from the test tubes by vacuum centrifugation.

The compounds were purified as described for examples 73-94. The table below shows the reagent used for each example, the structure of the resulting compound, and the observed accurate mass for the isolated trifluoroacetate salt.

Examples 105-128

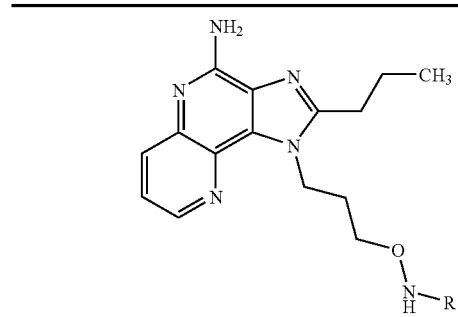

| Example | Reagent | R | Measured Mass (M + H) |
|---|---|---|---|
| 105 | No Reagent Added - Starting Material Only | —H | 301.1771 |
| 106 | Acetyl chloride | (CH₃C(O)—) | 343.1873 |
| 107 | Methyl chloroformate | (—C(O)OCH₃) | 359.1843 |
| 108 | Cyclopropanecarbonyl chloride | (cyclopropyl-C(O)—) | 369.2055 |
| 109 | Benzoyl chloride | (PhC(O)—) | 405.2065 |
| 110 | m-Toluoyl chloride | (3-CH₃-C₆H₄-C(O)—) | 419.2196 |
| 111 | p-Toluoyl chloride | (4-CH₃-C₆H₄-C(O)—) | 419.2222 |
| 112 | 3-Methoxybenzoyl chloride | (3-CH₃O-C₆H₄-C(O)—) | 435.2176 |
| 113 | p-Anisoyl chloride | (4-CH₃O-C₆H₄-C(O)—) | 435.2151 |
| 114 | 3-Chlorobenzoyl chloride | (3-Cl-C₆H₄-C(O)—) | 439.1668 |

| Example | Reagent | R | Measured Mass (M + H) |
|---|---|---|---|
| 115 | 4-Chlorobenzoyl chloride | 4-chlorobenzoyl group | 439.1639 |
| 116 | Nicotinoyl chloride hydrochloride | nicotinoyl group (3-pyridyl C=O) | 406.2010 |
| 117 | Benzenesulfonyl chloride | phenylsulfonyl group | 441.1716 |
| 118 | 1-Methylimidazole-4-sulphonyl chloride | 1-methylimidazole-4-sulfonyl group | 445.1772 |
| 119 | 3-Methylbenzene-sulfonyl chloride | 3-methylphenylsulfonyl group | 455.1860 |
| 120 | 3-Fluorobenzene-sulfonyl chloride | 3-fluorophenylsulfonyl group | 459.1635 |
| 121 | 4-Fluorobenzene-sulfonyl chloride | 4-fluorophenylsulfonyl group | 459.1634 |
| 122 | 8-Quinolinesulfonyl chloride | 8-quinolinylsulfonyl group | 492.1815 |
| 123 | Ethyl isocyanate | ethylaminocarbonyl group | 372.2164 |
| 124 | Phenyl isocyanate | phenylaminocarbonyl group | 420.2165 |
| 125 | Cyclohexyl isocyanate | cyclohexylaminocarbonyl group | 426.2618 |

113

-continued

| Example | Reagent | R | Measured Mass (M + H) |
|---|---|---|---|
| 126 | p-Tolyl isocyanate | (amide with 4-methylphenyl) | 434.2299 |
| 127 | 2-Phenyl ethylisocyanate | (amide with phenethyl) | 448.2454 |
| 128 | N-Methyl-N-phenylcarbamoyl chloride | (N-methyl-N-phenyl amide) | 434.2302 |

Example 129

6,7-Dimethyl-1-(3-{[(1-phenylethyl)amino]oxy}propyl)-2-propyl-1H-imidazo[4,5-c]pyridin-4-amine

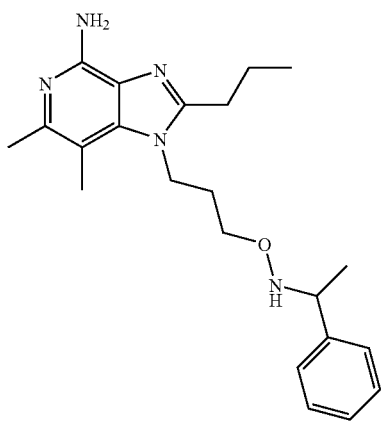

114

Part A

3-Amino-1-propanol (6.92 mL, 90.5 mmol) was added dropwise to a stirred solution of 2,4-dichloro-5,6-dimethyl-3-nitropyridine (20.0 g, 90.5 mmol) and triethylamine (18.9 mL, 136 mmol) in DMF (300 mL) at room temperature. After 16 hours, the solvent was removed under reduced pressure and the resulting oil was partitioned between ethyl acetate (450 mL) and water (50 mL). The layers were separated and the organic layer was washed with water (3×50 mL). The combined aqueous layers were back-extracted with ethyl acetate (2×30 mL). The combined organic layers were dried over magnesium sulfate, filtered, and concentrated under reduced pressure. The resulting orange solid was triturated with hexanes/ethyl acetate (2:1) and was isolated by filtration to yield 12.43 g of 3-[(2-chloro-5,6-dimethyl-3-nitropyridin-4-yl)amino]propan-1-ol as a yellow solid.

Part B

A mixture of 3-[(2-chloro-5,6-dimethyl-3-nitropyridin-4-yl)amino]propan-1-ol (12.4 g, 47.8 mmol), sodium azide (6.20 g, 95.5 mmol), and cerium (III) chloride heptahydrate (8.90 g, 23.9 mmol) in 9:1 acetonitrile:water (160 mL) was heated at reflux for 16 hours, then was allowed to cool to room temperature. DMF was added and the mixture was filtered. The filter cake was washed with DMF. The filtrate was concentrated under reduced pressure to give an orange solid that was triturated with ethyl acetate and isolated by filtration to yield 9.60 g of 3-[(5,6-dimethyl-8-nitrotetraazolo[1,5-α]pyridin-7-yl)amino]propan-1-ol as a yellow solid.

Part C

A mixture of 3-[(5,6-dimethyl-8-nitrotetraazolo[1,5-α]pyridin-7-yl)amino]propan-1-ol (4.00 g, 15.0 mmol) and 10% palladium on carbon (0.40 g) in acetonitrile (75 mL) was hydrogenated at 50 psi (3.5×10$^5$ Pa) on a Parr apparatus for 16 hours. The mixture was filtered through CELITE filter agent, which was rinsed with methanol. The filtrate was concentrated under reduced pressure to yield 3.48 g of 3-[(8-amino-5,6-dimethyltetraazolo[1,5-α]pyridin-7-yl)amino]propan-1-ol.

Part D

A mixture of 3-[(8-amino-5,6-dimethyltetraazolo[1,5-α]pyridin-7-yl)amino]propan-1-ol (3.45 g, 14.6 mmol), pyridine hydrochloride (0.64 g, 5.5 mmol) and trimethyl orthobutyrate (2.60 mL, 16.1 mmol) in toluene (100 mL) was heated to reflux. Additional trimethyl orthobutyrate (1.1 equivalents) was added. The mixture was heated at reflux for 16 hours. The mixture was allowed to cool to room temperature, and 3.21 g of the product, 3-(5,6-dimethyl-8-propyl-7H-imidazo[4,5-c]tetraazolo[1,5-α]pyridin-7-yl)propan-1-ol, was isolated by filtration.

Part E

Diisopropyl azodicarboxylate (372 μL, 1.89 mmol) was added to a stirred solution of 3-(5,6-dimethyl-8-propyl-7H-imidazo[4,5-c]tetraazolo[1,5-α]pyridin-7-yl)propan-1-ol (500 mg, 1.72 mmol), triphenylphosphine (496 mg, 1.89 mmol), and N-hydroxyphthalimide (308 mg, 1.89 mmol) in DMF (17 mL) at room temperature. After 4 hours, the solvent was removed under reduced pressure to afford an oil that was triturated with ethyl acetate to generate a pink solid. The solid was isolated by filtration and washed with ethyl acetate to yield 630 mg of 2-[3-(5,6-dimethyl-8-propyl-7H-imidazo[4,5-c]tetraazolo[1,5-α]pyridin-7-yl)propoxy]-1H-isoindole-1,3(2H)-dione as a pink powder.

Part F

A solution of 2-[3-(5,6-dimethyl-8-propyl-7H-imidazo[4,5-c]tetraazolo[1,5-α]pyridin-7-yl)propoxy]-1H-isoindole-1, 3(2H)-dione (8.50 g, 19.6 mmol) and triphenylphosphine (10.3 g, 39.2 mmol) in 1,2-dichlorobenzene (200 mL) was heated at 125° C. for 2 days, then was allowed to stand at room temperature for 3 days. The solvent was removed under reduced pressure. To the resulting residue was added methanol (40 mL) and 1 M HCl (20 mL). The solution was heated at 50° C. for 5 h, then was allowed to cool to room temperature and was concentrated under reduced pressure. Water (20 mL) was added and the mixture was extracted with chloroform (3×10 mL). NaOH (1 M) was added to the aqueous layer to adjust the pH to 11. The aqueous layer was extracted with chloroform (4×30 mL). The combined organic layers were dried over sodium sulfate, filtered, and concentrated under reduced pressure. The crude product was purified by chromatography on a HORIZON HPFC system (silica gel, gradient elution with CMA in chloroform) to yield 1.00 g of 1-[3-(aminooxy)propyl]-6,7-dimethyl-2-propyl-1H-imidazo[4,5-c]pyridin-4-amine.

Part G

A solution of 1-[3-(aminooxy)propyl]-6,7-dimethyl-2-propyl-1H-imidazo[4,5-c]pyridin-4-amine (0.64 g, 2.3 mmol) and acetophenone (325 µL, 2.76 mmol) in methanol (23 mL) was stirred overnight at room temperature, then heated at 50° C. for 4 hours. Pyridine hydrochloride (100 mg) was added to the solution and stirring was continued at 50° C. overnight. Additional pyridine hydrochloride was added and the solution was heated at reflux for 5 hours. The solvent was removed under reduced pressure and the resulting off-white solid was partitioned between chloroform (100 mL) and saturated aqueous sodium carbonate (30 mL). The aqueous layer was extracted with chloroform (3×30 mL). The combined organic layers were washed with saturated aqueous sodium carbonate (2×20 mL), dried over sodium sulfate, filtered, and concentrated under reduced pressure. The crude product was purified by chromatography on a HORIZON HPFC system (silica gel, gradient elution with 5-30% CMA in chloroform) to yield a solid that was triturated with acetonitrile and dried under vacuum at 70° C. overnight to provide 105 mg of (1E)-1-phenylethanone O-[3-(4-amino-6,7-dimethyl-2-propyl-1H-imidazo[4,5-c]pyridin-1-yl)propyl]oxime as a white powder, mp 125.0-127.0° C. Anal. Calcd for $C_{22}H_{29}N_5O$: C, 69.63; H, 7.70; N, 18.45. Found: C, 69.41; H, 7.73; N, 18.36.

The product was obtained as a 9:1 mixture of E:Z isomers.

Part H

A solution of sodium cyanoborohydride in tetrahydrofuran (1 M, 16 mL, 16 mmol) was added to a solution of (1E)-1-phenylethanone ([3-(4-amino-6,7-dimethyl-2-propyl-1H-imidazo[4,5-c]pyridin-1-yl)propyl]oxime (620 mg, 1.63 mmol) in methanol (16 mL) and acetic acid (8 mL) at room temperature. The solution was stirred for 4 days and more acetic acid (4 mL) and sodium cyanoborohydride in tetrahydrofuran (1 M, 5 mL) were added. After stirring overnight, the solution was heated at 50° C. for 1 day. The solution was concentrated under reduced pressure, and then acetic acid was added until the reaction solution was pH 4. Additional methanol (16 mL) and sodium cyanoborohydride in tetrahydrofuran (1 M, 16 mL) were added as well. The reaction was stirred overnight, and methyl orange was added. To the yellow solution was added concentrated hydrochloric acid until the solution was red. The reaction was stirred for 3 days at room temperature and then was heated at 50° C. for 1 day. More sodium cyanoborohydride in tetrahydrofuran (1 M, 10 mL) was added and the reaction was stirred at room temperature for 5 days. The reaction mixture was filtered, and the filter cake was washed with methanol. The filtrate was concentrated under reduced pressure. The residue was partitioned between chloroform (30 mL) and saturated aqueous sodium bicarbonate (10 mL). To the mixture was added 1 M aqueous sodium hydroxide to adjust the pH to 10. The phases were separated and the aqueous phase was extracted with chloroform (3×10 mL). The organic fractions were combined, washed with saturated aqueous sodium bicarbonate, dried over sodium sulfate, filtered, and concentrated under reduced pressure. The crude product was purified twice by chromatography on a HORIZON HPFC system (silica gel, gradient elution with 5-30% CMA in chloroform, then 5-25% CMA in chloroform) to afford 6,7-dimethyl-1-(3-{[(1-phenylethyl)amino]oxy}propyl)-2-propyl-1H-imidazo[4,5-c]pyridin-4-amine as a yellow oil.

HRMS (EI) Calcd. for $C_{22}H_{31}N_5O$: 382.2607, found 382.2608.

Example 130

1-{3-[(Isopropylamino)oxy]propyl}-2-propyl-1H-imidazo[4,5-c]quinolin-4-amine

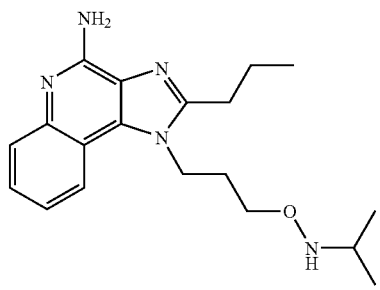

Part A

A mixture of 1-[3-(aminooxy)propyl]-2-propyl-1H-imidazo[4,5-c]quinolin-4-amine (prepared as described in Example 1, 0.605 g, 2.02 mmol) in methanol was heated until the starting material dissolved. Acetone (3 mL, 40 mmol) was then added, and the resulting solution was stirred for two hours. The reaction was then concentrated under reduced pressure, and the residue (800 mg) was purified by column chromatography on silica gel (25 g, eluting sequentially with 98:2 dichloromethane:methanol and 95:5 dichloromethane:methanol) to provide 600 mg of acetone O-[3-(4-amino-2-propyl-1H-imidazo[4,5-c]quinolin-1-yl)propyl]oxime as a beige powder, mp 147-150° C.

Anal. Calcd. for $C_{19}H_{25}N_5O \cdot 0.35H_2O$: C, 66.00; H, 7.49; N, 20.26. Found: C, 66.34; H, 7.34; N, 19.88.

Part B

Acetic acid (10 mL) followed by 1 M sodium cyanoborohydride in tetrahydrofuran (11.05 mL, 11.05 mmol) was added to a stirred solution of acetone O-[3-(4-amino-2-propyl-1H-imidazo[4,5-c]quinolin-1-yl)propyl]oxime (1.50 g, 4.42 mmol) in methanol (10 mL). The reaction was stirred overnight at room temperature and then was concentrated under reduced pressure. The residue was diluted with water (100 mL) and the pH was adjusted with solid sodium hydroxide to pH 6. The mixture was extracted with chloroform (2×100 mL). The organic layers were combined, dried over magnesium sulfate, filtered, and concentrated under reduced pressure to yield 1.31 g of 1-{3-[(isopropylamino)oxy]propyl}-2-propyl-1H-imidazo[4,5-c]quinolin-4-amine.

MS (APCI) m/z 342 (M+H)⁺.

Examples 131-136

A reagent from the table below (1.1 equivalents, 0.11 mmol) was added to a test tube containing a solution of 1-{3-[(isopropylamino)oxy]propyl}-2-propyl-1H-imidazo[4,5-c]quinolin-4-amine (34 mg, 0.10 mmol) and N,N-diisopropylethylamine (22 μL, 0.12 mmol) in chloroform (2 mL). The test tubes were capped and placed on a shaker at ambient temperature overnight (approximately 18 hours). The solvent was removed from the test tubes by vacuum centrifugation.

The compounds were purified as described for Examples 73-94. The table below shows the reagent used for each example, the structure of the resulting compound, and the observed accurate mass for the isolated trifluoroacetate salt.

Examples 131-136

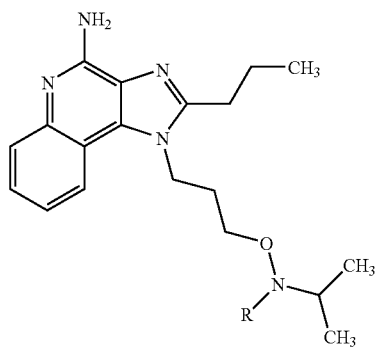

| Example | Reagent | R | Measured Mass (M + H) |
|---|---|---|---|
| 131 | Acetyl chloride | | 384.2426 |
| 132 | Methoxyacetyl chloride | | 414.2527 |
| 133 | Methyl oxalyl chloride | | 428.2288 |
| 134 | Isoxazole-5-carbonyl chloride | | 437.2271 |
| 135 | Methyl malonyl chloride | | 442.2439 |
| 136 | (1H-Indol-3-yl)-oxo-acetyl chloride | | 513.2630 |

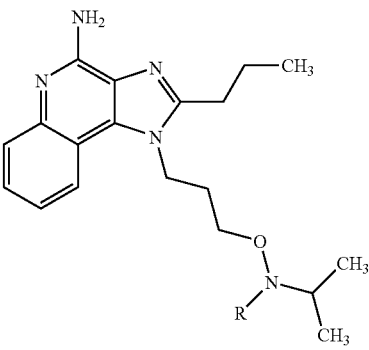

Example 137

N-[3-(4-Amino-7-bromo-2-propyl-1H-imidazo[4,5-c]quinolin-1-yl)propoxy]-2-methylpropanamide

Part A

A mixture of triethyl orthoformate (154 g, 1.04 mol) and 2,2-dimethyl-1,3-dioxane-4,6-dione (Meldrum's acid, 142 g, 0.983 mol) was heated to 55° C. for 4 hours. After cooling to 50° C., a solution of 3-bromoaniline (162.6 g, 0.945 mol) in ethanol (300 mL) was added such that the temperature of the reaction was maintained between 50-55° C. After half of the 3-bromoaniline had been added, stirring became difficult due to the formation of solids, so more ethanol (1 L) was added to facilitate stirring. Upon complete addition, the reaction was cooled to room temperature, and the solids were collected by filtration. The filter cake was washed with ice cold ethanol until the washings were nearly colorless, and the product was dried at 65° C. under vacuum to afford 287 g of 5-[(3-bromophenylimino)methyl]-2,2-dimethyl-1,3-dioxane-4,6-dione as an off-white solid.

$^1$H NMR (300 MHz, CDCl$_3$) δ 11.19 (brd, J=12.8 Hz, 1H), 8.60 (d, J=14.0 Hz, 1H), 7.44-7.38 (m, 2H), 7.30 (t, J=8.0 Hz, 1H), 7.18 (ddd, J=8.0, 2.2, 0.9 Hz, 1H), 1.75 (s, 6H).

Part B

7-Bromoquinolin-4-ol was prepared in accordance with the literature procedure (D. Dibyendu et al., *J. Med. Chem.*, 41, 4918-4926 (1998)) or by thermolysis of 5-[(3-bromophenylimino)methyl]-2,2-dimethyl-1,3-dioxane-4,6-dione in DOWTHERM A heat transfer fluid and had the following spectral properties:

$^1$H NMR (300 MHz, d$_6$-DMSO) δ 11.70 (brs, 1H), 8.00 (d, J=8.7 Hz, 1H), 7.92 (d, J=7.5 Hz, 1H), 7.74 (d, J=1.9 Hz, 1H), 7.44 (dd, J=8.7, 1.9 Hz, 1H), 6.05 (d, J=7.5 Hz, 1H).

Part C

A stirred suspension of 7-bromoquinolin-4-ol (162 g, 0.723 mol) in propionic acid (1500 mL) was brought to 110° C. Nitric acid (85 g of 70%) was added dropwise over 1 hour such that the temperature was maintained between 110-115° C. After half of the nitric acid had been added, stirring became difficult due to the formation of solids and an additional 200 mL of propionic acid was added. Upon complete addition, the reaction was stirred for 1 hour at 110° C., cooled to room temperature, and the solid was collected by filtration. The filter cake was washed with ice cold ethanol until the washings were nearly colorless (800 mL), and the product was dried at 60° C. under vacuum to afford 152 g of 7-bromo-3-nitroquinolin-4-ol as a pale yellow solid.

$^1$H NMR (300 MHz, d$_6$-DMSO) δ 13.0 (brs, 1H), 9.22 (s, 1H), 8.15 (d, J=8.4 Hz, 1H), 7.90 (d, J=1.6 Hz, 1H), 7.66 (dd, J=8.7, 1.9 Hz, 1H).

Part D

7-Bromo-3-nitroquinolin-4-ol (42 g, 156 mmol) was suspended in POCl$_3$ (130 mL) and brought to 102° C. under an atmosphere of N2. After 45 min, all of the solids had dissolved, so the reaction was cooled to room temperature. The resulting solids were collected by filtration, washed with H$_2$O, and then partitioned with CH$_2$Cl$_2$ (3 L) and 2M Na$_2$CO$_3$ (500 mL). The organic layer was separated, washed with H$_2$O (1×), dried over Na$_2$SO$_4$, filtered, and concentrated under reduced pressure to afford 33.7 g of 7-bromo-4-chloro-3-nitroquinoline as a beige solid.

$^1$H NMR (300 MHz, CDCl$_3$) δ 9.26 (s, 1H), 8.41 (d, J=1.8 Hz, 1H), 8.30 (d, J=9.0 Hz, 1H), 7.90 (dd, J=8.9, 2.1 Hz, 1H).

Part E

To a solution of 7-bromo-4-chloro-3-nitroquinoline (10.00 g, 34.78 mmol) in dichloromethane (140 mL) was added triethylamine (10.2 mL, 73.1 mmol). The solution was cooled to 0° C., and 3-amino-1-butanol (2.80 mL, 36.5 mmol) was added. The solution was stirred overnight at ambient temperature and then filtered to collect a precipitate. The precipitate was washed with dichloromethane and water. The filtrate was washed with saturated aqueous sodium bicarbonate and then added to the precipitate. The mixture was concentrated under reduced pressure. Methanol and toluene were added several times and removed under reduced pressure. The resulting solid was dried under high vacuum to provide 11.34 g of 3-[(7-bromo-3-nitroquinolin-4-yl)amino]propan-1-ol as a yellow solid.

Part F

A solution of sodium dithionate (27.5 g, 158 mmol) in water (60 mL) was added to a solution of 3-[(7-bromo-3-nitroquinolin-4-yl)amino]propan-1-ol (10.3 g, 31.6 mmol) in ethanol (175 mL), and the mixture was stirred vigorously for four hours at ambient temperature. The solvent was removed under reduced pressure, and the residue was partitioned between dichloromethane/chloroform/methanol (500 mL) and saturated aqueous sodium bicarbonate (200 mL). The aqueous layer was separated and extracted with chloroform (5×200 mL), and the combined organic fractions were dried over sodium sulfate, filtered, and concentrated under reduced pressure to provide 7.27 g of 3-[(3-amino-7-bromoquinolin-4-yl)amino]propan-1-ol.

Part G

A mixture of 3-[(3-amino-7-bromoquinolin-4-yl)amino]propan-1-ol (7.2 g, 24 mmol), pyridine hydrochloride (1.05 g, 9.09 mmol) and trimethyl orthobutyrate (4.05 mL, 25.5 mmol) in toluene (240 mL) was heated at reflux for two hours under an atmosphere of nitrogen. The solvent was removed under reduced pressure, and the residue was dissolved in methanol (100 mL). Aqueous sodium hydroxide (15 mL of 6 M) was added to the solution, and the resulting mixture was stirred for two hours at ambient temperature. A portion of the solvent was removed under reduced pressure, and the resulting mixture was adjusted to pH 7 with the addition of 6 N hydrochloric acid. The mixture was then extracted with chloroform (4×150 mL), and the combined extracts were washed sequentially with saturated aqueous sodium bicarbonate (40 mL) and brine (30 mL), dried over magnesium sulfate, filtered, and concentrated under reduced pressure. An analysis by nuclear magnetic resonance spectroscopy indicated the presence of starting material, and the procedure was repeated using 1 mL trimethyl orthobutyrate and heating at reflux for one hour. Following the work-up procedure, the resulting solid was triturated with ethyl acetate and isolated by filtration to provide 7.30 g of 3-(7-bromo-2-propyl-1H-imidazo[4,5-c]quinolin-1-yl)propan-1-ol.

Part H

A modification of the method described in Part A of Example 1 was followed using 3-(7-bromo-2-propyl-1H-imidazo[4,5-c]quinolin-1-yl)propan-1-ol (4.60 g, 13.2 mmol), triphenylphosphine (4.17 g, 15.9 mmol), diisopropyl azodicarboxylate (3.13 mL, 15.9 mmol), and Y-hydroxyphthalimide (2.59 g, 15.9 mmol). After the solvent was removed under reduced pressure, the residue was dissolved in chloroform (200 mL), washed sequentially with saturated aqueous sodium bicarbonate (2×30 mL) and brine (20 mL), dried over magnesium sulfate, filtered, and concentrated under reduced pressure. The crude product was triturated twice with ethyl acetate to provide 4.68 g of 2-[3-(7-bromo-2-propyl-1H-imidazo[4,5-c]quinolin-1-yl)propoxy]-1H-isoindole-1,3 (2H)-dione.

Part I

To a solution of 2-[3-(7-bromo-2-propyl-1H-imidazo[4,5-c]quinolin-1-yl)propoxy]-1H-isoindole-1,3(2H)-dione (1.00 g, 2.03 mmol) in chloroform (20 mL) at room temperature and under an atmosphere of nitrogen was added mCPBA (1.00 g, 4.06 mmol). The reaction was stirred for 2 hours, then was cooled to 0° C. Concentrated ammonium hydroxide (1 mL) was added followed by p-toluenesulfonyl chloride (111 mg, 0.58 mmol) in portions. The mixture was stirred for 1.5 hours at 0° C. and then filtered to remove a solid, which was washed with chloroform. The filtrate was washed with brine (2×10 mL), dried over sodium sulfate, filtered, and concentrated under reduced pressure. The crude product was purified by chromatography on a HORIZON HPFC system (silica gel, gradient elution with 0-35% CMA in chloroform) to afford 300 mg of 1-[3-(aminooxy)propyl]-7-bromo-2-propyl-1H-imidazo[4,5-c]quinolin-4-amine.

Part J

Triethylamine (120 μL), 0.86 mmol) was added to a solution of 1-[3-(aminooxy)propyl]-2-propyl-1H-imidazo[4,5-c]quinolin-4-amine (300 mg, 0.79 mmol) in 1-methyl-2-pyrrolidinone at −5° C. Isobutyryl chloride (83 μL, 0.79 mmol) was then added and the solution was stirred for 3 hours at room temperature. The reaction was diluted with chloroform (200 mL), washed with water (2×30 mL) and brine (20 mL), dried over sodium sulfate, filtered, and concentrated under reduced pressure. The crude product was triturated with acetonitrile and then recrystallized from ethyl acetate. A portion of the product (55 mg) was recrystallized from acetonitrile, triturated with dichloromethane, and dried under vacuum at 100° C. overnight to provide 34 mg of N-[3-(4-amino-7-bromo-2-propyl-1H-imidazo[4,5-c]quinolin-1-yl)propoxy]-2-methylpropanamide as a white powder, mp 176.0-178.0° C.

Anal. Calcd for $C_{20}H_{26}BrN_5O_2$: C, 53.58; H, 5.85; N, 15.62. Found: C, 53.26; H, 5.75; N, 15.29.

Example 138

N-[3-(4-Amino-7-phenyl-2-propyl-1H-imidazo[4,5-c]quinolin-1-yl)propoxy]-2-methylpropanamide

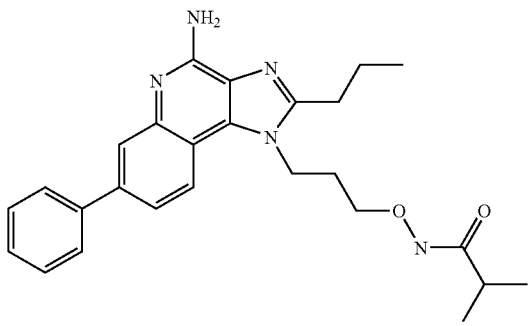

Under a nitrogen atmosphere, N-[3-(4-amino-7-bromo-2-propyl-1H-imidazo[4,5-c]quinolin-1-yl)propoxy]-2-methylpropanamide (300 mg, 0.67 mmol), phenylboronic acid (123 mg, 1.01 mmol), a solution of palladium (II) acetate (1.5 mg, 0.0067 mmol) in hot toluene (0.2 mL), triphenylphosphine (5.3 mg, 0.02 mmol), and 2 M aqueous sodium carbonate (0.4 mL, 0.8 mmol) were combined in 5:1 n-propanol:water (1.44 mL). The solution was placed under vacuum and back-filled with nitrogen gas three times and then heated at 100° C. for 16 hours. Additional phenylboronic acid (123 mg, 1.01 mmol), palladium (II) acetate (1.5 mg, 0.0067 mmol), and triphenylphosphine (5.3 mg, 0.02 mmol) were added, and the reaction was heated at 100° C. overnight. Again, additional phenylboronic acid (123 mg, 1.01 mmol), palladium (II) acetate (1.5 mg, 0.0067 mmol), and triphenylphosphine (5.3 mg, 0.02 mmol) were added, plus 2 M aqueous sodium carbonate (0.4 mL, 0.8 mmol), and the reaction was heated at 100° C. overnight. After cooling to room temperature, the reaction mixture was diluted with chloroform (60 mL) and washed with water (2×10 mL) and brine (10 mL). The organic layer was dried over sodium sulfate, filtered, and concentrated under reduced pressure. The crude product was purified by chromatography on a HORIZON HPFC system (silica gel, gradient elution with 0-35% CMA in chloroform) followed by recrystallization from acetonitrile. The final product was isolated and dried under vacuum at 100° C. to yield N-[3-(4-amino-7-phenyl-2-propyl-1H-imidazo[4,5-c]quinolin-1-yl)propoxy]-2-methylpropanamide as a white powder, mp 169.0-171.0° C.

$^1$H NMR (300 MHz, DMSO-$d_6$) δ 10.97 (s, 1H), 8.17 (d, J=8.5 Hz, 1H), 7.86 (d, J= 2.0 Hz, 1H), 7.79-7.73 (m, 2H), 7.57-7.46 (m, 3H), 7.41-7.34 (m, 1H), 6.51 (s, 2H), 4.70 (dd, J=7.6, 6.6 Hz, 2H), 3.88 (dd, J=5.8, 5.5 Hz, 2H), 2.96 (t, J=7.6 Hz, 2H), 2.24 (heptet, J=6.9 Hz, 1H), 2.16-2.05 (m, 2H), 1.86 (sextet, J=7.6 Hz, 2H), 1.08-0.98 (m, 9H); HRMS (EI) calcd for $C_{26}H_{31}N_5O_2$+H, 446.2556. Found: 446.2550.

Example 139

2-(Ethoxymethyl)-1-{3-[(isopropylamino)oxy]propyl}-7-phenyl-1H-imidazo[4,5-c][1,5]naphthyridin-4-amine

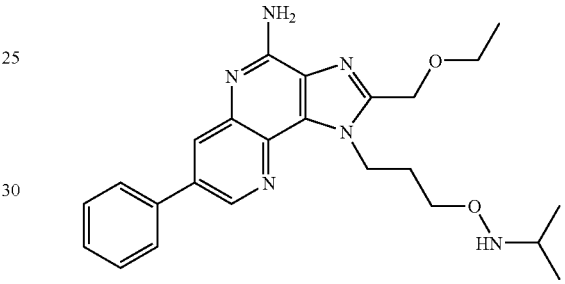

Part A

A mixture of triethyl orthoformate (10 mL, 60.1 mmol) and 2,2-dimethyl-1,3-dioxane-4,6-dione (40.9 g, 0.23 mol)(Meldrum's acid) was heated at 92° C. for 90 minutes and then cooled to 70° C. over one hour. 3-Amino-5-bromopyridine (40.9 g, 0.20 mol) was slowly added over 10 minutes with an ethanol rinse while maintaining the reaction temperature between 60 and 70° C. The reaction was then heated for an additional 20 minutes and allowed to cool to room temperature. The reaction mixture was filtered and washed with ethanol (150 mL) yielding a tan solid. The solid was dried under vacuum for 2 hours to yield 59.14 g of 5-{[(5-bromopyridin-3-yl)imino]methyl}-2,2-dimethyl-1,3-dioxane-4,6-dione as a light yellow crystalline solid, mp 200-202° C.

$^1$H NMR (300 MHz, CDCl$_3$) δ 11.26 (d, J=14.3 Hz, 1H), 8.80 (d, J=2.3 Hz, 1H), 8.62 (d, J=14.3 Hz, 1H), 8.56 (d, J=1.9 Hz, 1H), 8.44-8.40 (m, 1H), 1.68 (s, 6H).

Part B

5-{[(5-Bromopyridin-3-yl)imino]methyl}-2,2-dimethyl-1,3-dioxane-4,6-dione (59 g, 0.18 mol) was slowly added to DOWTHERM A heat transfer fluid (2000 mL) over a period of 5 minutes at 235-238° C. Following addition, the reaction was maintained for an additional 5 minutes and then allowed to cool to 40° C. A brown precipitate formed, which was filtered and washed with hexanes (150 mL). The brown solid was suspended in an ethanol/water mixture (90:10, 1500 mL), heated to a boil for 30 minutes, isolated by filtration, and washed with ethanol (200 mL) to yield 30.8 g of 7-bromo[1,5]naphthyridin-4-ol as a dark brown powder. $^1$H NMR (300 MHz, CDCl$_3$) δ 11.81 (br s, 1H), 8.69 (d, J=1.9 Hz, 1H), 8.21 (d, J=1.9 Hz, 1H), 7.95 (d, J=7.7 Hz, 1H), 6.22 (d, J=7.5 Hz, 1H).

Part C

A mixture of 7-bromo[1,5]naphthyridin-4-ol (33 g, 0.147 mol) and fuming nitric acid (350 mL) was heated at reflux (90° C. internal reaction vessel temperature) for 3 hours. The reaction mixture was cooled to 50° C., poured over 1 L of ice and adjusted to pH 2-3 with the addition of 50% aqueous NaOH. The resulting precipitate was filtered, washed with water, and dried over vacuum for 3 days to yield 25.1 g of 7-bromo-3-nitro[1,5]naphthyridin-4-ol as a yellow crystalline solid.

$^1$H NMR (300 MHz, CDCl$_3$) δ 13.06 (br s, 1H), 9.26 (s, 1H), 8.88 (d, J=2.0 Hz, 1H), 8.37 (d, J=2.0 Hz, 1H).

Part D

Phosphorous oxychloride (16.76 g, 10.19 mL, 109.3 mmol) was added slowly dropwise to a suspension of 7-bromo-3-nitro[1,5]naphthyridin-4-ol (21.09 g, 78.1 mmol) in DMF (250 mL) at ambient temperature and stirred for 3 hours. The reaction mixture was then added to ice water (400 mL) with stirring. A solid precipitate formed, which was isolated by vacuum filtration and washed with water. The material was dried under high vacuum at ambient temperature to yield 7-bromo-4-chloro-3-nitro[1,5]naphthyridine as a tan solid.

$^1$H NMR (300 MHz, CDCl$_3$) δ 9.5 (s, 1H), 9.36 (d, J=2.2 Hz, 1H), 9.02 (d, J=2.1 Hz, 1H).

Part E

To a solution of 7-bromo-4-chloro-3-nitro[1,5]naphthyridine (22.53 g, 78.10 g) in dichloromethane (260 mL) at room temperature was added triethylamine (14.2 mL, 102 mmol). The solution was cooled to 0° C., and 3-amino-1-propanol (6.57 mL, 85.9 mmol) was added. The solution was stirred for 20 minutes at room temperature and then was concentrated under reduced pressure to yield a yellow solid. Water (250 mL) was added to the solid and the mixture was sonicated for 10 minutes. The solid was isolated by filtration, washed with water, and dried at 70° C. under vacuum to afford 22.60 g of 3-[(7-bromo-3-nitro[1,5]naphthyridin-4-yl)amino]propan-1-ol as a yellow powder.

Part F

3-[(7-Bromo-3-nitro[1,5]naphthyridin-4-yl)amino]propan-1-ol (22.60 g, 69.08 mmol) was converted into 25.30 g of 3-[(7-bromo-3-nitro[1,5]naphthyridin-4-yl)amino]propyl acetate, which contained a trace amount of 4-dimethylaminopyridine, using the method described in Part B of Examples 105-128.

Part G

3-[(7-Bromo-3-nitro[1,5]naphthyridin-4-yl)amino]propyl acetate (25.3 g, 68.5 mmol) was converted into 3-[(3-amino-7-bromo[1,5]naphthyridin-4-yl)amino]propyl acetate using the method described in Part C of Examples 105-128.

Part H

The general procedures described in Parts D and E of Examples 105-128 were used to convert the material from Part G (approximately 68.5 mmol) into 22.2 g of 3-[7-bromo-2-(ethoxymethyl)-1H-imidazo[4,5-c][1,5]naphthyridin-1-yl]propan-1-ol using ethoxyacetyl chloride in lieu of butyryl chloride in Part D of Examples 105-128. Extra dichloromethane (250 mL) was used in the acylation reaction, and the reaction time was lengthened to overnight. In the cyclization reaction, the reaction was heated for 45 minutes instead of 7 hours.

Part I

Diisopropyl azodicarboxylate (6.47 mL, 32.9 mmol) was added dropwise over ten minutes to a stirred solution of 3-[7-bromo-2-(ethoxymethyl)-1H-imidazo[4,5-c][1,5]naphthyridin-1-yl]propan-1-ol (10.0 g, 27.4 mmol), triphenylphosphine (8.62 g, 32.9 mmol), and N-hydroxyphthalimide (5.36 g, 32.9 mmol) in DMF (110 mL) at 0° C. The reaction was allowed to warm to room temperature and was stirred overnight. The solvent was removed under reduced pressure to afford a solid that was slurried in ethyl acetate, isolated by filtration, washed with ethyl acetate, and dried under vacuum to yield 11.45 g of 2-{3-[7-bromo-2-(ethoxymethyl)-1H-imidazo[4,5-c][1,5]naphthyridin-1-yl]propoxy}-1H-isoindole-1,3(2H)-dione as a pink solid.

Part J mCPBA (11.06 g, 44.88 mmol) was added to a stirred solution of 2-{3-[7-bromo-2-(ethoxymethyl)-1H-imidazo[4,5-c][1,5]naphthyridin-1-yl]propoxy}-1H-isoindole-1,3(2H)-dione (11.40 g, 22.44 mmol) in chloroform (225 mL) at room temperature. After 1 hour, additional mCPBA (1.5 g) was added, and stirring was continued for another 30 minutes. The solution was cooled to 0° C., and concentrated ammonium hydroxide (45 mL) was added followed by p-toluenesulfonyl chloride (added in portions, 4.71 g, 24.7 mmol). After 1 hour, additional p-toluenesulfonyl chloride (1.0 g) was added, and stirring was continued at 0° C. After another 2 hours, more p-toluenesulfonyl chloride (0.4 g) was added, and then the reaction was stirred at room temperature for 1 hour. Acetone (225 mL) was added, and the reaction was stirred overnight at room temperature. The mixture was filtered and the filtrate was concentrated under reduced pressure. The residue was dissolved in chloroform (700 mL), and the solution was washed with saturated aqueous sodium bicarbonate (2×100 mL) and brine (70 mL), dried over sodium sulfate, filtered, and concentrated under reduced pressure. The crude material, which contained about 50% of the unreacted N-oxide intermediate, was dissolved in chloroform (220 mL). The solution was cooled to 0° C., and concentrated ammonium hydroxide (20 mL) was added, followed by portionwise addition of p-toluenesulfonyl chloride (4 g). The reaction was allowed to warm to room temperature and was stirred overnight. The mixture was filtered again, and the filtrate was treated to the work-up described above. The crude product was purified by chromatography on a HORIZON HPFC system (silica gel, gradient elution with 0-25% CMA in chloroform), recrystallized from ethyl acetate/hexanes, and dried under vacuum to provide 2.8 g of acetone O-{3-[4-amino-7-bromo-2-(ethoxymethyl)-1H-imidazo[4,5-c][1,5]naphmyridin-1-yl]propyl}oxime as a beige powder, mp 128.0-130.0° C.

$^1$H NMR (300 MHz, DMSO-d$_6$) δ 8.55 (d, J=2.2 Hz, 1H), 8.11 (d, J=2.2 Hz, 1H), 7.13 (s, 2H), 4.84 (t, J=7.1 Hz, 2H), 4.77 (s, 2H), 4.03 (t, J=6.0 Hz, 2H), 3.56 (q, J=7.0 Hz, 2H), 2.28-2.15 (m, 2H), 1.75 (s, 3H), 1.73 (s, 3H), 1.16 (t, J=7.0 Hz, 3H);

HRMS (EI) Calcd. for C$_{18}$H$_{23}$BrN$_6$O$_2$ (M+H)$^+$: 435.1144. Found: 435.1142.

Part K

In a pressure vessel under a nitrogen atmosphere, acetone O-{3-[4-amino-7-bromo-2-(ethoxymethyl)-1H-imidazo[4,5-c][1,5]naphthyridin-1-yl]propyl}oxime (2.50 g, 5.74 mmol), phenylboronic acid (1.05 g, 8.61 mmol), palladium (II) acetate (13 mg, 0.057 mmol), triphenylphosphine (45 mg, 0.17 mmol), and 2 M aqueous sodium carbonate (3.45 mL, 6.89 mmol) were combined in 5:1 n-propanol:water (12 mL). The solution was placed under vacuum and back-filled with nitrogen three times. The pressure vessel was sealed and heated at 100° C. for 2 days, then was allowed to cool to ambient temperature. Chloroform (200 mL) was added and the mixture was washed with water (40 mL) and brine (40 mL), dried over sodium sulfate, filtered, and concentrated under reduced pressure. The product was purified by chromatography on a HORIZON HPFC system (silica gel, gradient elution with 0-25% CMA in chloroform) to yield 2.4 g of acetone O-{3-[4-amino-2-(ethoxymethyl)-7-phenyl-1H-imidazo[4,5-c][1,5]naphthyridin-1-yl]propyl}oxime as a yellow powder, mp 134.0-136.0° C.

$^1$H NMR (300 MHz, DMSO-$d_6$) δ 8.85 (d, J=2.2 Hz, 1H), 8.13 (d, J=2.2 Hz, 1H), 7.92-7.80 (m, 2H), 7.57-7.39 (m, 3H), 6.94 (s, 2H), 4.91 (dd, J=7.6, 6.6 Hz, 2H), 4.79 (s, 2H), 4.06 (t, J=6.0 Hz, 2H), 3.57 (q, J=7.0 Hz, 2H), 2.35-2.21 (m, 2H), 1.77 (s, 3H), 1.76 (s, 3H), 1.18 (t, J=7.0 Hz, 3H);

HRMS (EI) Calcd. for $C_{24}H_{28}N_6O_2$ (M+H)$^+$: 433.2352. Found: 433.2342.

Part L

A slurry of acetone O-{3-[4-amino-2-(ethoxymethyl)-7-phenyl-1H-imidazo[4,5-c][1,5]naphthyridin-1-yl]propyl}oxime (1.00 g, 2.31 mmol), 1 M sodium cyanoborohydride in tetrahydrofuran (4.62 mL, 4.62 mmol), methanol (12 mL), and acetic acid (4.5 mL) was stirred overnight at ambient temperature. The resulting solution was concentrated under reduced pressure and the residue was dissolved in chloroform (200 mL). The solution was washed with saturated aqueous sodium bicarbonate (2×40 mL) and brine (30 mL), dried over sodium sulfate, filtered, and concentrated under reduced pressure to yield 1.0 g of 2-(ethoxymethyl)-1-{3-[(isopropylamino)oxy]propyl}-7-phenyl-1H-imidazo[4,5-c][1,5]naphthyridin-4-amine as a yellow powder, mp 142.0-144.0° C.

$^1$H NMR (300 MHz, DMSO-$d_6$) δ 8.86 (d, J=2.2 Hz, 1H), 8.14 (d, J=2.2 Hz, 1H), 7.94-7.80 (m, 2H), 7.63-7.40 (m, 3H), 6.98 (s, 2H), 6.22 (br s, 1H), 4.87 (dd, J=7.6, 6.6 Hz, 2H), 4.82 (s, 2H), 3.70 (t, J=6.0 Hz, 2H), 3.60 (q, J=7.0 Hz, 2H), 3.10-2.95 (m, 1H), 2.25-2.10 (m, 2H), 1.19 (t, J=7.0 Hz, 3H), 0.97 (s, 3H), 0.95 (s, 3H).

HRMS (EI) Calcd. for $C_{24}H_{30}N_6O_2$ (M+H)$^+$: 435.2508. Found 435.2509.

Example 140

N-[4-(4-amino-6,7,8,9-tetrahydro-1H-imidazo[4,5-c]quinolin-1-yl)butoxy]acetamide

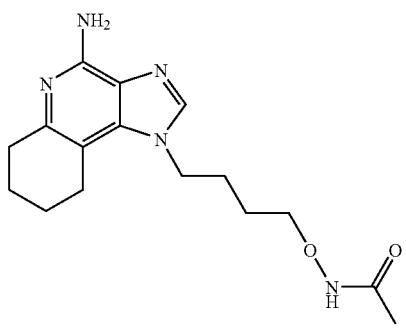

Part A

Platinum (IV) oxide (3.5 g) was added to a solution of 4-(4-amino-1H-imidazo[4,5-c]quinolin-1-yl)butan-1-ol (prepared as described in Example 9 of U.S. Pat. No. 6,664,264, 4.00 g, 15.6 mmol) in trifluoroacetic acid (200 mL), and the mixture was shaken under hydrogen pressure for 2 days on a Parr apparatus. The reaction mixture was concentrated under reduced pressure, carefully diluted with methanol, and filtered through a layer of CELITE filter agent. The filtrate was concentrated under reduced pressure. The resulting residue was diluted with a solution of 4 M hydrogen chloride in 1,4-dioxane (100 mL) and stirred at ambient temperature for 1 hour, and then 4 M aqueous sodium hydroxide was added to adjust to pH 13. The mixture was transferred to a separatory funnel, and dichloromethane was added. The mixture was shaken and allowed to stand overnight at ambient temperature. The organic layer was separated, and the aqueous layer was extracted with dichloromethane. The organic layers were combined, dried over magnesium sulfate, filtered, and concentrated under reduced pressure to provide 1.0 g of 4-(4-amino-6,7,8,9-tetrahydro-1H-imidazo[4,5-c]quinolin-1-yl)butan-1-ol as a white solid.

Part B

A cloudy solution of 4-(4-amino-6,7,8,9-tetrahydro-1H-imidazo[4,5-c]quinolin-1-yl)butan-1-ol (1.0 g, 3.8 mmol), triphenylphosphine (1.49 g, 5.7 mmol) and N-hydroxyphthalimide (0.93 g, 5.7 mmol) in tetrahydrofuran (50 mL) was cooled to approximately 0° C.; then diisopropyl azodicarboxylate (1.33 mL, 6.8 mmol) was added dropwise. The reaction was allowed to warm to ambient temperature and was stirred for 5 hours. The solvent was removed under reduced pressure and the resulting solid was purified by chromatography on silica gel (gradient elution with 0-10% methanol in dichloromethane with a small amount of concentrated ammonium hydroxide added) to provide 600 mg of 2-[4-(4-amino-6,7,8,9-tetrahydro-1H-imidazo[4,5-c]quinolin-1-yl)butoxy]-1H-isoindole-1,3(2H) dione as a yellow solid.

Part C

Anhydrous hydrazine (94 mg, 2.96 mmol) was added to 2-[4-(4-amino-6,7,8,9-tetrahydro-1H-imidazo[4,5-c]quinolin-1-yl)butoxy]-1H-isoindole-1,3(2H)-dione (600 mg, 1.48 mmol) in ethanol (25 mL) at ambient temperature. The reaction was stirred overnight, and additional hydrazine (2 equivalents) was added. After stirring for 2 hours at ambient temperature, the reaction was concentrated under reduced pressure. The residue was diluted with dichloromethane and concentrated under reduced pressure three times to remove the hydrazine and then dried under vacuum to provide 550 mg of impure 1-[4-(aminooxy)butyl]-6,7,8,9-tetrahydro-1H-imidazo[4,5-c]quinolin-4-amine as an orange solid.

Part D

To a solution of the 1-[4-(aminooxy)butyl]-6,7,8,9-tetrahydro-1H-imidazo[4,5-c]quinolin-4-amine from Part C (200 mg, 0.73 mmol) and triethylamine (512 µL, 3.56 mmol) in pyridine (25 mL) was added acetyl chloride (57 µL, 0.80 mmol). The solution was stirred for 30 minutes at ambient temperature, and additional acetyl chloride (1 equivalent) was added. After 1 hour, water was added and the mixture was extracted with dichloromethane (2×). The aqueous layer was concentrated under reduced pressure to yield a white solid that was purified by chromatography (silica gel, gradient elution with 0-10% methanol in dichloromethane with a small amount of concentrated ammonium hydroxide added) to provide 30 mg of N-[4-(4-amino-6,7,8,9-tetrahydro-1H-imidazo[4,5-c]quinolin-1-yl)butoxy]acetamide as a white solid.

$^1$H NMR (300 MHz, DMSO-$d_6$) δ 10.85 (br s, 1H), 7.99 (s, 1H), 6.21 (br s, 2H), 4.33 (t, J=7.2 Hz, 2H), 3.77 (t, J=6.3 Hz, 2H), 3.18 (s, 3H), 2.95 (m, 2H), 2.69 (m, 2H), 1.85-1.71 (m, 6H), 1.55 (m, 2H);

MS (ESI) m/z 318 (M+H)+
HRMS (EI) Calcd. for $C_{16}H_{23}N_5O_2$ (M+H)+: 318.1930. Found: 318.1925.

Example 141

N-{4-[4-Amino-2-(ethoxymethyl)-6,7,8,9-tetrahydro-1H-imidazo[4,5-c]quinolin-1-yl]butoxy}cyclopropanecarboxamide

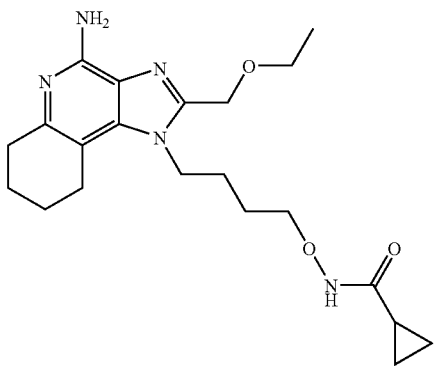

Part A

The methods described in Parts B and C of Example 1 can be used to treat 4-[2-(ethoxymethyl)-1H-imidazo[4,5-c]quinolin-1-yl)butan-1-ol with mCPBA and ammonium hydroxide to provide 4-[4-amino-2-(ethoxymethyl)-1H-imidazo[4,5-c]quinolin-1-yl)butan-1-ol.

Part B

The method described in Part A of Example 140 can be used to reduce 4-[4-amino-2-(ethoxymethyl)-1H-imidazo[4,5-c]quinolin-1-yl)butan-1-ol to 4-[4-amino-2-(ethoxymethyl)-6,7,8,9-tetrahydro-1H-imidazo[4,5-c]quinolin-1-yl)butan-1-ol.

Part C

The method described in Part A of Example 1 can be used to convert 4-[4-amino-2-(ethoxymethyl)-6,7,8,9-tetrahydro-1-imidazo[4,5-c]quinolin-1-yl)butan-1-ol to 2-{4-[4-amino-2-(ethoxymethyl)-6,7,8,9-tetrahydro-1H-imidazo[4,5-c]quinolin-1-yl)butoxy]-1H-isoindole-1,3(2H)-dione.

Part D

The method described in Part C of Example 140 can be used to treat 2-{4-[4-amino-2-(ethoxymethyl)-6,7,8,9-tetrahydro-1H-imidazo[4,5-c]quinolin-1-yl)butoxy]-1H-isoindole-1,3(2H)-dione with anhydrous hydrazine to provide 1-[4-(aminooxy)butyl]-2-(ethoxymethyl)-6,7,8,9-tetrahydro-1H-imidazo[4,5-c]quinolin-4-amine.

Part E

The method described in Example 3 can be used to treat 1-[4-(aminooxy)butyl]-2-(ethoxymethyl)-6,7,8,9-tetrahydro-1H-imidazo[4,5-c]quinolin-4-amine with cyclopropanecarbonyl chloride to provide N-{4-[4-amino-2-(ethoxymethyl)-6,7,8,9-tetrahydro-1H-imidazo[4,5-c]quinolin-1-yl]butoxy}cyclopropanecarboxamide.

Exemplary Compounds

Certain exemplary compounds, including some of those described above in the Examples, have the following Formulas (IIIa and VIIIa) and the following R', $R_1$, X, $R_2$ and $R_3$ substituents, wherein each line of the table is matched with Formula IIIa or VIIIa to represent a specific embodiment of the invention.

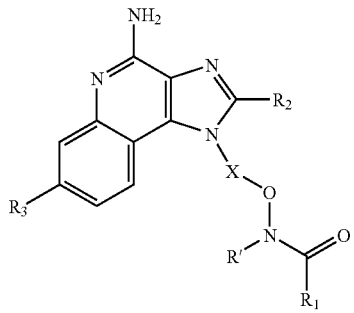

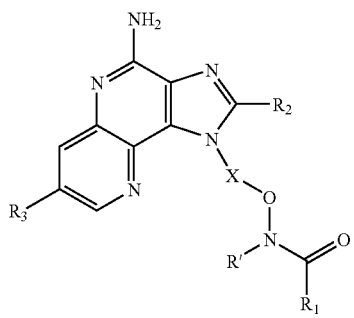

| $R_1$ | R' | X | $R_2$ | $R_3$ |
|---|---|---|---|---|
| methyl | hydrogen | —(CH$_2$)$_3$— | hydrogen | 3-pyridyl |
| methyl | hydrogen | —(CH$_2$)$_3$— | hydrogen | phenyl |
| methyl | hydrogen | —(CH$_2$)$_3$— | ethyl | 3-pyridyl |
| methyl | hydrogen | —(CH$_2$)$_3$— | ethyl | phenyl |
| methyl | hydrogen | —(CH$_2$)$_3$— | propyl | 3-pyridyl |
| methyl | hydrogen | —(CH$_2$)$_3$— | propyl | phenyl |
| methyl | hydrogen | —(CH$_2$)$_3$— | ethoxymethyl | 3-pyridyl |
| methyl | hydrogen | —(CH$_2$)$_3$— | ethoxymethyl | phenyl |
| methyl | hydrogen | —(CH$_2$)$_3$— | butyl | 3-pyridyl |
| methyl | hydrogen | —(CH$_2$)$_3$— | butyl | phenyl |
| methyl | hydrogen | —(CH$_2$)$_4$— | hydrogen | 3-pyridyl |
| methyl | hydrogen | —(CH$_2$)$_4$— | hydrogen | phenyl |
| methyl | hydrogen | —(CH$_2$)$_4$— | ethyl | 3-pyridyl |
| methyl | hydrogen | —(CH$_2$)$_4$— | ethyl | phenyl |
| methyl | hydrogen | —(CH$_2$)$_4$— | propyl | 3-pyridyl |
| methyl | hydrogen | —(CH$_2$)$_4$— | propyl | phenyl |
| methyl | hydrogen | —(CH$_2$)$_4$— | ethoxymethyl | 3-pyridyl |
| methyl | hydrogen | —(CH$_2$)$_4$— | ethoxymethyl | phenyl |
| methyl | hydrogen | —(CH$_2$)$_4$— | butyl | 3-pyridyl |
| methyl | hydrogen | —(CH$_2$)$_4$— | butyl | phenyl |
| methyl | hydrogen | —CH$_2$C(CH$_3$)$_2$CH$_2$— | hydrogen | 3-pyridyl |
| methyl | hydrogen | —CH$_2$C(CH$_3$)$_2$CH$_2$— | hydrogen | phenyl |
| methyl | hydrogen | —CH$_2$C(CH$_3$)$_2$CH$_2$— | ethyl | 3-pyridyl |
| methyl | hydrogen | —CH$_2$C(CH$_3$)$_2$CH$_2$— | ethyl | phenyl |
| methyl | hydrogen | —CH$_2$C(CH$_3$)$_2$CH$_2$— | propyl | 3-pyridyl |
| methyl | hydrogen | —CH$_2$C(CH$_3$)$_2$CH$_2$— | propyl | phenyl |
| methyl | hydrogen | —CH$_2$C(CH$_3$)$_2$CH$_2$— | ethoxymethyl | 3-pyridyl |
| methyl | hydrogen | —CH$_2$C(CH$_3$)$_2$CH$_2$— | ethoxymethyl | phenyl |
| methyl | hydrogen | —CH$_2$C(CH$_3$)$_2$CH$_2$— | butyl | 3-pyridyl |
| methyl | hydrogen | —CH$_2$C(CH$_3$)$_2$CH$_2$— | butyl | phenyl |
| methyl | hydrogen | —(CH$_2$)$_2$O(CH$_2$)$_2$— | hydrogen | 3-pyridyl |
| methyl | hydrogen | —(CH$_2$)$_2$O(CH$_2$)$_2$— | hydrogen | phenyl |
| methyl | hydrogen | —(CH$_2$)$_2$O(CH$_2$)$_2$— | ethyl | 3-pyridyl |
| methyl | hydrogen | —(CH$_2$)$_2$O(CH$_2$)$_2$— | ethyl | phenyl |
| methyl | hydrogen | —(CH$_2$)$_2$O(CH$_2$)$_2$— | propyl | 3-pyridyl |
| methyl | hydrogen | —(CH$_2$)$_2$O(CH$_2$)$_2$— | propyl | phenyl |

| | | | | |
|---|---|---|---|---|
| methyl | hydrogen | —(CH$_2$)$_2$O(CH$_2$)$_2$— | ethoxymethyl | 3-pyridyl |
| methyl | hydrogen | —(CH$_2$)$_2$O(CH$_2$)$_2$— | ethoxymethyl | phenyl |
| methyl | hydrogen | —(CH$_2$)$_2$O(CH$_2$)$_2$— | butyl | 3-pyridyl |
| methyl | hydrogen | —(CH$_2$)$_2$O(CH$_2$)$_2$— | butyl | phenyl |
| cyclopropyl | hydrogen | —(CH$_2$)$_3$— | hydrogen | 3-pyridyl |
| cyclopropyl | hydrogen | —(CH$_2$)$_3$— | hydrogen | phenyl |
| cyclopropyl | hydrogen | —(CH$_2$)$_3$— | ethyl | 3-pyridyl |
| cyclopropyl | hydrogen | —(CH$_2$)$_3$— | ethyl | phenyl |
| cyclopropyl | hydrogen | —(CH$_2$)$_3$— | propyl | 3-pyridyl |
| cyclopropyl | hydrogen | —(CH$_2$)$_3$— | propyl | phenyl |
| cyclopropyl | hydrogen | —(CH$_2$)$_3$— | ethoxymethyl | 3-pyridyl |
| cyclopropyl | hydrogen | —(CH$_2$)$_3$— | ethoxymethyl | phenyl |
| cyclopropyl | hydrogen | —(CH$_2$)$_3$— | butyl | 3-pyridyl |
| cyclopropyl | hydrogen | —(CH$_2$)$_3$— | butyl | phenyl |
| cyclopropyl | hydrogen | —(CH$_2$)$_4$— | hydrogen | 3-pyridyl |
| cyclopropyl | hydrogen | —(CH$_2$)$_4$— | hydrogen | phenyl |
| cyclopropyl | hydrogen | —(CH$_2$)$_4$— | ethyl | 3-pyridyl |
| cyclopropyl | hydrogen | —(CH$_2$)$_4$— | ethyl | phenyl |
| cyclopropyl | hydrogen | —(CH$_2$)$_4$— | propyl | 3-pyridyl |
| cyclopropyl | hydrogen | —(CH$_2$)$_4$— | propyl | phenyl |
| cyclopropyl | hydrogen | —(CH$_2$)$_4$— | ethoxymethyl | 3-pyridyl |
| cyclopropyl | hydrogen | —(CH$_2$)$_4$— | ethoxymethyl | phenyl |
| cyclopropyl | hydrogen | —(CH$_2$)$_4$— | butyl | 3-pyridyl |
| cyclopropyl | hydrogen | —(CH$_2$)$_4$— | butyl | phenyl |
| cyclopropyl | hydrogen | —CH$_2$C(CH$_3$)$_2$CH$_2$— | hydrogen | 3-pyridyl |
| cyclopropyl | hydrogen | —CH$_2$C(CH$_3$)$_2$CH$_2$— | hydrogen | phenyl |
| cyclopropyl | hydrogen | —CH$_2$C(CH$_3$)$_2$CH$_2$— | ethyl | 3-pyridyl |
| cyclopropyl | hydrogen | —CH$_2$C(CH$_3$)$_2$CH$_2$— | ethyl | phenyl |
| cyclopropyl | hydrogen | —CH$_2$C(CH$_3$)$_2$CH$_2$— | propyl | 3-pyridyl |
| cyclopropyl | hydrogen | —CH$_2$C(CH$_3$)$_2$CH$_2$— | propyl | phenyl |
| cyclopropyl | hydrogen | —CH$_2$C(CH$_3$)$_2$CH$_2$— | ethoxymethyl | 3-pyridyl |
| cyclopropyl | hydrogen | —CH$_2$C(CH$_3$)$_2$CH$_2$— | ethoxymethyl | phenyl |
| cyclopropyl | hydrogen | —CH$_2$C(CH$_3$)$_2$CH$_2$— | butyl | 3-pyridyl |
| cyclopropyl | hydrogen | —CH$_2$C(CH$_3$)$_2$CH$_2$— | butyl | phenyl |
| cyclopropyl | hydrogen | —(CH$_2$)$_2$O(CH$_2$)$_2$— | hydrogen | 3-pyridyl |
| cyclopropyl | hydrogen | —(CH$_2$)$_2$O(CH$_2$)$_2$— | hydrogen | phenyl |
| cyclopropyl | hydrogen | —(CH$_2$)$_2$O(CH$_2$)$_2$— | ethyl | 3-pyridyl |
| cyclopropyl | hydrogen | —(CH$_2$)$_2$O(CH$_2$)$_2$— | ethyl | phenyl |
| cyclopropyl | hydrogen | —(CH$_2$)$_2$O(CH$_2$)$_2$— | propyl | 3-pyridyl |
| cyclopropyl | hydrogen | —(CH$_2$)$_2$O(CH$_2$)$_2$— | propyl | phenyl |
| cyclopropyl | hydrogen | —(CH$_2$)$_2$O(CH$_2$)$_2$— | ethoxymethyl | 3-pyridyl |
| cyclopropyl | hydrogen | —(CH$_2$)$_2$O(CH$_2$)$_2$— | ethoxymethyl | phenyl |
| cyclopropyl | hydrogen | —(CH$_2$)$_2$O(CH$_2$)$_2$— | butyl | 3-pyridyl |
| cyclopropyl | hydrogen | —(CH$_2$)$_2$O(CH$_2$)$_2$— | butyl | phenyl |
| isopropyl | hydrogen | —(CH$_2$)$_3$— | hydrogen | 3-pyridyl |
| isopropyl | hydrogen | —(CH$_2$)$_3$— | hydrogen | phenyl |
| isopropyl | hydrogen | —(CH$_2$)$_3$— | ethyl | 3-pyridyl |
| isopropyl | hydrogen | —(CH$_2$)$_3$— | ethyl | phenyl |
| isopropyl | hydrogen | —(CH$_2$)$_3$— | propyl | 3-pyridyl |
| isopropyl | hydrogen | —(CH$_2$)$_3$— | propyl | phenyl |
| isopropyl | hydrogen | —(CH$_2$)$_3$— | ethoxymethyl | 3-pyridyl |
| isopropyl | hydrogen | —(CH$_2$)$_3$— | ethoxymethyl | phenyl |
| isopropyl | hydrogen | —(CH$_2$)$_3$— | butyl | 3-pyridyl |
| isopropyl | hydrogen | —(CH$_2$)$_3$— | butyl | phenyl |
| isopropyl | hydrogen | —(CH$_2$)$_4$— | hydrogen | 3-pyridyl |
| isopropyl | hydrogen | —(CH$_2$)$_4$— | hydrogen | phenyl |
| isopropyl | hydrogen | —(CH$_2$)$_4$— | ethyl | 3-pyridyl |
| isopropyl | hydrogen | —(CH$_2$)$_4$— | ethyl | phenyl |
| isopropyl | hydrogen | —(CH$_2$)$_4$— | propyl | 3-pyridyl |
| isopropyl | hydrogen | —(CH$_2$)$_4$— | propyl | phenyl |
| isopropyl | hydrogen | —(CH$_2$)$_4$— | ethoxymethyl | 3-pyridyl |
| isopropyl | hydrogen | —(CH$_2$)$_4$— | ethoxymethyl | phenyl |
| isopropyl | hydrogen | —(CH$_2$)$_4$— | butyl | 3-pyridyl |
| isopropyl | hydrogen | —(CH$_2$)$_4$— | butyl | phenyl |
| isopropyl | hydrogen | —CH$_2$C(CH$_3$)$_2$CH$_2$— | hydrogen | 3-pyridyl |
| isopropyl | hydrogen | —CH$_2$C(CH$_3$)$_2$CH$_2$— | hydrogen | phenyl |
| isopropyl | hydrogen | —CH$_2$C(CH$_3$)$_2$CH$_2$— | ethyl | 3-pyridyl |
| isopropyl | hydrogen | —CH$_2$C(CH$_3$)$_2$CH$_2$— | ethyl | phenyl |
| isopropyl | hydrogen | —CH$_2$C(CH$_3$)$_2$CH$_2$— | propyl | 3-pyridyl |
| isopropyl | hydrogen | —CH$_2$C(CH$_3$)$_2$CH$_2$— | propyl | phenyl |
| isopropyl | hydrogen | —CH$_2$C(CH$_3$)$_2$CH$_2$— | ethoxymethyl | 3-pyridyl |
| isopropyl | hydrogen | —CH$_2$C(CH$_3$)$_2$CH$_2$— | ethoxymethyl | phenyl |
| isopropyl | hydrogen | —CH$_2$C(CH$_3$)$_2$CH$_2$— | butyl | 3-pyridyl |
| isopropyl | hydrogen | —CH$_2$C(CH$_3$)$_2$CH$_2$— | butyl | phenyl |
| isopropyl | hydrogen | —(CH$_2$)$_2$O(CH$_2$)$_2$— | hydrogen | 3-pyridyl |
| isopropyl | hydrogen | —(CH$_2$)$_2$O(CH$_2$)$_2$— | hydrogen | phenyl |
| isopropyl | hydrogen | —(CH$_2$)$_2$O(CH$_2$)$_2$— | ethyl | 3-pyridyl |
| isopropyl | hydrogen | —(CH$_2$)$_2$O(CH$_2$)$_2$— | ethyl | phenyl |
| isopropyl | hydrogen | —(CH$_2$)$_2$O(CH$_2$)$_2$— | propyl | 3-pyridyl |
| isopropyl | hydrogen | —(CH$_2$)$_2$O(CH$_2$)$_2$— | propyl | phenyl |
| isopropyl | hydrogen | —(CH$_2$)$_2$O(CH$_2$)$_2$— | ethoxymethyl | 3-pyridyl |
| isopropyl | hydrogen | —(CH$_2$)$_2$O(CH$_2$)$_2$— | ethoxymethyl | phenyl |
| isopropyl | hydrogen | —(CH$_2$)$_2$O(CH$_2$)$_2$— | butyl | 3-pyridyl |
| isopropyl | hydrogen | —(CH$_2$)$_2$O(CH$_2$)$_2$— | butyl | phenyl |
| methyl | methyl | —(CH$_2$)$_3$— | hydrogen | 3-pyridyl |
| methyl | methyl | —(CH$_2$)$_3$— | hydrogen | phenyl |
| methyl | methyl | —(CH$_2$)$_3$— | ethyl | 3-pyridyl |
| methyl | methyl | —(CH$_2$)$_3$— | ethyl | phenyl |
| methyl | methyl | —(CH$_2$)$_3$— | propyl | 3-pyridyl |
| methyl | methyl | —(CH$_2$)$_3$— | propyl | phenyl |
| methyl | methyl | —(CH$_2$)$_3$— | ethoxymethyl | 3-pyridyl |
| methyl | methyl | —(CH$_2$)$_3$— | ethoxymethyl | phenyl |
| methyl | methyl | —(CH$_2$)$_3$— | butyl | 3-pyridyl |
| methyl | methyl | —(CH$_2$)$_3$— | butyl | phenyl |
| methyl | methyl | —(CH$_2$)$_4$— | hydrogen | 3-pyridyl |
| methyl | methyl | —(CH$_2$)$_4$— | hydrogen | phenyl |
| methyl | methyl | —(CH$_2$)$_4$— | ethyl | 3-pyridyl |
| methyl | methyl | —(CH$_2$)$_4$— | ethyl | phenyl |
| methyl | methyl | —(CH$_2$)$_4$— | propyl | 3-pyridyl |
| methyl | methyl | —(CH$_2$)$_4$— | propyl | phenyl |
| methyl | methyl | —(CH$_2$)$_4$— | ethoxymethyl | 3-pyridyl |
| methyl | methyl | —(CH$_2$)$_4$— | ethoxymethyl | phenyl |
| methyl | methyl | —(CH$_2$)$_4$— | butyl | 3-pyridyl |
| methyl | methyl | —(CH$_2$)$_4$— | butyl | phenyl |
| methyl | methyl | —CH$_2$C(CH$_3$)$_2$CH$_2$— | hydrogen | 3-pyridyl |
| methyl | methyl | —CH$_2$C(CH$_3$)$_2$CH$_2$— | hydrogen | phenyl |
| methyl | methyl | —CH$_2$C(CH$_3$)$_2$CH$_2$— | ethyl | 3-pyridyl |
| methyl | methyl | —CH$_2$C(CH$_3$)$_2$CH$_2$— | ethyl | phenyl |
| methyl | methyl | —CH$_2$C(CH$_3$)$_2$CH$_2$— | propyl | 3-pyridyl |
| methyl | methyl | —CH$_2$C(CH$_3$)$_2$CH$_2$— | propyl | phenyl |
| methyl | methyl | —CH$_2$C(CH$_3$)$_2$CH$_2$— | ethoxymethyl | 3-pyridyl |
| methyl | methyl | —CH$_2$C(CH$_3$)$_2$CH$_2$— | ethoxymethyl | phenyl |
| methyl | methyl | —CH$_2$C(CH$_3$)$_2$CH$_2$— | butyl | 3-pyridyl |
| methyl | methyl | —CH$_2$C(CH$_3$)$_2$CH$_2$— | butyl | phenyl |
| methyl | methyl | —(CH$_2$)$_2$O(CH$_2$)$_2$— | hydrogen | 3-pyridyl |
| methyl | methyl | —(CH$_2$)$_2$O(CH$_2$)$_2$— | hydrogen | phenyl |
| methyl | methyl | —(CH$_2$)$_2$O(CH$_2$)$_2$— | ethyl | 3-pyridyl |
| methyl | methyl | —(CH$_2$)$_2$O(CH$_2$)$_2$— | ethyl | phenyl |
| methyl | methyl | —(CH$_2$)$_2$O(CH$_2$)$_2$— | propyl | 3-pyridyl |
| methyl | methyl | —(CH$_2$)$_2$O(CH$_2$)$_2$— | propyl | phenyl |
| methyl | methyl | —(CH$_2$)$_2$O(CH$_2$)$_2$— | ethoxymethyl | 3-pyridyl |
| methyl | methyl | —(CH$_2$)$_2$O(CH$_2$)$_2$— | ethoxymethyl | phenyl |
| methyl | methyl | —(CH$_2$)$_2$O(CH$_2$)$_2$— | butyl | 3-pyridyl |
| methyl | methyl | —(CH$_2$)$_2$O(CH$_2$)$_2$— | butyl | phenyl |
| cyclopropyl | methyl | —(CH$_2$)$_3$— | hydrogen | 3-pyridyl |
| cyclopropyl | methyl | —(CH$_2$)$_3$— | hydrogen | phenyl |
| cyclopropyl | methyl | —(CH$_2$)$_3$— | ethyl | 3-pyridyl |
| cyclopropyl | methyl | —(CH$_2$)$_3$— | ethyl | phenyl |
| cyclopropyl | methyl | —(CH$_2$)$_3$— | propyl | 3-pyridyl |
| cyclopropyl | methyl | —(CH$_2$)$_3$— | propyl | phenyl |
| cyclopropyl | methyl | —(CH$_2$)$_3$— | ethoxymethyl | 3-pyridyl |

-continued

| | | | | |
|---|---|---|---|---|
| cyclopropyl | methyl | —(CH₂)₃— | ethoxymethyl | phenyl |
| cyclopropyl | methyl | —(CH₂)₃— | butyl | 3-pyridyl |
| cyclopropyl | methyl | —(CH₂)₃— | butyl | phenyl |
| cyclopropyl | methyl | —(CH₂)₄— | hydrogen | 3-pyridyl |
| cyclopropyl | methyl | —(CH₂)₄— | hydrogen | phenyl |
| cyclopropyl | methyl | —(CH₂)₄— | ethyl | 3-pyridyl |
| cyclopropyl | methyl | —(CH₂)₄— | ethyl | phenyl |
| cyclopropyl | methyl | —(CH₂)₄— | propyl | 3-pyridyl |
| cyclopropyl | methyl | —(CH₂)₄— | propyl | phenyl |
| cyclopropyl | methyl | —(CH₂)₄— | ethoxymethyl | 3-pyridyl |
| cyclopropyl | methyl | —(CH₂)₄— | ethoxymethyl | phenyl |
| cyclopropyl | methyl | —(CH₂)₄— | butyl | 3-pyridyl |
| cyclopropyl | methyl | —(CH₂)₄— | butyl | phenyl |
| cyclopropyl | methyl | —CH₂C(CH₃)₂CH₂— | hydrogen | 3-pyridyl |
| cyclopropyl | methyl | —CH₂C(CH₃)₂CH₂— | hydrogen | phenyl |
| cyclopropyl | methyl | —CH₂C(CH₃)₂CH₂— | ethyl | 3-pyridyl |
| cyclopropyl | methyl | —CH₂C(CH₃)₂CH₂— | ethyl | phenyl |
| cyclopropyl | methyl | —CH₂C(CH₃)₂CH₂— | propyl | 3-pyridyl |
| cyclopropyl | methyl | —CH₂C(CH₃)₂CH₂— | propyl | phenyl |
| cyclopropyl | methyl | —CH₂C(CH₃)₂CH₂— | ethoxymethyl | 3-pyridyl |
| cyclopropyl | methyl | —CH₂C(CH₃)₂CH₂— | ethoxymethyl | phenyl |
| cyclopropyl | methyl | —CH₂C(CH₃)₂CH₂— | butyl | 3-pyridyl |
| cyclopropyl | methyl | —CH₂C(CH₃)₂CH₂— | butyl | phenyl |
| cyclopropyl | methyl | —(CH₂)₂O(CH₂)₂— | hydrogen | 3-pyridyl |
| cyclopropyl | methyl | —(CH₂)₂O(CH₂)₂— | hydrogen | phenyl |
| cyclopropyl | methyl | —(CH₂)₂O(CH₂)₂— | ethyl | 3-pyridyl |
| cyclopropyl | methyl | —(CH₂)₂O(CH₂)₂— | ethyl | phenyl |
| cyclopropyl | methyl | —(CH₂)₂O(CH₂)₂— | propyl | 3-pyridyl |
| cyclopropyl | methyl | —(CH₂)₂O(CH₂)₂— | propyl | phenyl |
| cyclopropyl | methyl | —(CH₂)₂O(CH₂)₂— | ethoxymethyl | 3-pyridyl |
| cyclopropyl | methyl | —(CH₂)₂O(CH₂)₂— | ethoxymethyl | phenyl |
| cyclopropyl | methyl | —(CH₂)₂O(CH₂)₂— | butyl | 3-pyridyl |
| cyclopropyl | methyl | —(CH₂)₂O(CH₂)₂— | butyl | phenyl |
| isopropyl | methyl | —(CH₂)₃— | hydrogen | 3-pyridyl |
| isopropyl | methyl | —(CH₂)₃— | hydrogen | phenyl |
| isopropyl | methyl | —(CH₂)₃— | ethyl | 3-pyridyl |
| isopropyl | methyl | —(CH₂)₃— | ethyl | phenyl |
| isopropyl | methyl | —(CH₂)₃— | propyl | 3-pyridyl |
| isopropyl | methyl | —(CH₂)₃— | propyl | phenyl |
| isopropyl | methyl | —(CH₂)₃— | ethoxymethyl | 3-pyridyl |
| isopropyl | methyl | —(CH₂)₃— | ethoxymethyl | phenyl |
| isopropyl | methyl | —(CH₂)₃— | butyl | 3-pyridyl |
| isopropyl | methyl | —(CH₂)₃— | butyl | phenyl |
| isopropyl | methyl | —(CH₂)₄— | hydrogen | 3-pyridyl |
| isopropyl | methyl | —(CH₂)₄— | hydrogen | phenyl |
| isopropyl | methyl | —(CH₂)₄— | ethyl | 3-pyridyl |
| isopropyl | methyl | —(CH₂)₄— | ethyl | phenyl |
| isopropyl | methyl | —(CH₂)₄— | propyl | 3-pyridyl |
| isopropyl | methyl | —(CH₂)₄— | propyl | phenyl |
| isopropyl | methyl | —(CH₂)₄— | ethoxymethyl | 3-pyridyl |
| isopropyl | methyl | —(CH₂)₄— | ethoxymethyl | phenyl |
| isopropyl | methyl | —(CH₂)₄— | butyl | 3-pyridyl |
| isopropyl | methyl | —(CH₂)₄— | butyl | phenyl |
| isopropyl | methyl | —CH₂C(CH₃)₂CH₂— | hydrogen | 3-pyridyl |
| isopropyl | methyl | —CH₂C(CH₃)₂CH₂— | hydrogen | phenyl |
| isopropyl | methyl | —CH₂C(CH₃)₂CH₂— | ethyl | 3-pyridyl |
| isopropyl | methyl | —CH₂C(CH₃)₂CH₂— | ethyl | phenyl |
| isopropyl | methyl | —CH₂C(CH₃)₂CH₂— | propyl | 3-pyridyl |
| isopropyl | methyl | —CH₂C(CH₃)₂CH₂— | propyl | phenyl |
| isopropyl | methyl | —CH₂C(CH₃)₂CH₂— | ethoxymethyl | 3-pyridyl |
| isopropyl | methyl | —CH₂C(CH₃)₂CH₂— | ethoxymethyl | phenyl |
| isopropyl | methyl | —CH₂C(CH₃)₂CH₂— | butyl | 3-pyridyl |
| isopropyl | methyl | —CH₂C(CH₃)₂CH₂— | butyl | phenyl |
| isopropyl | methyl | —(CH₂)₂O(CH₂)₂— | hydrogen | 3-pyridyl |
| isopropyl | methyl | —(CH₂)₂O(CH₂)₂— | hydrogen | phenyl |
| isopropyl | methyl | —(CH₂)₂O(CH₂)₂— | ethyl | 3-pyridyl |
| isopropyl | methyl | —(CH₂)₂O(CH₂)₂— | ethyl | phenyl |
| isopropyl | methyl | —(CH₂)₂O(CH₂)₂— | propyl | 3-pyridyl |
| isopropyl | methyl | —(CH₂)₂O(CH₂)₂— | propyl | phenyl |
| isopropyl | methyl | —(CH₂)₂O(CH₂)₂— | ethoxymethyl | 3-pyridyl |
| isopropyl | methyl | —(CH₂)₂O(CH₂)₂— | ethoxymethyl | phenyl |
| isopropyl | methyl | —(CH₂)₂O(CH₂)₂— | butyl | 3-pyridyl |
| isopropyl | methyl | —(CH₂)₂O(CH₂)₂— | butyl | phenyl |
| methyl | ethyl | —(CH₂)₃— | hydrogen | 3-pyridyl |
| methyl | ethyl | —(CH₂)₃— | hydrogen | phenyl |
| methyl | ethyl | —(CH₂)₃— | ethyl | 3-pyridyl |
| methyl | ethyl | —(CH₂)₃— | ethyl | phenyl |
| methyl | ethyl | —(CH₂)₃— | propyl | 3-pyridyl |
| methyl | ethyl | —(CH₂)₃— | propyl | phenyl |
| methyl | ethyl | —(CH₂)₃— | ethoxymethyl | 3-pyridyl |
| methyl | ethyl | —(CH₂)₃— | ethoxymethyl | phenyl |
| methyl | ethyl | —(CH₂)₃— | butyl | 3-pyridyl |
| methyl | ethyl | —(CH₂)₃— | butyl | phenyl |
| methyl | ethyl | —(CH₂)₄— | hydrogen | 3-pyridyl |
| methyl | ethyl | —(CH₂)₄— | hydrogen | phenyl |
| methyl | ethyl | —(CH₂)₄— | ethyl | 3-pyridyl |
| methyl | ethyl | —(CH₂)₄— | ethyl | phenyl |
| methyl | ethyl | —(CH₂)₄— | propyl | 3-pyridyl |
| methyl | ethyl | —(CH₂)₄— | propyl | phenyl |
| methyl | ethyl | —(CH₂)₄— | ethoxymethyl | 3-pyridyl |
| methyl | ethyl | —(CH₂)₄— | ethoxymethyl | phenyl |
| methyl | ethyl | —(CH₂)₄— | butyl | 3-pyridyl |
| methyl | ethyl | —(CH₂)₄— | butyl | phenyl |
| methyl | ethyl | —CH₂C(CH₃)₂CH₂— | hydrogen | 3-pyridyl |
| methyl | ethyl | —CH₂C(CH₃)₂CH₂— | hydrogen | phenyl |
| methyl | ethyl | —CH₂C(CH₃)₂CH₂— | ethyl | 3-pyridyl |
| methyl | ethyl | —CH₂C(CH₃)₂CH₂— | ethyl | phenyl |
| methyl | ethyl | —CH₂C(CH₃)₂CH₂— | propyl | 3-pyridyl |
| methyl | ethyl | —CH₂C(CH₃)₂CH₂— | propyl | phenyl |
| methyl | ethyl | —CH₂C(CH₃)₂CH₂— | ethoxymethyl | 3-pyridyl |
| methyl | ethyl | —CH₂C(CH₃)₂CH₂— | ethoxymethyl | phenyl |
| methyl | ethyl | —CH₂C(CH₃)₂CH₂— | butyl | 3-pyridyl |
| methyl | ethyl | —CH₂C(CH₃)₂CH₂— | butyl | phenyl |
| methyl | ethyl | —(CH₂)₂O(CH₂)₂— | hydrogen | 3-pyridyl |
| methyl | ethyl | —(CH₂)₂O(CH₂)₂— | hydrogen | phenyl |
| methyl | ethyl | —(CH₂)₂O(CH₂)₂— | ethyl | 3-pyridyl |
| methyl | ethyl | —(CH₂)₂O(CH₂)₂— | ethyl | phenyl |
| methyl | ethyl | —(CH₂)₂O(CH₂)₂— | propyl | 3-pyridyl |
| methyl | ethyl | —(CH₂)₂O(CH₂)₂— | propyl | phenyl |
| methyl | ethyl | —(CH₂)₂O(CH₂)₂— | ethoxymethyl | 3-pyridyl |
| methyl | ethyl | —(CH₂)₂O(CH₂)₂— | ethoxymethyl | phenyl |
| methyl | ethyl | —(CH₂)₂O(CH₂)₂— | butyl | 3-pyridyl |
| methyl | ethyl | —(CH₂)₂O(CH₂)₂— | butyl | phenyl |
| cyclopropyl | ethyl | —(CH₂)₃— | hydrogen | 3-pyridyl |
| cyclopropyl | ethyl | —(CH₂)₃— | hydrogen | phenyl |
| cyclopropyl | ethyl | —(CH₂)₃— | ethyl | 3-pyridyl |
| cyclopropyl | ethyl | —(CH₂)₃— | ethyl | phenyl |
| cyclopropyl | ethyl | —(CH₂)₃— | propyl | 3-pyridyl |
| cyclopropyl | ethyl | —(CH₂)₃— | propyl | phenyl |
| cyclopropyl | ethyl | —(CH₂)₃— | ethoxymethyl | 3-pyridyl |
| cyclopropyl | ethyl | —(CH₂)₃— | ethoxymethyl | phenyl |
| cyclopropyl | ethyl | —(CH₂)₃— | butyl | 3-pyridyl |
| cyclopropyl | ethyl | —(CH₂)₃— | butyl | phenyl |
| cyclopropyl | ethyl | —(CH₂)₄— | hydrogen | 3-pyridyl |
| cyclopropyl | ethyl | —(CH₂)₄— | hydrogen | phenyl |
| cyclopropyl | ethyl | —(CH₂)₄— | ethyl | 3-pyridyl |
| cyclopropyl | ethyl | —(CH₂)₄— | ethyl | phenyl |
| cyclopropyl | ethyl | —(CH₂)₄— | propyl | 3-pyridyl |
| cyclopropyl | ethyl | —(CH₂)₄— | propyl | phenyl |
| cyclopropyl | ethyl | —(CH₂)₄— | ethoxymethyl | 3-pyridyl |
| cyclopropyl | ethyl | —(CH₂)₄— | ethoxymethyl | phenyl |

-continued

| | | | | |
|---|---|---|---|---|
| cyclopropyl | ethyl | —(CH₂)₄— | butyl | 3-pyridyl |
| cyclopropyl | ethyl | —(CH₂)₄— | butyl | phenyl |
| cyclopropyl | ethyl | —CH₂C(CH₃)₂CH₂— | hydrogen | 3-pyridyl |
| cyclopropyl | ethyl | —CH₂C(CH₃)₂CH₂— | hydrogen | phenyl |
| cyclopropyl | ethyl | —CH₂C(CH₃)₂CH₂— | ethyl | 3-pyridyl |
| cyclopropyl | ethyl | —CH₂C(CH₃)₂CH₂— | ethyl | phenyl |
| cyclopropyl | ethyl | —CH₂C(CH₃)₂CH₂— | propyl | 3-pyridyl |
| cyclopropyl | ethyl | —CH₂C(CH₃)₂CH₂— | propyl | phenyl |
| cyclopropyl | ethyl | —CH₂C(CH₃)₂CH₂— | ethoxymethyl | 3-pyridyl |
| cyclopropyl | ethyl | —CH₂C(CH₃)₂CH₂— | ethoxymethyl | phenyl |
| cyclopropyl | ethyl | —CH₂C(CH₃)₂CH₂— | butyl | 3-pyridyl |
| cyclopropyl | ethyl | —CH₂C(CH₃)₂CH₂— | butyl | phenyl |
| cyclopropyl | ethyl | —(CH₂)₂O(CH₂)₂— | hydrogen | 3-pyridyl |
| cyclopropyl | ethyl | —(CH₂)₂O(CH₂)₂— | hydrogen | phenyl |
| cyclopropyl | ethyl | —(CH₂)₂O(CH₂)₂— | ethyl | 3-pyridyl |
| cyclopropyl | ethyl | —(CH₂)₂O(CH₂)₂— | ethyl | phenyl |
| cyclopropyl | ethyl | —(CH₂)₂O(CH₂)₂— | propyl | 3-pyridyl |
| cyclopropyl | ethyl | —(CH₂)₂O(CH₂)₂— | propyl | phenyl |
| cyclopropyl | ethyl | —(CH₂)₂O(CH₂)₂— | ethoxymethyl | 3-pyridyl |
| cyclopropyl | ethyl | —(CH₂)₂O(CH₂)₂— | ethoxymethyl | phenyl |
| cyclopropyl | ethyl | —(CH₂)₂O(CH₂)₂— | butyl | 3-pyridyl |
| cyclopropyl | ethyl | —(CH₂)₂O(CH₂)₂— | butyl | phenyl |
| isopropyl | ethyl | —(CH₂)₃— | hydrogen | 3-pyridyl |
| isopropyl | ethyl | —(CH₂)₃— | hydrogen | phenyl |
| isopropyl | ethyl | —(CH₂)₃— | ethyl | 3-pyridyl |
| isopropyl | ethyl | —(CH₂)₃— | ethyl | phenyl |
| isopropyl | ethyl | —(CH₂)₃— | propyl | 3-pyridyl |
| isopropyl | ethyl | —(CH₂)₃— | propyl | phenyl |
| isopropyl | ethyl | —(CH₂)₃— | ethoxymethyl | 3-pyridyl |
| isopropyl | ethyl | —(CH₂)₃— | ethoxymethyl | phenyl |
| isopropyl | ethyl | —(CH₂)₃— | butyl | 3-pyridyl |
| isopropyl | ethyl | —(CH₂)₃— | butyl | phenyl |
| isopropyl | ethyl | —(CH₂)₄— | hydrogen | 3-pyridyl |
| isopropyl | ethyl | —(CH₂)₄— | hydrogen | phenyl |
| isopropyl | ethyl | —(CH₂)₄— | ethyl | 3-pyridyl |
| isopropyl | ethyl | —(CH₂)₄— | ethyl | phenyl |
| isopropyl | ethyl | —(CH₂)₄— | propyl | 3-pyridyl |
| isopropyl | ethyl | —(CH₂)₄— | propyl | phenyl |
| isopropyl | ethyl | —(CH₂)₄— | ethoxymethyl | 3-pyridyl |
| isopropyl | ethyl | —(CH₂)₄— | ethoxymethyl | phenyl |
| isopropyl | ethyl | —(CH₂)₄— | butyl | 3-pyridyl |
| isopropyl | ethyl | —(CH₂)₄— | butyl | phenyl |
| isopropyl | ethyl | —CH₂C(CH₃)₂CH₂— | hydrogen | 3-pyridyl |
| isopropyl | ethyl | —CH₂C(CH₃)₂CH₂— | hydrogen | phenyl |
| isopropyl | ethyl | —CH₂C(CH₃)₂CH₂— | ethyl | 3-pyridyl |
| isopropyl | ethyl | —CH₂C(CH₃)₂CH₂— | ethyl | phenyl |
| isopropyl | ethyl | —CH₂C(CH₃)₂CH₂— | propyl | 3-pyridyl |
| isopropyl | ethyl | —CH₂C(CH₃)₂CH₂— | propyl | phenyl |
| isopropyl | ethyl | —CH₂C(CH₃)₂CH₂— | ethoxymethyl | 3-pyridyl |
| isopropyl | ethyl | —CH₂C(CH₃)₂CH₂— | ethoxymethyl | phenyl |
| isopropyl | ethyl | —CH₂C(CH₃)₂CH₂— | butyl | 3-pyridyl |
| isopropyl | ethyl | —CH₂C(CH₃)₂CH₂— | butyl | phenyl |
| isopropyl | ethyl | —(CH₂)₂O(CH₂)₂— | hydrogen | 3-pyridyl |
| isopropyl | ethyl | —(CH₂)₂O(CH₂)₂— | hydrogen | phenyl |
| isopropyl | ethyl | —(CH₂)₂O(CH₂)₂— | ethyl | 3-pyridyl |
| isopropyl | ethyl | —(CH₂)₂O(CH₂)₂— | ethyl | phenyl |
| isopropyl | ethyl | —(CH₂)₂O(CH₂)₂— | propyl | 3-pyridyl |
| isopropyl | ethyl | —(CH₂)₂O(CH₂)₂— | propyl | phenyl |
| isopropyl | ethyl | —(CH₂)₂O(CH₂)₂— | ethoxymethyl | 3-pyridyl |
| isopropyl | ethyl | —(CH₂)₂O(CH₂)₂— | ethoxymethyl | phenyl |
| isopropyl | ethyl | —(CH₂)₂O(CH₂)₂— | butyl | 3-pyridyl |
| isopropyl | ethyl | —(CH₂)₂O(CH₂)₂— | butyl | phenyl |

Certain exemplary compounds, including some of those described above in the Examples, have the following Formulas (Va, VIIa, VIIIb, and VIa) and the following R', $R_1$, X, and $R_2$ substituents, wherein each line of the table is matched with Formula IIIa, VIIa, VIIIb, or VIa to represent a specific embodiment of the invention.

| $R_1$ | R' | X | $R_2$ |
|---|---|---|---|
| methyl | hydrogen | —(CH₂)₃— | hydrogen |
| methyl | hydrogen | —(CH₂)₃— | ethyl |
| methyl | hydrogen | —(CH₂)₃— | propyl |
| methyl | hydrogen | —(CH₂)₃— | butyl |
| methyl | hydrogen | —(CH₂)₃— | ethoxymethyl |
| methyl | hydrogen | —(CH₂)₄— | hydrogen |
| methyl | hydrogen | —(CH₂)₄— | ethyl |
| methyl | hydrogen | —(CH₂)₄— | propyl |
| methyl | hydrogen | —(CH₂)₄— | butyl |
| methyl | hydrogen | —(CH₂)₄— | ethoxymethyl |
| methyl | hydrogen | —CH₂C(CH₃)₂CH₂— | hydrogen |

| | | | |
|---|---|---|---|
| methyl | hydrogen | —CH₂C(CH₃)₂CH₂— | ethyl |
| methyl | hydrogen | —CH₂C(CH₃)₂CH₂— | propyl |
| methyl | hydrogen | —CH₂C(CH₃)₂CH₂— | butyl |
| methyl | hydrogen | —CH₂C(CH₃)₂CH₂— | ethoxymethyl |
| methyl | hydrogen | —(CH₂)₂O(CH₂)₂— | hydrogen |
| methyl | hydrogen | —(CH₂)₂O(CH₂)₂— | ethyl |
| methyl | hydrogen | —(CH₂)₂O(CH₂)₂— | propyl |
| methyl | hydrogen | —(CH₂)₂O(CH₂)₂— | butyl |
| methyl | hydrogen | —(CH₂)₂O(CH₂)₂— | ethoxymethyl |
| cyclopropyl | hydrogen | —(CH₂)₃— | hydrogen |
| cyclopropyl | hydrogen | —(CH₂)₃— | ethyl |
| cyclopropyl | hydrogen | —(CH₂)₃— | propyl |
| cyclopropyl | hydrogen | —(CH₂)₃— | butyl |
| cyclopropyl | hydrogen | —(CH₂)₃— | ethoxymethyl |
| cyclopropyl | hydrogen | —(CH₂)₄— | hydrogen |
| cyclopropyl | hydrogen | —(CH₂)₄— | ethyl |
| cyclopropyl | hydrogen | —(CH₂)₄— | propyl |
| cyclopropyl | hydrogen | —(CH₂)₄— | butyl |
| cyclopropyl | hydrogen | —(CH₂)₄— | ethoxymethyl |
| cyclopropyl | hydrogen | —CH₂C(CH₃)₂CH₂— | hydrogen |
| cyclopropyl | hydrogen | —CH₂C(CH₃)₂CH₂— | ethyl |
| cyclopropyl | hydrogen | —CH₂C(CH₃)₂CH₂— | propyl |
| cyclopropyl | hydrogen | —CH₂C(CH₃)₂CH₂— | butyl |
| cyclopropyl | hydrogen | —CH₂C(CH₃)₂CH₂— | ethoxymethyl |
| cyclopropyl | hydrogen | —(CH₂)₂O(CH₂)₂— | hydrogen |
| cyclopropyl | hydrogen | —(CH₂)₂O(CH₂)₂— | ethyl |
| cyclopropyl | hydrogen | —(CH₂)₂O(CH₂)₂— | propyl |
| cyclopropyl | hydrogen | —(CH₂)₂O(CH₂)₂— | butyl |
| cyclopropyl | hydrogen | —(CH₂)₂O(CH₂)₂— | ethoxymethyl |
| isopropyl | hydrogen | —(CH₂)₃— | hydrogen |
| isopropyl | hydrogen | —(CH₂)₃— | ethyl |
| isopropyl | hydrogen | —(CH₂)₃— | propyl |
| isopropyl | hydrogen | —(CH₂)₃— | butyl |
| isopropyl | hydrogen | —(CH₂)₃— | ethoxymethyl |
| isopropyl | hydrogen | —(CH₂)₄— | hydrogen |
| isopropyl | hydrogen | —(CH₂)₄— | ethyl |
| isopropyl | hydrogen | —(CH₂)₄— | propyl |
| isopropyl | hydrogen | —(CH₂)₄— | butyl |
| isopropyl | hydrogen | —(CH₂)₄— | ethoxymethyl |
| isopropyl | hydrogen | —CH₂C(CH₃)₂CH₂— | hydrogen |
| isopropyl | hydrogen | —CH₂C(CH₃)₂CH₂— | ethyl |
| isopropyl | hydrogen | —CH₂C(CH₃)₂CH₂— | propyl |
| isopropyl | hydrogen | —CH₂C(CH₃)₂CH₂— | butyl |
| isopropyl | hydrogen | —CH₂C(CH₃)₂CH₂— | ethoxymethyl |
| isopropyl | hydrogen | —(CH₂)₂O(CH₂)₂— | hydrogen |
| isopropyl | hydrogen | —(CH₂)₂O(CH₂)₂— | ethyl |
| isopropyl | hydrogen | —(CH₂)₂O(CH₂)₂— | propyl |
| isopropyl | hydrogen | —(CH₂)₂O(CH₂)₂— | butyl |
| isopropyl | hydrogen | —(CH₂)₂O(CH₂)₂— | ethoxymethyl |
| methyl | methyl | —(CH₂)₃— | hydrogen |
| methyl | methyl | —(CH₂)₃— | ethyl |
| methyl | methyl | —(CH₂)₃— | propyl |
| methyl | methyl | —(CH₂)₃— | butyl |
| methyl | methyl | —(CH₂)₃— | ethoxymethyl |
| methyl | methyl | —(CH₂)₄— | hydrogen |
| methyl | methyl | —(CH₂)₄— | ethyl |
| methyl | methyl | —(CH₂)₄— | propyl |
| methyl | methyl | —(CH₂)₄— | butyl |
| methyl | methyl | —(CH₂)₄— | ethoxymethyl |
| methyl | methyl | —CH₂C(CH₃)₂CH₂— | hydrogen |
| methyl | methyl | —CH₂C(CH₃)₂CH₂— | ethyl |
| methyl | methyl | —CH₂C(CH₃)₂CH₂— | propyl |
| methyl | methyl | —CH₂C(CH₃)₂CH₂— | butyl |
| methyl | methyl | —CH₂C(CH₃)₂CH₂— | ethoxymethyl |
| methyl | methyl | —(CH₂)₂O(CH₂)₂— | hydrogen |
| methyl | methyl | —(CH₂)₂O(CH₂)₂— | ethyl |
| methyl | methyl | —(CH₂)₂O(CH₂)₂— | propyl |
| methyl | methyl | —(CH₂)₂O(CH₂)₂— | butyl |
| methyl | methyl | —(CH₂)₂O(CH₂)₂— | ethoxymethyl |
| cyclopropyl | methyl | —(CH₂)₃— | hydrogen |
| cyclopropyl | methyl | —(CH₂)₃— | ethyl |
| cyclopropyl | methyl | —(CH₂)₃— | propyl |
| cyclopropyl | methyl | —(CH₂)₃— | butyl |
| cyclopropyl | methyl | —(CH₂)₃— | ethoxymethyl |
| cyclopropyl | methyl | —(CH₂)₄— | hydrogen |
| cyclopropyl | methyl | —(CH₂)₄— | ethyl |
| cyclopropyl | methyl | —(CH₂)₄— | propyl |
| cyclopropyl | methyl | —(CH₂)₄— | butyl |
| cyclopropyl | methyl | —(CH₂)₄— | ethoxymethyl |
| cyclopropyl | methyl | —CH₂C(CH₃)₂CH₂— | hydrogen |
| cyclopropyl | methyl | —CH₂C(CH₃)₂CH₂— | ethyl |
| cyclopropyl | methyl | —CH₂C(CH₃)₂CH₂— | propyl |
| cyclopropyl | methyl | —CH₂C(CH₃)₂CH₂— | butyl |
| cyclopropyl | methyl | —CH₂C(CH₃)₂CH₂— | ethoxymethyl |
| cyclopropyl | methyl | —(CH₂)₂O(CH₂)₂— | hydrogen |
| cyclopropyl | methyl | —(CH₂)₂O(CH₂)₂— | ethyl |
| cyclopropyl | methyl | —(CH₂)₂O(CH₂)₂— | propyl |
| cyclopropyl | methyl | —(CH₂)₂O(CH₂)₂— | butyl |
| cyclopropyl | methyl | —(CH₂)₂O(CH₂)₂— | ethoxymethyl |
| isopropyl | methyl | —(CH₂)₃— | hydrogen |
| isopropyl | methyl | —(CH₂)₃— | ethyl |
| isopropyl | methyl | —(CH₂)₃— | propyl |
| isopropyl | methyl | —(CH₂)₃— | butyl |
| isopropyl | methyl | —(CH₂)₃— | ethoxymethyl |
| isopropyl | methyl | —(CH₂)₄— | hydrogen |
| isopropyl | methyl | —(CH₂)₄— | ethyl |
| isopropyl | methyl | —(CH₂)₄— | propyl |
| isopropyl | methyl | —(CH₂)₄— | butyl |
| isopropyl | methyl | —(CH₂)₄— | ethoxymethyl |
| isopropyl | methyl | —CH₂C(CH₃)₂CH₂— | hydrogen |
| isopropyl | methyl | —CH₂C(CH₃)₂CH₂— | ethyl |
| isopropyl | methyl | —CH₂C(CH₃)₂CH₂— | propyl |
| isopropyl | methyl | —CH₂C(CH₃)₂CH₂— | butyl |
| isopropyl | methyl | —CH₂C(CH₃)₂CH₂— | ethoxymethyl |
| isopropyl | methyl | —(CH₂)₂O(CH₂)₂— | hydrogen |
| isopropyl | methyl | —(CH₂)₂O(CH₂)₂— | ethyl |
| isopropyl | methyl | —(CH₂)₂O(CH₂)₂— | propyl |
| isopropyl | methyl | —(CH₂)₂O(CH₂)₂— | butyl |
| isopropyl | methyl | —(CH₂)₂O(CH₂)₂— | ethoxymethyl |
| methyl | ethyl | —(CH₂)₃— | hydrogen |
| methyl | ethyl | —(CH₂)₃— | ethyl |
| methyl | ethyl | —(CH₂)₃— | propyl |
| methyl | ethyl | —(CH₂)₃— | butyl |
| methyl | ethyl | —(CH₂)₃— | ethoxymethyl |
| methyl | ethyl | —(CH₂)₄— | hydrogen |
| methyl | ethyl | —(CH₂)₄— | ethyl |
| methyl | ethyl | —(CH₂)₄— | propyl |
| methyl | ethyl | —(CH₂)₄— | butyl |
| methyl | ethyl | —(CH₂)₄— | ethoxymethyl |
| methyl | ethyl | —CH₂C(CH₃)₂CH₂— | hydrogen |
| methyl | ethyl | —CH₂C(CH₃)₂CH₂— | ethyl |
| methyl | ethyl | —CH₂C(CH₃)₂CH₂— | propyl |
| methyl | ethyl | —CH₂C(CH₃)₂CH₂— | butyl |
| methyl | ethyl | —CH₂C(CH₃)₂CH₂— | ethoxymethyl |
| methyl | ethyl | —(CH₂)₂O(CH₂)₂— | hydrogen |
| methyl | ethyl | —(CH₂)₂O(CH₂)₂— | ethyl |
| methyl | ethyl | —(CH₂)₂O(CH₂)₂— | propyl |
| methyl | ethyl | —(CH₂)₂O(CH₂)₂— | butyl |
| methyl | ethyl | —(CH₂)₂O(CH₂)₂— | ethoxymethyl |
| cyclopropyl | ethyl | —(CH₂)₃— | hydrogen |
| cyclopropyl | ethyl | —(CH₂)₃— | ethyl |
| cyclopropyl | ethyl | —(CH₂)₃— | propyl |
| cyclopropyl | ethyl | —(CH₂)₃— | butyl |
| cyclopropyl | ethyl | —(CH₂)₃— | ethoxymethyl |
| cyclopropyl | ethyl | —(CH₂)₄— | hydrogen |
| cyclopropyl | ethyl | —(CH₂)₄— | ethyl |
| cyclopropyl | ethyl | —(CH₂)₄— | propyl |
| cyclopropyl | ethyl | —(CH₂)₄— | butyl |
| cyclopropyl | ethyl | —(CH₂)₄— | ethoxymethyl |
| cyclopropyl | ethyl | —CH₂C(CH₃)₂CH₂— | hydrogen |
| cyclopropyl | ethyl | —CH₂C(CH₃)₂CH₂— | ethyl |
| cyclopropyl | ethyl | —CH₂C(CH₃)₂CH₂— | propyl |
| cyclopropyl | ethyl | —CH₂C(CH₃)₂CH₂— | butyl |
| cyclopropyl | ethyl | —CH₂C(CH₃)₂CH₂— | ethoxymethyl |
| cyclopropyl | ethyl | —(CH₂)₂O(CH₂)₂— | hydrogen |
| cyclopropyl | ethyl | —(CH₂)₂O(CH₂)₂— | ethyl |
| cyclopropyl | ethyl | —(CH₂)₂O(CH₂)₂— | propyl |
| cyclopropyl | ethyl | —(CH₂)₂O(CH₂)₂— | butyl |
| cyclopropyl | ethyl | —(CH₂)₂O(CH₂)₂— | ethoxymethyl |
| isopropyl | ethyl | —(CH₂)₃— | hydrogen |
| isopropyl | ethyl | —(CH₂)₃— | ethyl |
| isopropyl | ethyl | —(CH₂)₃— | propyl |
| isopropyl | ethyl | —(CH₂)₃— | butyl |
| isopropyl | ethyl | —(CH₂)₃— | ethoxymethyl |
| isopropyl | ethyl | —(CH₂)₄— | hydrogen |
| isopropyl | ethyl | —(CH₂)₄— | ethyl |
| isopropyl | ethyl | —(CH₂)₄— | propyl |
| isopropyl | ethyl | —(CH₂)₄— | butyl |

-continued

| | | | |
|---|---|---|---|
| isopropyl | ethyl | —(CH$_2$)$_4$— | ethoxymethyl |
| isopropyl | ethyl | —CH$_2$C(CH$_3$)$_2$CH$_2$— | hydrogen |
| isopropyl | ethyl | —CH$_2$C(CH$_3$)$_2$CH$_2$— | ethyl |
| isopropyl | ethyl | —CH$_2$C(CH$_3$)$_2$CH$_2$— | propyl |
| isopropyl | ethyl | —CH$_2$C(CH$_3$)$_2$CH$_2$— | butyl |
| isopropyl | ethyl | —CH$_2$C(CH$_3$)$_2$CH$_2$— | ethoxymethyl |
| isopropyl | ethyl | —(CH$_2$)$_2$O(CH$_2$)$_2$— | hydrogen |
| isopropyl | ethyl | —(CH$_2$)$_2$O(CH$_2$)$_2$— | ethyl |
| isopropyl | ethyl | —(CH$_2$)$_2$O(CH$_2$)$_2$— | propyl |
| isopropyl | ethyl | —(CH$_2$)$_2$O(CH$_2$)$_2$— | butyl |
| isopropyl | ethyl | —(CH$_2$)$_2$O(CH$_2$)$_2$— | ethoxymethyl |

Cytokine Induction in Human Cells

Compounds of the invention have been found to induce cytokine biosynthesis when tested using the method described below.

An in vitro human blood cell system is used to assess cytokine induction. Activity is based on the measurement of interferon ($\alpha$) and tumor necrosis factor ($\alpha$) (IFN and TNF, respectively) secreted into culture media as described by Testerman et. al. in "Cytokine Induction by the Immunomodulators Imiquimod and S-27609," *Journal of Leukocyte Biology*, 58, 365-372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at 4×10$^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 micromolar ($\mu$M).

Incubation

The solution of test compound is added at 60 $\mu$M to the first well containing RPMI complete and serial 3 fold dilutions are made in the wells. The PBMC suspension is then added to the wells in an equal volume, bringing the test compound concentrations to the desired range (30-0.014 $\mu$M). The final concentration of PBMC suspension is 2×10$^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed with a sterile polypropylene pipet and transferred to sterile polypropylene tubes. Samples are maintained at −30° C. to −70° C. until analysis. The samples are analyzed for interferon ($\alpha$) by ELISA and for tumor necrosis factor ($\alpha$) by ELISA or IGEN Assay.

Interferon ($\alpha$) and Tumor Necrosis Factor ($\alpha$) Analysis by ELISA

Interferon ($\alpha$) concentration is determined by ELISA using a Human Multi-Species kit from PBL Biomedical Laboratories, New Brunswick, N.J. Results are expressed in pg/mL.

Tumor necrosis factor ($\alpha$)(TNF) concentration is determined using ELISA kits available from Biosource International, Camarillo, Calif. Alternately, the TNF concentration can be determined by ORIGEN M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the formula (II):

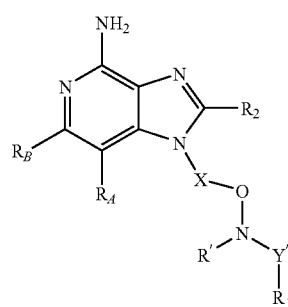

wherein:
X is selected from the group consisting of —CH(R$_{9a}$)-alkylene- and —CH(R$_{9a}$)-alkenylene-, wherein the alkylene and alkenylene are optionally interrupted by one or more —O— groups;
Y' is selected from the group consisting of:
a bond,
—C(O)—,
—C(S)—,
—S(O)$_2$—,
—S(O)$_2$—N(R$_8$)—,

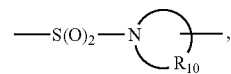

C(O)—O—,
—C(O)—N(R$_8$)—,
—C(S)—N(R$_8$)—,
—C(O)—N(R$_8$)—S(O)$_2$—,
—C(O)—N(R$_8$)—C(O)—,
—C(S)—N(R$_8$)—C(O)—,

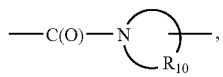

—C(O)—C(O)—,
—C(O)—C(O)—O—, and
—C(=NH)—N(R$_8$)—;

R$_1$ and R' are independently selected from the group consisting of
hydrogen,
alkyl,
alkenyl,
aryl,
arylalkylenyl,
heteroaryl,
heteroarylalkylenyl,
heterocyclyl, and
heterocyclylalkylenyl,
  wherein the alkyl, alkenyl, aryl, arylalkylenyl, heteroaryl, heteroarylalkylenyl, heterocyclyl, or heterocyclylalkylenyl group is unsubstituted or substituted by one or more substituents selected from the group consisting of:
hydroxyl,
alkyl,
haloalkyl,
hydroxyalkyl,
alkoxy,
dialkylamino,
—S(O)$_{0-2}$-alkyl,
—S(O)$_{0-2}$-aryl,
—NH—S(O)$_2$-alkyl,
—NH—S(O)$_2$-aryl,
haloalkoxy,
halogen,
nitrile,
nitro,
aryl,
heteroaryl,
heterocyclyl,
aryloxy,
arylalkyleneoxy,
—C(O)—O-alkyl,
—C(O)—N(R$_8$)$_2$,
—N(R$_8$)—C(O)-alkyl,
—O—C(O)-alkyl, and
—C(O)-alkyl;

or R$_1$ and R' together with the nitrogen atom and Y' to which they are bonded can join to form a ring selected from the group consisting of:

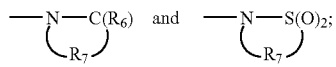

R$_A$ and R$_B$ are taken together to form a fused aryl ring, wherein the aryl ring is unsubstituted or substituted by one or more R groups, or substituted by one R$_3$ group, or substituted by one R$_3$ group and one R group;

R is selected from the group consisting of:
halogen,
hydroxyl,
alkyl,
alkenyl,
haloalkyl,
alkoxy,
alkylthio, and
—N(R$_9$)$_2$;

R$_2$ is selected from the group consisting of:
—R$_{11}$,
—X″—R$_{11}$, and
—X″—Y‴—R$_{11}$;

R$_3$ is selected from the group consisting of:
—Z—R$_4$,
—Z—X'—R$_4$,
—Z—X'—y—R$_4$, and
—Z—X'—R$_5$;

each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

each X″ is independently selected from the group consisting of alkylene, alkenylene, alkynylene, wherein the alkylene, alkenylene, and alkynylene groups can be optionally interrupted by one or more —O— groups;

each Y is independently selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

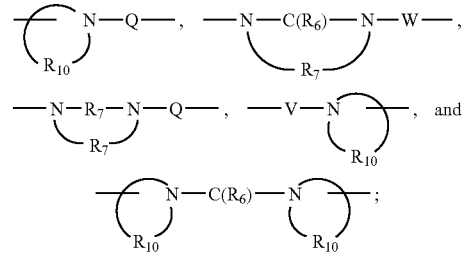

each Y‴ is independently selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)—O—,
—C(R$_6$)—N(R$_8$)—,
—O—C(R$_6$)—N(R$_8$)—, and
—C(R$_6$)—N(OR$_9$)—;

Z is a bond or —O—;

each R$_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alklheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylannino)alkyleneoxy, and in the case of alkyl, alkenyl, alkynyl, and heterocyclyl, oxo;

each $R_5$ is independently selected from the group consisting of:

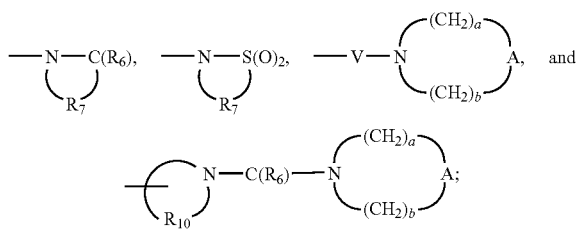

each $R_6$ is independently selected from the group consisting of =O and =S;

each $R_7$ is independently $C_{2-7}$ alkylene;

each $R_8$ is independently selected from the group consisting of hydrogen, $C_{1-10}$ alkyl, $C_{2-10}$ alkenyl, $C_{1-10}$ alkoxy—$C_{1-10}$ alkylenyl, and aryl—$C_{1-10}$ alkylenyl;

each $R_9$ is independently selected from the group consisting of hydrogen and alkyl;

$R_{9a}$ is selected from the group consisting of hydrogen and alkyl which is optionally interrupted by one or more —O— groups;

each $R_{10}$ is independently $C_{3-8}$ alkylene;

each $R_{11}$ is independently selected from the group consisting of hydrogen, alkyl, alkenyl, alkynyl, wherein the alkyl, alkenyl, and alkynyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, amino, alkylamino, dialkylamino, (dialkylamino)alkyleneoxy, and in the case of alkyl, alkenyl, and alkynyl, oxo;

each A is independently selected from the group consisting of —O—, —C(O)—, —CH$_2$—, —S(O)$_{0-2}$—, and —N(R$_4$)—;

each Q is independently selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

each W is independently selected from the group consisting of a bond, —C(O)—, and —S(O)$_2$—;

each V is independently selected from the group consisting of —C(R$_6$)—, —O—C(R$_6$)—, —N(R$_8$)—C(R$_6$)—, and —S(O)$_2$—; and a and b are independently integers from 1 to 6 with the proviso that a+b is ≦7;

or a pharmaceutically acceptable salt thereof.

2. The compound or salt of claim 1 wherein X is —C$_{3-5}$ alkylene- or —CH$_2$CH$_2$OCH$_2$CH$_2$—.

3. The compound or salt of claim 1 wherein R' is selected from the group consisting of hydrogen and C$_{1-4}$ alkyl.

4. The compound or salt of claim 1 wherein Y' is —C(O)—, —S(O)$_2$—, or —C(O)—N(R$_8$)—.

5. The compound or salt of claim 1 wherein R$_1$ is selected from the group consisting of C$_{1-6}$ alkyl and pyridyl.

6. The compound or salt of claim 1 wherein R$_1$ is selected from the group consisting of alkyl, alkenyl, aryl, and heteroaryl, each of which is optionally substituted by one or more substituents selected from the group consisting of —O-alkyl, —O-aryl, —S-alkyl, —S-aryl, halogen, —O—C(O)-alkyl, —C(O)—O-alkyl, haloalkoxy, haloalkyl, and aryl.

7. The compound or salt of claim 1 wherein R$_2$ is selected from the group consisting of hydrogen, alkyl, and alkoxyalkylenyl.

8. The compound or salt of claim 7 wherein R$_2$ is selected from the group consisting of hydrogen, methyl, ethyl, propyl, butyl, ethoxymethyl, 2-methoxyethyl, and methoxymethyl.

9. The compound or salt of claim 1 wherein R$_2$ is selected from the group consisting of:
hydrogen,
alkyl,
alkenyl,
alkylene-Y"-alkyl, and
alkylene-Y"-alkenyl,
wherein the alkyl or alkenyl group is unsubstituted or substituted by one or more substituents selected from the group consisting of:
hydroxyl,
halogen,
—N(R$_{8a}$)$_2$,
—C(O)—C$_{1-10}$ alkyl,
—C(O)—O—C$_{1-10}$ alkyl, and
N$_3$;
wherein:
Y" is —O— or —S(O)$_{0-2}$—; and
each R$_{8a}$ is independently selected from the group consisting of hydrogen, C$_{1-10}$ alkyl, and C$_{2-10}$ alkenyl.

10. The compound or salt of claim 1 wherein R$_A$ and R$_B$ form a fused aryl ring wherein the aryl ring is unsubstituted.

11. A compound of the formula (III):

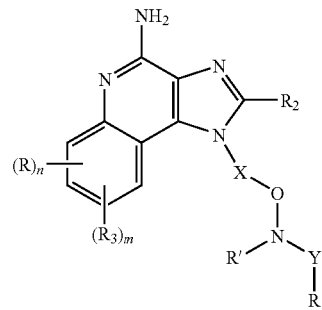

wherein:
X is selected from the group consisting of —CH(R$_{9a}$)-alkylene- and —CH(R$_{9a}$)-alkenylene-, wherein the alkylene and alkenylene are optionally interrupted by one or more —O— groups;

Y' is selected from the group consisting of:
a bond,
—C(O)—,
—C(S)—,
—S(O)$_2$—,

—S(O)₂—N(R₈)—,

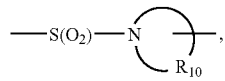

—C(O)—O—,
—C(O)—N(R₈)—,
—C(S)—N(R₈)—,
—C(O)—N(R₈)—S(O)₂—,
—C(O)—N(R₈)—C(O)—,
—C(S)—N(R₈)—C(O)—,

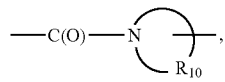

—C(O)—C(O)—,
—C(O)—C(O)—O—, and
—C(=NH)—N(R₈)—;

each R is independently selected from the group consisting of:
  halogen,
  hydroxyl,
  alkyl,
  alkenyl,
  haloalkyl,
  alkoxy,
  alkylthio, and
  —N(R₉)₂;

R₁ and R' are independently selected from the group consisting of:
  hydrogen,
  alkyl,
  alkenyl,
  aryl,
  arylalkylenyl,
  heteroaryl,
  heteroarylalkylenyl,
  heterocyclyl, and
  heterocyclylalkylenyl,
  wherein the alkyl, alkenyl, aryl, arylalkylenyl, heteroaryl, heteroarylalkylenyl, heterocyclyl, or heterocyclylalkylenyl group is unsubstituted or substituted by one or more substituents selected from the group consisting of:
    hydroxyl,
    alkyl,
    haloalkyl,
    hydroxyalkyl,
    alkoxy,
    dialkylamino,
    —S(O)₀₋₂-alkyl,
    —S(O)₀₋₂-aryl,
    —NH—S(O)₂-alkyl,
    —NH—S(O)₂-aryl,
    haloalkoxy,
    halogen,
    nitrile,
    nitro,
    aryl,
    heteroaryl,
    heterocyclyl,
    aryloxy,
    arylalkyleneoxy,
    —C(O)—O-alkyl,
    —C(O)—N(R₈)₂,
    —N(R₈)—C(O)-alkyl,
    —O—C(O)-alkyl, and
    —C(O)-alkyl;

or R₁ and R' together with the nitrogen atom and Y' to which they are bonded can join to form a ring selected from the group consisting of:

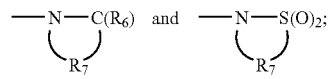

R₂ is selected from the group consisting of:
  —R₁₁,
  —X"—R₁₁, and
  —X"—Y'"—R₁₁;

R₃ is selected from the group consisting of:
  —Z—R₄,
  —Z—X'—R₄,
  —Z—X'—Y—R₄, and
  —Z—X'—R₅;

each X' is independently selected from the group consisting of alkylene, alkenylene, alkynylene, arylene, heteroarylene, and heterocyclylene, wherein the alkylene, alkenylene, and alkynylene groups can be optionally interrupted or terminated with arylene, heteroarylene, or heterocyclylene, and optionally interrupted by one or more —O— groups;

each X" is independently selected from the group consisting of alkylene, alkenylene, alkynylene, wherein the alkylene, alkenylene, and alkynylene groups can be optionally interrupted by one or more —O— groups;

each Y is independently selected from the group consisting of:
  —S(O)₀₋₂—,
  —S(O)₂—N(R₈)—,
  —C(R₆)—,
  —C(R₆)—O—,
  —O—C(R₆)—,
  —O—C(O)—O—,
  —N(R₈)-Q-,
  —C(R₆)—N(R₈)—,
  —O—C(R₆)—N(R₈)—,
  —C(R₆)—N(OR₉)—,

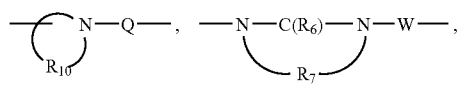

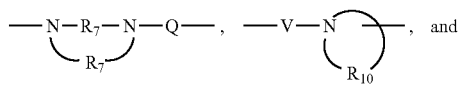

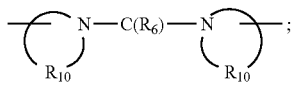

each Y'" is independently selected from the group consisting of:
  —S(O)₀₋₂—,
  —S(O)₂—N(R₈)—,
  —C(R₆)—, —C($R_6$)—O—,
—O—C($R_6$)—,
—O—C(O)—O—,
—N($R_8$)—O—,
—C($R_6$)—N($R_8$)—,
—O—C($R_6$)—N($R_8$)—,
—C($R_6$)—N(O$R_9$)—;

Z is a bond or —O—;

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alklheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylannino)alkyleneoxy, and in the case of alkyl, alkenyl, alkynyl, and heterocyclyl, oxo;

each $R_5$ is independently selected from the group consisting of:

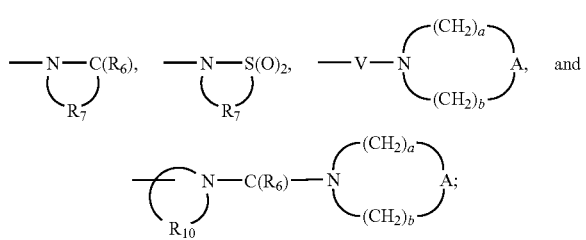

each $R_6$ is independently selected from the group consisting of =O and =S;

each $R_7$ is independently $C_{2-7}$ alkylene;

each $R_8$ is independently selected from the group consisting of hydrogen, $C_{1-10}$ alkyl, $C_{2-10}$ alkenyl, $C_{1-10}$ alkoxy—$C_{1-10}$ alkylenyl, and aryl-$C_{1-10}$ alkylenyl;

each $R_9$ is independently selected from the group consisting of hydrogen and alkyl;

$R_{9a}$ is selected from the group consisting of hydrogen and alkyl which is optionally interrupted by one or more —O— groups;

each $R_{10}$ is independently $C_{3-8}$ alkylene;

each $R_{11}$ is independently selected from the group consisting of hydrogen, alkyl, alkenyl, alkynyl, wherein the alkyl, alkenyl, and alkynyl groups can be unsubstituted or substituted by one or more substituents independently selected from the group consisting of alkyl, alkoxy, hydroxyalkyl, haloalkyl, haloalkoxy, halogen, nitro, hydroxyl, mercapto, cyano, amino, alkylamino, dialkylamino, (dialkylamino)alkyleneoxy, and in the case of alkyl, alkenyl, and alkynyl, oxo;

each A is independently selected from the group consisting of —O—, —C(O)—, —CH$_2$—, —S(O)$_{0-2}$—, and —N($R_4$)—;

each Q is independently selected from the group consisting of a bond, —C($R_6$)—, —C($R_6$)—C($R_6$)—, —S(O)$_0$—,
—C($R_6$)—N($R_8$)—W—, —S(O)$_2$—N($R_8$)—, —C($R_6$)—O—, and —C($R_6$)—N(O$R_9$)—;

each W is independently selected from the group consisting of a bond, —C(O)—, and —S(O)$_2$—;

each V is independently selected from the group consisting of —C($R_6$)—, —O—C($R_6$)—, —N($R_8$)—C($R_6$)—, and —S(O)$_2$—;

a and b are independently integers from 1 to 6 with the proviso that a+b is $\leq 7$;

n is an integer from 0 to 4; and m is 0 or 1, with the proviso that when m is 1, n is 0 or 1;

or a pharmaceutically acceptable salt thereof.

12. The compound or salt of claim 11 wherein X is —$C_{3-5}$ alkylene- or —CH$_2$CH$_2$OCH$_2$CH$_2$—.

13. The compound or salt of claim 11 wherein R' is selected from the group consisting of hydrogen and $C_{1-4}$ alkyl.

14. The compound or salt of claim 11 wherein Y' is —C(O)—, —S(O)$_2$—, or —C(O)—N($R_8$)—.

15. The compound or salt of claim 11 wherein $R_1$ is selected from the group consisting of $C_{1-6}$ alkyl and pyridyl.

16. The compound or salt of claim 11 wherein $R_1$ is selected from the group consisting of alkyl, alkenyl, aryl, and heteroaryl, each of which is optionally substituted by one or more substituents selected from the group consisting of —O-alkyl, —O-aryl, —S-alkyl, —S-aryl, halogen, —O—C(O)-alkyl, —C(O)—O-alkyl, haloalkoxy, haloalkyl, and aryl.

17. The compound or salt of claim 11 wherein $R_2$ is selected from the group consisting of hydrogen, alkyl, and alkoxyalkylenyl.

18. The compound or salt of claim 17 wherein $R_2$ is selected from the group consisting of hydrogen, methyl, ethyl, propyl, butyl, ethoxymethyl, 2-methoxyethyl, and methoxymethyl.

19. The compound or salt of claim 11 wherein $R_2$ is selected from the group consisting of:

hydrogen, alkyl, alkenyl, alkylene—Y"-alkyl, and alkylene—Y"-alkenyl, wherein the alkyl or alkenyl group is unsubstituted or substituted by one or more substituents selected from the group consisting of:

hydroxyl, halogen,

N($R_{8a}$)$_2$,

—C(O)—$C_{1-10}$ alkyl,

—C(O)—O—$C_{1-10}$ alkyl, and

—N$_3$, wherein:

Y" is —O— or —S(O)$_{0-2}$—; and each $R_{8a}$ is independently selected from the group consisting of hydrogen, $C_{1-10}$ alkyl, and $C_{2-10}$ alkenyl.

20. The compound or salt of claim 11 wherein m and n are each 0.

21. A compound of the formula (V):

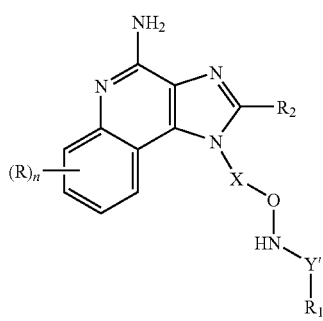

wherein:
X is selected from the group consisting of —CH($R_{9a}$)-alkylene- and —CH($R_{9a}$)-alkenylene-;
Y' is selected from the group consisting of
a bond,
—C(O)—,
—C(S)—,
—S(O)2-,
—S(O)$_2$—N($R_{8a}$)—,
—C(O)—O—,
C(O)—N($R_{8a}$)
C(S)—N($R_{8a}$)—,
C(O)N($R_{8a}$)—S(O)$_2$—,
C(O)—N($R_{8a}$)—C(O)—,
—C(S)—N($R_{8a}$)—C(O)—, and
—C(O)—C(O)—O—;
$R_1$ is selected from the group consisting of:
hydrogen,
alkyl,
alkenyl,
aryl,
alkylene-aryl,
alkylene-heteroaryl,
alkylene-heterocyclyl,
heteroaryl, and
heterocyclyl,
wherein the alkyl, alkenyl, aryl, arylalkylenyl, heteroarylalkylenyl, heterocyclylalkylenyl, heteroaryl or heterocyclyl group is unsubstituted or substituted by one or more substituents selected from the group consisting of:
hydroxyl,
alkyl,
haloalkyl,
hydroxyalkyl,
—O-alkyl,
—S(O)$_{0-2}$-alkyl,
—S(O)$_{0-2}$-aryl,
—O-haloalkyl,
halogen,
nitrile,
nitro,
aryl,
heteroaryl,
heterocyclyl,
—O-aryl,
—O-alkylene-aryl,
—C(O)—O-alkyl,
—C(O)—N($R_{8a}$)$_2$,
N($R_{8a}$)—C(O)-alkyl,
—O—C(O)-alkyl, and
—C(O)-alkyl;
each R is independently selected from the group consisting of alkyl, alkoxy, halogen, hydroxyl, and trifluoromethyl;
$R_2$ is selected from the group consisting of:
hydrogen,
alkyl,
alkenyl,
alkylene-Y"-alkyl,
alkylene-Y"-alkenyl, and
alkyl or alkenyl substituted by one or more substituents selected from the group consisting of:
hydroxyl,
halogen,
—N($R_{8a}$)$_2$,
—C(O)—$C_{1-10}$ alkyl,
—C(O)—O—$C_{1-10}$ alkyl, and
$N_3$;
Y" is —O— or —S(O)$_{0-2}$—;
each $R_{8a}$ is independently selected from the group consisting of hydrogen, $C_{1-10}$ alkyl, and $C_{2-10}$ alkenyl;
$R_{9a}$ is selected from the group consisting of hydrogen and alkyl which may be optionally interrupted by one or more —O— groups; and
n is an integer from 0 to 4;
or a pharmaceutically acceptable salt thereof.

22. A pharmaceutical composition comprising a therapeutically effective amount of a compound or salt of claim 1 in combination with a pharmaceutically acceptable carrier.

23. A method of inducing INF and/or TNF biosynthesis in an animal comprising administering an effective amount of a compound or salt of claim 1 to the animal.

24. A pharmaceutical composition comprising a therapeutically effective amount of a compound or salt of claim 11 in combination with a pharmaceutically acceptable carrier.

25. A method of inducing INF and/or TNF biosynthesis in an animal comprising administering an effective amount of a compound or salt of claim 11 to the animal.

* * * * *

UNITED STATES PATENT AND TRADEMARK OFFICE
CERTIFICATE OF CORRECTION

PATENT NO. : 7,648,997 B2 Page 1 of 1
APPLICATION NO. : 10/595058
DATED : January 19, 2010
INVENTOR(S) : Kshirsagar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 610 days.

Signed and Sealed this

Twenty-third Day of November, 2010

David J. Kappos
*Director of the United States Patent and Trademark Office*